(12) United States Patent
Hernandez-O'Farrill et al.

(10) Patent No.: US 11,446,299 B2
(45) Date of Patent: *Sep. 20, 2022

(54) CARBAZOLE EHOP-016 DERIVATIVES AS ANTICANCER AND ANTI-MIGRATORY AGENTS

(71) Applicant: UNIVERSITY OF PUERTO RICO, San Juan, PR (US)

(72) Inventors: Eliud Hernandez-O'Farrill, San Juan, PR (US); Cornelis P. Vlaar, San Juan, PR (US); Suranganie Dharmawardhane Flanagan, San Juan, PR (US); Linette Castillo-Pichardo, San Juan, PR (US)

(73) Assignee: UNIVERSITY OF PUERTO RICO, San Juan, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/923,853

(22) Filed: Jul. 8, 2020

(65) Prior Publication Data

US 2020/0352941 A1 Nov. 12, 2020

Related U.S. Application Data

(63) Continuation of application No. 16/168,612, filed on Oct. 23, 2018, now Pat. No. 10,729,689.

(Continued)

(51) Int. Cl.
  *C07D 403/12* (2006.01)
  *C07D 403/14* (2006.01)
(Continued)

(52) U.S. Cl.
  CPC ........ *A61K 31/506* (2013.01); *A61K 31/5377* (2013.01); *A61P 35/00* (2018.01);
(Continued)

(58) Field of Classification Search
  CPC ........................... C07D 403/12; C07D 403/14
  See application file for complete search history.

(56) References Cited

U.S. PATENT DOCUMENTS 6,423,723 B1 7/2002 Tayer
8,884,006 B2 11/2014 Hernandez
(Continued)

FOREIGN PATENT DOCUMENTS

WO    WO 2001/07409    2/2001
WO    WO 2012/172482   12/2012

OTHER PUBLICATIONS

PubChem printout Jan. 25, 2012.*
(Continued)

*Primary Examiner* — Valerie Rodriguez-Garcia
(74) *Attorney, Agent, or Firm* — Barnes & Thornburg LLP; Alice O. Martin

(57) ABSTRACT

A series of novel EHop-016 derivatives is presented herein via designing and synthesizing compounds that mimics its more favorable "U-shaped" conformation that appears to be critical for inhibitory activity against Rac. Based on modeling studies on EHop-016, compounds with a more rigid structural conformation can mimic this "U-shaped" conformation and would improve the anti-migration activity against metastatic cells. Compounds are disclosed that inhibit RhoGTPases that are useful for inhibiting hyperpro- (Continued)

filerative and neoplastic diseases, for instance compounds of formula

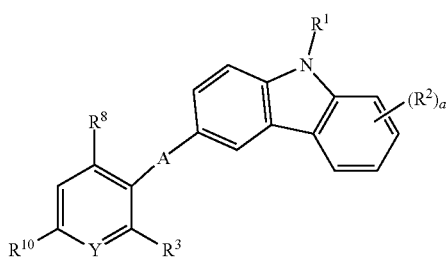

Specifically, the compounds inhibit the GTPases Rac and Cdc42 that are overactive or overexpressed in signaling pathways in cancer and metastasis. Methods for treatment of cancer and hyperproliferative diseases are disclosed.

8 Claims, 14 Drawing Sheets

Related U.S. Application Data

(60) Provisional application No. 62/577,305, filed on Oct. 26, 2017.

(51) Int. Cl.
| | | |
|---|---|---|
| *A61K 31/506* | (2006.01) | |
| *C07D 401/14* | (2006.01) | |
| *A61P 35/00* | (2006.01) | |
| *A61K 31/5377* | (2006.01) | |

(52) U.S. Cl.
CPC ......... *C07D 401/14* (2013.01); *C07D 403/12* (2013.01); *C07D 403/14* (2013.01)

(56) References Cited

U.S. PATENT DOCUMENTS

2012/0319050 A1  12/2012  Metz
2013/0172552 A1  7/2013  Hernandez et al.

OTHER PUBLICATIONS

PubChem printout Oct. 18, 2012.*
CAS printout-Ukrorgsyntez Ltd. RN: 1647685-14-0 Entered STN: Feb. 15, 2015.*
CAS printout-AKos RN:880618-39-3 Entered STN: Apr. 17, 2006.*
Bashir et al., "Recent Developments and Biological Activities of N-Substituted Carbazole Derivatives: A Review," *Molecules* 2015, 20, 13496.
Caruso et al., "Carbazole Derivatives: A Promising Scenario for Breast Cancer Treatment," *Molecules* 2008, 13, 1312.
Caruso et al., "Efficient and Simple Synthesis of 6-Aryl-1,4-dimethyl-9H-carbazoles," *Molecules*, 2008, 13, 1312-1320.
Castillo-Pichardo et al., "The Rac Inhibitor EHop-016 Inhibits Mammary Tumor Growth and Metastasis in a Nude Mouse Model," *Transl. Oncol.* 2014, 7, 546.
Chakrabarty et al., "A clay-mediated, regioselective synthesis of 2-(aryl/alkyl)amino-thiazolo[4,5-c]carbazoles," *Tetrahedron Lett.* 2004, 45, 4955.
Cho et al., "MST3 promotes proliferation and tumorigenicity through the VAV2/Rac1 signal axis in breast cancer," Oncotarget, Mar. 22, 2016; 7(12):14586-604.
Danish et al., "A one-pot synthesis of 1,2, 4, 5-tetraazaspiro [5.5]-6, 7, 8, 9-tetrahydrocarbazol-3-thiones and their antibacterial activities," *Indian J. Heterocycl. Chem.* 2006, 14, 19.
Dharmawardhane et al. "Development of EHop-016: A Small Molecule Inhibitor of Rac," Enzymes. 2013;33 Pt A:117-46.
Głuszyńska, "Biological potential of carbazole derivatives." *Eur. J. Med. Chem.* 2015, 94, 405.
Guillonneau et al., "Synthesis of 9-O-Substituted Derivatives of 9-Hydroxy-5,6-dimethyl-6H-pyrido[4,3-b]carbazole-1-carboxylic Acid (2-(Dimethylamino)ethyl)amide and Their 10-and 11-Methyl Analogues with Improved Antitumor Activity," *J. Med. Chem.* 1999, 42, 2191.
Guo et al., "A Novel Pharmacologic Activity of Ketorolac for Therapeutic Benefit in Ovarian Cancer Patients," *Clin Cancer Res* 2015 21, 5064-5072.
Hall, "Rho family GTPases," *Biochem. Soc. Trans.* 2005, 33, 891.
Hernandez et al., "Novel inhibitors of Rac1 in metastatic breast cancer," *P. R. Health Sci. J.* 2010, 29, 348-356.
Humphries-Bickley et al., "Pharmacokinetics of Rac Inhibitor EHop-016 in Mice by Ultra-Performance Liquid Chromatography Tandem Mass Spectrometry," Analyt Technol Biomed Life Sci. Feb. 15, 2015;981-982:19-26.
Humphries-Bickley et al., "Characterization of a Dual Rac/Cdc42 Inhibitor MBQ-167 in Metastatic Cancer," Molecular Cancer Therapeutics, p. 805-818 (2018).
Hunter et al., "Mechanisms of metastasis," J. Breast Cancer Research: *BCR.* 2008, 10(Suppl 1):S2.
Indumati et al., "Synthesis of 2-amino-8-chloro-4-phenyl-5,11-dihydro-6H-pyrido[2,3-a]carbazole-3-carbonitrile: Structural and biological evaluation," *J. Mol. Struct.* 2012, 1016, 134.
Issa et al., "Synthesis and antiproliferative activity of oxazinocarbazole and N,N-bis (carbazolylmethyl)amine derivatives," *Eur. J. Med. Chem.* 2010, 45, 2567.
Kantevari et al., "Synthesis and antitubercular evaluation of novel dibenzo[b,d]furan and 9-methyl-9H-carbazole derived hexahydro-2H-pyrano[3,2-c]quinolones via Povarov reaction," *Eur. J. Med. Chem.* 2011, 46, 4827.
Liang et al., "In vitro scratch assay: a convenient and inexpensive method for analysis of cell migration in vitro," *Nature Protoc.* 2007, 2, 329.
Liu et al., "Biological evaluation of 9-[(6-chloropyridin-4-yl)methyl]-9H-carbazole-3-carbinol as an anticancer agent," *Oncol. Rep.*, 2013, 29, 1501.
Maes et al., BNIP3 supports melanoma cell migration and vasculogenic mimicry by orchestrating the actin cytoskeleton. *Cell Death.* 2014 Dis. 5, e1127.
Maldonado MDM et al., Targeting Rac and Cdc42 GTPases in cancer, *Cancer Res.* Jun. 15, 2018;78(12):3101-3111.
Manes et al., TCR-driven transendothelial migration of human effector memory CD4 T cells involves Vav, Rac, and myosin IIA. *J Immunol.* 2013, 190, 3079-3088.
Martin et al., "Pak and Rac GTPases promote oncogenic KIT-induced neoplasms," J Clin Invest. Oct. 2013;123(10):4449-63.
Martinez-Viturro et al., "Synthesis of aza analogues of the anticancer agent batracylin," Tetrahedron Letters, 48(27): 4707-4710 (2007).
Montalvo-Ortiz et al., "Characterization of EHop-016, Novel Small Molecule Inhibitor of Rac GTPase," *J. Biol. Chem.* 2012, 287, 13228.
Peotter et al., "Involvement of Tiam1, RhoG and ELMO2/ILK in Rac1-mediated Phagocytosis in Human Trabecular Meshwork Cells," Exp Cell Res. Oct. 1, 2016;347(2):301-11.
Sayyad et al., "The Role of Rac1 in the Growth Cone Dynamics and Force Generation of DRG Neurons," PLoS One. Jan. 14, 2016;11(1):e0146842.
Sidarala et al., Biochem Pharmacol. 2015, 95(4):301-10.
Vega et al., "Rho GTPases in cancer cell biology," *FEBS Lett.* 2008, 582, 2093.
Veluthakal et al., "VAV2, a guanine nucleotide exchange factor for Rac1, regulates glucose-stimulated insulin secretion in pancreatic beta cells," Diabetologia. 2015 11:2573-81.
Vlaar et al., "Design, synthesis and biological evaluation of new carbazole derivatives as anti-cancer and anti-migratory agents," Bioorganic & Medicinal Chemistry, 26(4): 884-890 (2018).

(56) References Cited

OTHER PUBLICATIONS

Wang et al., "N-(2,6-Dimethoxypyridine-3-yl)-9-Methylcarbazole-3-Sulfonamide as a NovelTubulin Ligand against Human Cancer," *Clin. Cancer Res.* 2008, 14, 6218.
Yoon et al., "A novel carbazole derivative,MHY407,sensitizes cancer cells to doxorubicin-,etoposide-,and radiation treatment via DNA damage," Eur. J. Pharmacol. 2012, 697, 24.
U.S. Appl. No. 16/168,612, filed Oct. 23, 2018.

\* cited by examiner

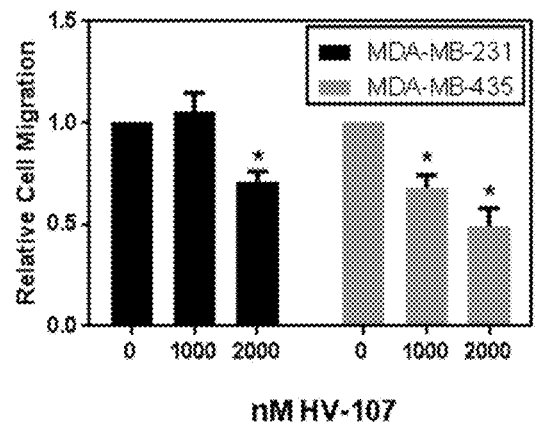
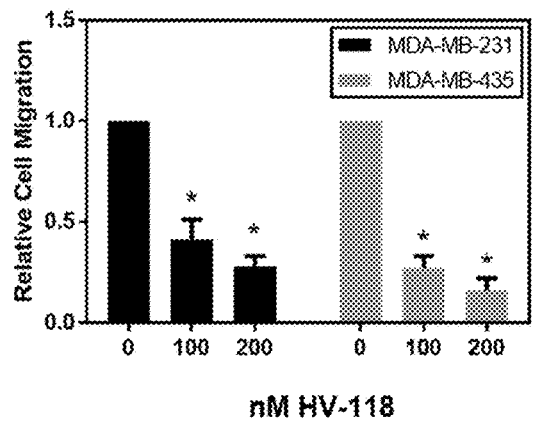
FIG. 17A
FIG. 17B
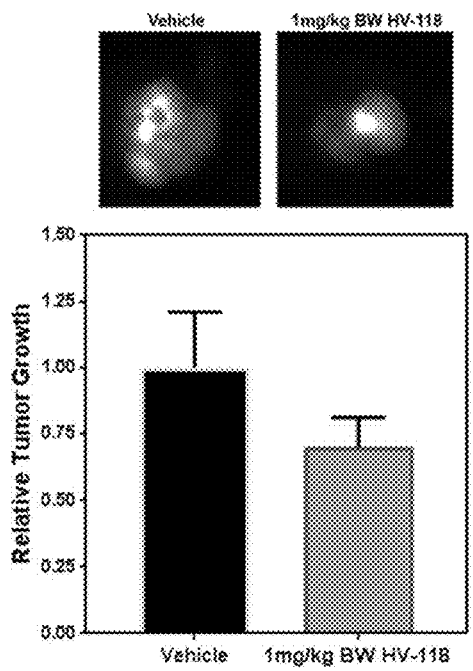
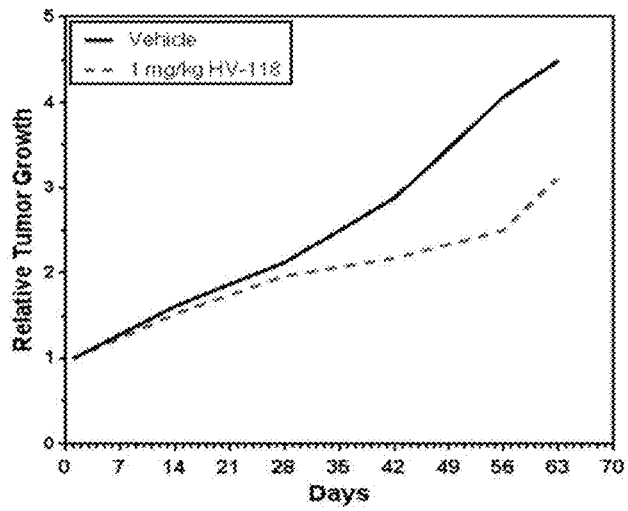
FIG. 18A
FIG. 18B

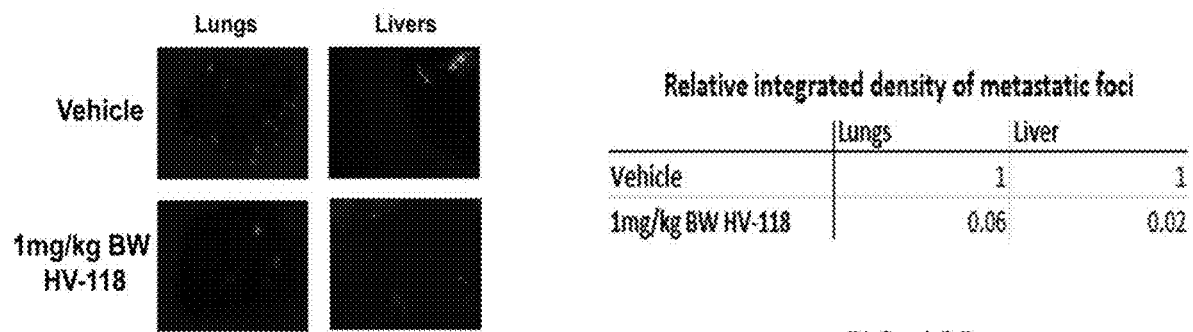
FIG. 18C
FIG. 18D
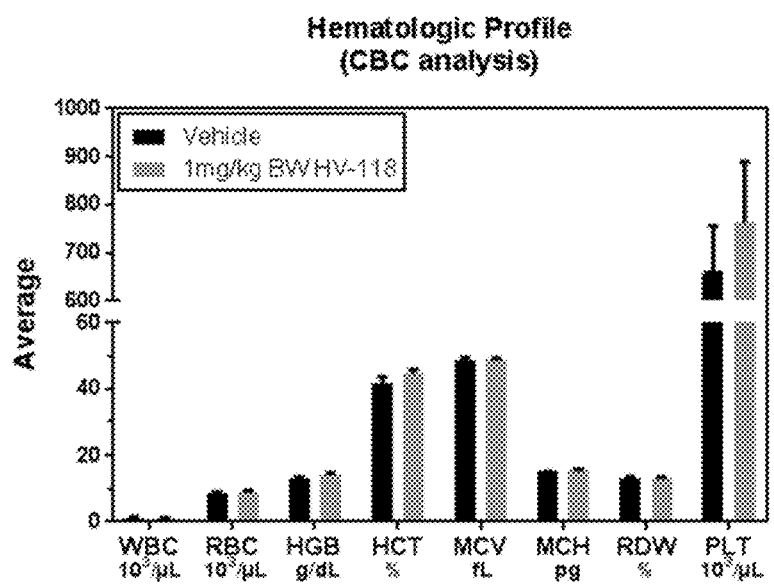
FIG. 19A

CARBAZOLE EHOP-016 DERIVATIVES AS ANTICANCER AND ANTI-MIGRATORY AGENTS

CROSS REFERENCE TO RELATED APPLICATIONS

This application is a Continuation of U.S. patent application Ser. No. 16/168,612, filed Oct. 23, 2018, which claims the benefit of priority under 35 U.S.C. § 119(e) to U.S. Provisional Patent Application No. 62/577,305, filed Oct. 26, 2017. The disclosures set forth in the reference applications are incorporated herein by reference in their entireties.

This invention was made with Government support under Award Nos. NIH-NIGMS P20GM103475-13 and NIH-NIGMS SC3GM116713 awarded by The National Institutes of Health. The U.S. Government has certain rights in the invention.

BACKGROUND

Many compounds are disclosed that inhibit Rho GTPases that are useful for inhibiting hyperprofilerative and neoplastic diseases. Specifically, the compounds inhibit the GTPases Rac and Cdc42 that are overactive or overexpressed in signaling pathways in cancer and metastasis. Methods for treatment of cancer and hyperproliferative diseases are disclosed.

The Rho GTPases Rac (Ras-related C3 botulinum toxin substrate) and Cdc42 (cell division control protein 42 homolog) regulate cell functions governing cancer malignancy, including cell polarity, migration, and cell cycle progression. The Rho family of GTPases in humans consists of 20 different members, and aberrant behavior in their regulatory activity has been implicated in cancer and other diseases. More than 70 Guanine nucleotide Exchange Factors (GEFs) are known, which specifically activate one or more of the GTPases. In turn, the activated GTPases can specifically interact with over 60 downstream effectors. Dysregulation of one or more cellular processes can lead to release of malignant cells from their original locations, which subsequently can establish themselves in pre-metastatic niches in, for example, bone or lungs. It has been found that members of the Rho GTPase family, including Rac, Cdc42 and Rho, play key signaling roles in these processes.

Rho GTPases regulate migration and invasion, cytoskeletal organization, transcriptional regulation, cell cycle progression, apoptosis, vesicle trafficking, and cell-to-cell and cell-to-extracellular matrix adhesions. The Rho GTPases Rac and Cdc42 are potent inducers of actin polymerization and extension of actin structures at the leading edge of motile cells. In addition, Cdc42 plays a critical role in cell polarity, and thus, promotes directed and persistent migration.

Studies have implicated hyperactive Rac and Cdc42 with increased cancer cell survival, proliferation, and invasion, as well in Ras and other oncogene-mediated transformation. Furthermore, oncogenic cell surface receptors, such as tyrosine kinase, cytokine, and G protein coupled receptors, activate Rac and Cdc42 via regulation of their upstream effector GEFs. Accordingly, Rae and Cdc42 proteins are generally not mutated in cancer but rather overexpressed or hyperactivated. Even though ~9% of melanomas contain an activating Rac(P29S) mutation, and the hyperactive splice variant Rac1b is overexpressed in some cancers, a majority of the Rac and Cdc42 in human cancer are activated due to upregulated GEFs.

Of the direct downstream effectors of Rae and Cdc42, p21-activated kinases (PAK) are overexpressed in a number of cancers and contribute to cancer transformation and progression by regulating key cellular functions, including cytoskeletal organization, cell migration, adhesion, growth, and development. Therefore, a number of PAK inhibitors have been developed as anti-cancer therapeutics. However, these have been limited by specificity, bioavailability, and toxicity, and have yet to successfully complete clinical trials.

In cancer patients, the ability of tumor cells to spread from primary tumors (and metastatic tumors) is the major cause of death. In the case that breast cancer is detected and treated prior to metastasis, the patient has higher probability of being cured of their disease. To successfully invade a secondary site, a cancer cell must complete a series of steps including separation from primary tumor (intravasation), invasion through surrounding tissues and basement membranes, entry and survival in the circulation, and arrest in a distant target organ (extravasation). During cancer cell invasion, tumor cell migration through tissues, frequently requires the degradation of the extracellular matrix (ECM) and several proteins play a key role in this process. Moreover, invadopodia are actin-rich protrusive structures with associated matrix degradation activity and are believed to be important for tumor cells to penetrate the basement membrane of epithelia and blood vessels. The small GTPase Rac1, a member of the Ras superfamily of GTPases has been implicated in regulating migration and invasion of breast cancer cells. Rac1 is activated by GTP/GDP exchange factors (GEF) that are regulated via a myriad of cell surface receptors. Therefore, therapeutic strategies targeting the binding of Rac1 to GEFs are a rational means to inhibit migration of cancer cells.

The carbazole skeleton contained in many synthetic and natural compounds is the key structural motif of many biological activities that are related to this type of molecules.

Many carbazole derivatives are well known for their various pharmacological activities such as antioxidant, anti-inflammatories, antibacterial, antitumor, anticonvulsant, antipsychotics, antidiabetics, and larvicidal properties. The cytotoxic activity of carbazole alkaloids has been related to their polycyclic, planar and aromatic structure. Some carbazole derivatives have been evaluated for their anti-tumor potential against several human tumor cell lines. The carbazole sulfonamide IG-105 is an antimitotic agent that inhibit microtubule assembly through specific interactions within tubulin structure. Modeling studies suggest that the dimethoxypyridine moiety and the carbazole group forms interactions with the hydrophobic pocket of tubulin, and that the sulfonamino group and the N atom of the carbazole forms hydrogen bonds. The HYL-6d derivative inhibits angiogenic proliferation and migration in HUVEC cells under pathological angiogenic conditions, which is critical in breast cancer progression and metastasis formation. The MHY407 is an epoxypropoxy carbazole derivative that effectively causes DNA damage by C-PARP production, topoisomerase II inhibition and cell cycle arrest at S phase by regulating cyclin Dl, pRb, and p21 levels.

EHop-016 has recently been developed and inhibits metastatic cancer cell viability at concentrations of >5 µM. Results showed that EHop-016 inhibits Rac1-Vav2 interaction with IC50=1 μM, Rac1 downstream effector PAK1 by ~60% at 2 μM, lamellipodia formation, and cell migration. EHop-016 and other compounds are described in PCT International Patent Application No. PCT/US2017/029921 (filed Apr. 27, 2017), which is herein incorporated by reference in its entirety.

There is a need for new therapeutic agents for the treatment of cancer and other hyperproliferative diseases. The Rac and Cdc42 GTPases are important cellular mediators that are hyperactive or overexpressed in metastatic tumors. Design of novel inhibitors of the activities of Rac and/or Cdc42 with improved activity, pharmacochemical profile and reduced toxicity is desirable.

SUMMARY

A summary of the results of characteristics of novel EHop-016 derivatives HV107 and HV118 is:

1. HV-107 and HV-118 are toxic to metastatic breast cancer cells MDA-MB-231 and MDA-MB-435 (but not non-cancerous cells);
2. HV-107 and HV-118 inhibit RAC;
3. HV-107 and HV-118 inhibit cell survival by promoting apoptosis (caspase 3 induction);
4. HV-107 and HV-118 promote cell survival signaling (inhibit Akt phosphorylation);
5. HV-107 and HV-118 inhibit cell migration;
6. HV-118 reduces tumor growth and metastasis to lung and liver in mice; and
7. HV-118 is not toxic to mice A series of novel of EHop-016 derivatives is presented herein via designing and synthesizing compounds that mimics its more favorable "U-shaped" conformation that appears to be critical for inhibitory activity against Rac. Based on modeling studies on EHop-016, compounds with a more rigid structural conformation can mimic this "U-shaped" conformation would improve the anti-migration activity against metastatic cells.

The present disclosure provides other more potent inhibitors of Rac compared to EHop-016. For instance, the first two series of compounds (3a-d and 4a-f, scheme 1; see FIG. 1) the replacement of the core pyrimidine group in EHop-016 with a pyridine, was explored which substitution at positions-2 and -3 with aliphatic amines and the carbazole group, respectively (or vice versa), place the key pharmacophores from EHop-016 in a more rigid 1,2-substitution sequence. Compounds 3a-d were synthesized by initial amide formation reacting 2-chloronicotinic acid 1 with carbazole 2, following by CuI-catalyzed coupling reaction with various amines to afford the corresponding 2-aminonicotinamide derivatives 3a-d. On the other hand, compounds 4a-f were synthesized by reacting 2-chloronicotinic acid 1 and carbazole 2 were under microwave irradiation at 140° C. for 5 h using 3 equiv. of DIPEA in water (scheme 1). The product 2-aminocarbazolenicotinic acid intermediate was reacted with various amines to afford the corresponding 2-aminocarbazole-nicotinamde derivatives. The growth inhibitory potency against MCF-7 and MDA-Mb-231 breast cancer cells was tested.

The following numbered embodiments are contemplated and are non-limiting:

1. A compound of formula (I),

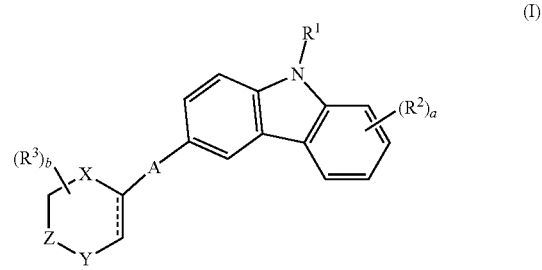

wherein $R^1$ is H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted;

each $R^2$ is independently deuterium, halogen, —OH, —CN, $C_1$-$C_6$ alkyl, $C_2$-$C_6$ alkenyl, $C_2$-$C_6$ alkynyl, $C_3$-$C_6$ cycloalkyl, $C_1$-$C_6$ to aryl, —$OR^5$, —$C(O)OR^5$, —$C(O)NR^5R^6$, —$NH_2$, —NH($C_1$-$C_6$ alkyl), —N($C_1$-$C_6$ alkyl)$_2$, —NHC(O)$C_1$-$C_6$ alkyl, —$CO_2H$, —C(O)$OC_1$-$C_6$ alkyl, —C(O)$NH_2$, —C(O)NH($C_1$-$C_6$ alkyl), —C(O)N($C_1$-$C_6$ alkyl)$_2$, —$SC_1$-$C_6$ alkyl, —S(O)$C_1$-$C_6$ alkyl, —$S(O)_2C_1$-$C_6$ alkyl, —S(O)NH($C_1$-$C_6$ alkyl), —$S(O)_2NH(C_1$-$C_6$ alkyl); wherein each hydrogen atom in $C_1$-$C_6$ alkyl, $C_2$-$C_6$ alkenyl, $C_2$-$C_6$ alkynyl, $C_3$-$C_6$ cycloalkyl, and $C_6C_{10}$ aryl is independently optionally substituted;

A is —O—, —S—, —N($R^7$)—, —N($R^7$)C(O)—, or —$C_1$-$C_6$ alkyl-, wherein each hydrogen atom in $C_1$-$C_6$ alkyl is optionally substituted;

the dashed bond is either present so that the bond is a double bond or absent so that the bond is a single bond;

X is =C($R^8$)—, =N—, —N=, or —C($R^8$)$_2$—, Y is =C($R^9$)—, =N—, —N=, or —C($R^9$)$_2$—, and Z is =C($R^1$)—, —C($R^{10}$)=, =N—, —N=, or —C($R^{10}$)$_2$—; provided that when X is =C($R^8$)— or =N—, Z is not =C($R^{10}$)— or —N—, when Y is =C($R^9$)— or =N—, Z is not =C($R^{10}$)— or —N—, each $R^3$ is independently deuterium, halo, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, $C_6$-$C_{10}$ aryl-($C_6$-$C_{10}$ aryl), $C_1$-$C_6$ alkyl-(NH$R^{11}$), $C_1$-$C_6$ alkyl-(O$R^{11}$), $C_6$-$C_{10}$ aryl-(O$R^{11}$), $C_1$-$C_6$ alkyl-(N$R^{11}R^{12}$), —NH$R^{11}$, —N$R^{11}R^{12}$, —O$R^{11}$, —C(O)$C_1$-$C_6$ alkyl, —C(O)$R^{11}$, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, $C_6$-$C_{10}$ aryl-($C_6$-$C_{10}$ aryl), $C_1$-$C_6$ alkyl-(NH$R^{11}$), $C_1$-$C_6$ alkyl-(O$R^{11}$), $C_6$-$C_{10}$ aryl-(O$R^{11}$), $C_1$-$C_6$ alkyl-, —C(O)$C_1$-$C_6$ alkyl, or mono- or bicyclic heteroaryl, is optionally substituted by deuterium, halogen, —OH, oxo, —O$R^{13}$, —NH$R^{13}$, —CN, —O$C_1$-$C_6$ alkyl, —$NH_2$, —NH($C_1$-$C_6$ alkyl), —NH($C_6$-$C_{10}$ aryl), —NH($C_6$-$C_{10}$ aryl)-N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)$NH_2$, —NHC(O)NH$C_1$-$C_6$ alkyl, —N($C_1$-$C_6$ alkyl)C(O)$NH_2$, —N($C_1$-$C_6$ alkyl)C(O)NH$C_1$-$C_6$ alkyl, —NHC(O)N($C_1$-$C_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)C$_1$-C$_6$ alkyl, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, C$_1$-C$_6$ alkyl-(3- to 7-membered heterocycloalkyl), —CF$_3$, —CHF$_2$, or —CH$_2$F;

each R$^5$, R$^6$, R$^7$, R$^8$, R$^9$, R$^{10}$, R$^{11}$, and R$^{12}$ is independently H, deuterium, C$_1$-C$_6$ alkyl, C$_2$-C$_6$ alkenyl, C$_2$-C$_6$ alkynyl, C$_3$-C$_6$ cycloalkyl, C$_1$-C$_6$ heteroalkyl, 3- to 7-membered heterocycloalkyl, C$_6$-C$_{10}$ aryl, C$_1$-C$_6$ alkyl-(3- to 7-membered heterocycloalkyl), heteroaryl, —OC$_1$-C$_6$ alkyl, —NHC$_1$-C$_6$ alkyl, —N(C$_1$-C$_6$ alkyl)$_2$, —S(O)$_2$C$_1$-C$_6$ alkyl, —CF$_3$, —CHF$_2$, or —CH$_2$F, wherein each hydrogen in C$_1$-C$_6$alkyl, C$_1$-C$_6$heteroalkyl, and C$_6$-C$_{10}$ aryl is optionally substituted by —O—C$_1$-C$_6$ alkyl, C$_3$-C$_6$ cycloalkyl, 3- to 7-membered heterocycloalkyl, 3- to 7-membered substituted heterocycloalkyl, —CH$_2$CN, —N(C$_1$-C$_6$ alkyl)$_2$, —OC$_1$-C$_6$ alkyl, optionally substituted aryl, —C(O)NH-optionally substituted aryl, hydroxy, or mono- or bicyclic heteroaryl; and a is 0, 1, 2, or 3, b is 0, 1, or 2, or a salt thereof.

2. The compound or a salt thereof of clause 1, wherein the compound is of the formula

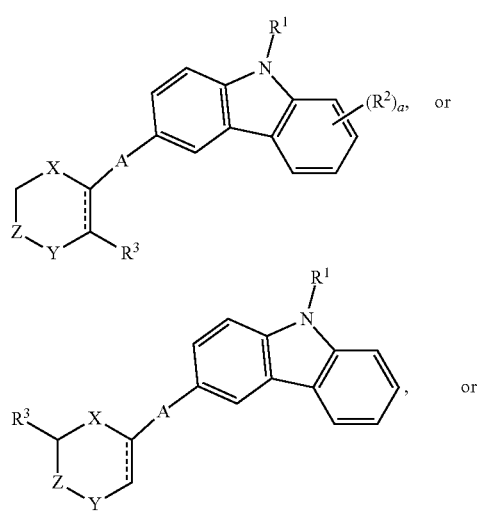

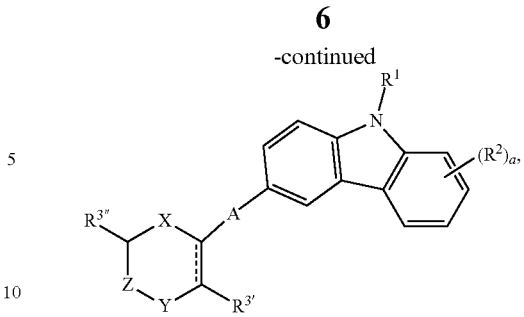

wherein each of R$^3$, R$^{3'}$, and R$^{3''}$ are as defined for R$^3$ above.

3. The compound or a salt thereof of clause 1 or clause 2, wherein the dashed bond is a double bond and X is =C(R$^8$)—, Y is =N—, and Z is —C(R$^{10}$)=; X is =N—, Y is =N—, and Z is —C(R$^{10}$)=; X is =N—, Y is =C(R$^9$)—, and Z is —N=; X is =N—, Y is =C(R$^9$)—, and Z is —C(R$^{10}$)=; or X is =N—, Y is =C(R$^9$)—, and Z is —C(R$^{10}$)=; or the dashed bond is absent and X is —C(Rx)$_2$-, Y is —C(R$^9$)$_2$—, and Z is —C(R$^{10}$)$_2$—;

wherein each R$^8$, R$^9$, and R$^{10}$ are each individually H, deuterium, halo, C$_1$-C$_6$ alkyl, C$_2$-C$_6$ alkenyl, C$_2$-C$_6$ alkynyl, C$_3$-C$_6$ cycloalkyl, 3-to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted.

4. The compound or a salt thereof of clause 1, wherein the compound has the structure

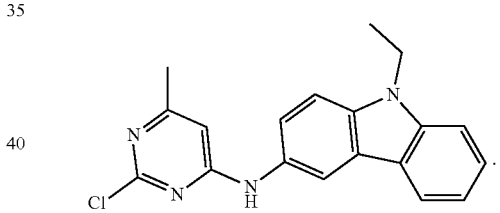

5. The compound or salt thereof of clause 2, wherein the compound has the structure

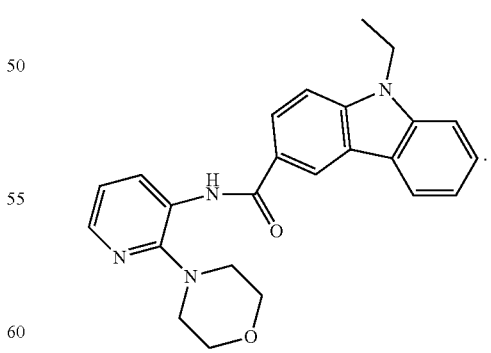

6. A method of treating a disease in a patient, the method comprising administering to the patient in need thereof an effective amount of a compound according to any one of clauses 1 to 5.

7. The method of clause 6, wherein the disease is cancer.

8. The method of clause 7, wherein the compound inhibits cancer cell migration.

9. The method of clause 7, wherein the cancer is selected from the group consisting of breast cancer, pancreatic cancer, ovarian cancer, gastric cancer, and neuronal cancer.

10. The method of clause 9, wherein the cancer is pancreatic cancer.

11. The method of clause 9, wherein the cancer is ovarian cancer.

12. The method of clause 9, wherein the cancer is gastric cancer.

13. The method of clause 9, wherein the cancer is neuronal cancer.

14. The method of clause 9, wherein the cancer is breast cancer.

15. The method of clause 14, wherein the compound inhibits mammosphere formation.

16. The method of any one of clauses 6 to 15, wherein the compound induces cell cycle arrest of a diseased cell.

17. The method of any one of clauses 6 to 16, wherein the compound induces apoptosis of a diseased cell.

18. The method of any one of clauses 6 to 17, wherein the compound reduces the expression of a Bcl-2 protein.

19. The method of any one of clauses 6 to 18, wherein the disease is mediated by a GTPase.

20. The method of clause 19, wherein the GTPase is Rac 1 or Cdc42.

21. The method of clause 20, wherein the GTPase is Rac1.

22. The method of clause 20, wherein the GTPase is Cdc42.

23. The method of any one of clauses 6 to 22, wherein the compound inhibits PAK1/2 activity.

24. The method of any one of clauses 6 to 23, wherein the compound inhibits STAT3 activity.

25. The method of any one of clauses 6 to 24, wherein the effective amount of the compound is in a range of about 0.01 mg/kg to about 100 mg/kg of body weight of the patient.

26. The method of any one of clauses 6 to 24, wherein the effective amount of the compound is in a range of about 0.1 mg/kg to about 50 mg/kg of body weight of the patient.

BRIEF DESCRIPTION OF THE DRAWINGS

FIG. 11 (A-B). Synthesis of EHop-016 derivatives with modifications in building block C.

FIG. 12 (A-B). Migration Assays for Compounds 5, 10, and 11 compared to EHop-016. Migration assays were performed via the Scratch Method.

FIG. 15 A, C. MDA-MB-231 and FIG. 15 B, D. MDA-MB-435 human metastatic breast cancer cells were treated for 48 or 72 h with 0, 500 or 1000 nM HV-107, 100 or 200 nM HV-118. Caspase 3/7 activity was measured using the Caspase-Glo 3/7 Assay (Promega, Corp.) as per manufacturer's instruction. N=4: error bars represent ±SEM; * p≤0.05.

FIG. 16 A, C. MDA-MB-231 and FIG. 16 B, D. MDA-MB-435 human metastatic breast cancer cells were treated for 24 h with 0, 250, 500 or 1000 nM HV-107, 100 or 200 nM HV-118. After treatment, total protein was extracted, and equal amounts of proteins were western blotted for total and phosphorylated Akt (pAkt). Positive bands were quantified using image J. N=4-6; error bars represent t SEM; * p≤0.05.

FIG. 17 (A-B). Effect of HV-107 and HV-118 on cell migration. Wounds were created on confluent monolayers of MDA-MB-231 or MDA-MB-435 human metastatic breast cancer cells. Immediately after, cells were treated for 24 h with FIG. 17A. 0, 1000, or 2000 nM of HV-107; and FIG. 17B. 0, 100, or 200 nM HV-118. The distance traveled by HV-107 and HV-118 treated cells that migrated to close the wound was quantified relative to the distance traveled by control-treated cells. N=4-7; error bars represent ±SEM; * p≤0.05.

FIG. 18 (A-D). Effect of HV-118 on mammary tumor growth. Severe combined immune deficiency (SCID) mice were inoculated at the mammary fat pad with GFP-MDA-MB-231 cells and treated with 0 (Vehicle) or 1 mg/kg BW HV-118 (5× a wk). FIG. 18A. Upper panel, representative images and lower panel, average relative tumor growth on last day. FIG. 18B. Relative tumor growth as a function of days following HV-118 administration. Lungs and livers were removed at necropsy and imaged for fluorescent metastatic foci. FIG. 18C. Representative organs under fluorescence microscopy for 0 (Vehicle) and 1 mg/kg BW HV-118 treatment. FIG. 18D. Relative average integrated intensity of fluorescent metastatic foci/organ/treatment. N=13-15 mice/group; error bars represent ±SEM.

DETAILED DESCRIPTION

Figure 1:
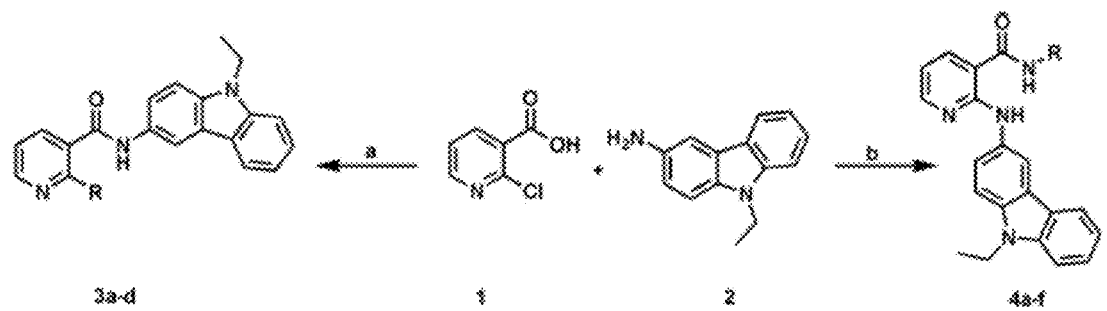
FIG. 1. Design and synthesis "Scheme 1". General synthetic routes of 2-substituted-nicotinamide derivatives 3a-d and 4a-f. Reagents and conditions: (a) (i) HOBt, ED AC, DMF, EtsN, rt; (h) CuI, DIPEA, dioxane, 80° C., 8-10 h, R=HNR$^1$R$^2$; (b) Method A (1) DIPEA (3 equiv), water, 140° C., 5 h, (n) HOBt, ED AC, DMF, EtsN, rt, R—NH$_2$. Method B (1) HOBt, ED AC, CH$_2$C$_{12}$, EtsN, rt; (11) CuI, CS$_2$CO$_3$, DMSO, 90° C., 24 h, R—NH$_2$.
Figure 2:
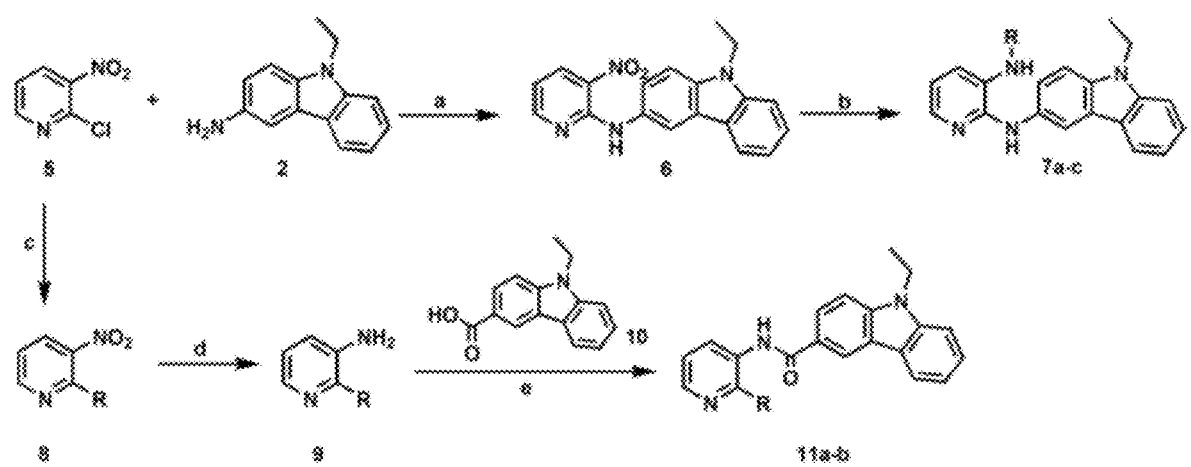
FIG. 2. Design and synthesis "Scheme 2". General synthetic routes to 2,3-diamino-substituted pyridines 7a-c and 11a-b. Reagents and conditions: (a) THF, Et3N, reflux, 2 h; (b) (i) SnCk, HCl, EtOH, reflux, (ii) HOBt, EDAC, DMF, EtsN, rt (for 7a) or THF, EtsN, reflux (for 7b-c); (c) R=HNR$^1$R$^2$, THF, EtsN, reflux; (d) SnCk, HCl, EtOH, reflux; (e) 10, HOBt, EDAC, DMF, EtsN, rt (for 11a-b).
Figure 3:
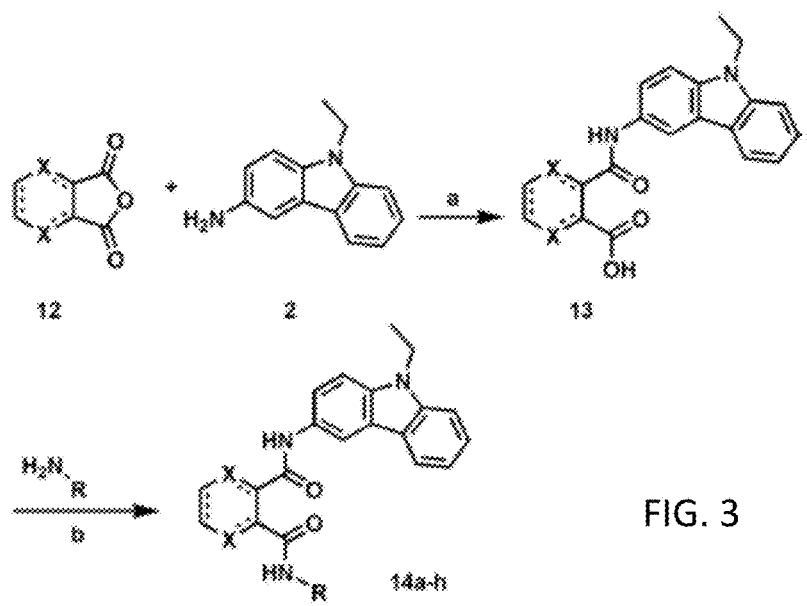
FIG. 3. Design and synthesis "Scheme 3". General synthetic route to ortho-diamide derivatives 14a-h. Reagents and conditions: (a) THF, rt 16 h; (b) HOBt, EDC, THF, rt, 16 h.

The present disclosure provides novel Ehop-016 derivatives and assesses their efficacy to inhibit Rac activation and selectively inhibit metastatic breast cancer cell viability.

Novel Rac Inhibitors as Targeted Therapy for Metastatic Breast Cancer

Effective therapeutics for metastatic breast cancer are disclosed by targeting the Rho GTPase Rac. Metastatic disease is the primary cause of breast cancer mortality, but effective treatments remain elusive. Therefore, there is a critical need to develop efficient strategies to inhibit metastatic breast cancer. The Rho GTPase Rac is a key molecular switch activated by a myriad of cell surface receptors to promote cancer cell migration/invasion, proliferation, and survival. Metastatic breast cancers often overexpress or exhibit high Rac activity. Therefore, the rationale for the proposed research is that inhibition of the interaction of Rac with their upstream effectors, guanine nucleotide exchange factors (GEFs), will impede cancer progression.

EHop-016 is a small molecule that inhibits Rac activity of metastatic breast cancer cells with an IC50 of 1 µM. EHop-016 is 10-100 times more active than previously available Rac inhibitors, and is the first compound shown to inhibit the activation of Rac by the oncogenic GEF Vav. EHop-016 inhibits the activity of the Rac downstream effector p21 activated kinase (PAK), extension of actin structures, and cell migration of metastatic breast cancer cells. At higher concentrations (≥10 µM) EHop-016 also inhibits cell viability and the related protein Cdc42 activity. EHop-016 at ≥25 mg/kg Body Weight (BW) significantly reduced tumor growth, metastasis, and angiogenesis in a mouse model. Moreover, the utility of EHop-016 as a Rac inhibitor has been shown in vitro and in vivo in a range of cancer types such as leukemia, prostate cancer, and melanoma. In addition to affecting cancer cells, EHop-016 may also inhibit the tumor promoting immune cells in the tumor microenvironment. However, pharmacokinetic study of EHop-016 in a mouse model demonstrated that EHop-016 was cleared rapidly from the circulation and that the bioavailability of this inhibitor needs to be improved for further pharmacological development. A panel of Ehop-016 derivatives was developed and tested. HV-107 inhibits Rac activation by 50% at 250 nM in breast cancer cells. Moreover, HV-107 inhibits breast cancer cell viability by 45% and is not toxic to non-cancerous mammary epithelial cells at concentrations ≥1 µM.

To demonstrate that HV-107 will inhibit metastatic breast cancer progression more efficiently than Ehop-016, the molecular mechanisms of HV-107 in breast cancer cells was examined.

Elucidation of the Molecular Mechanisms of HV-107.

The experimental approach to identify the mechanism of action of HV-107 is to: 1) characterize the effects of HV-107 on Rac-regulated cell functions; and 2) determine the activation status of known downstream targets of Rac using MDA-MB-231 and MDA-MB-435 metastatic breast cancer cells.

HV-107 is as a novel chemical probe with increased potency against Rac.

Characterization of the Rac Inhibitor HV-118 as Targeted Therapy for Metastatic Breast Cancer A panel of Ehop-016 derivatives was tested. HV-118 inhibits Rac activation by 65% at 100 nM in breast cancer cells. Moreover, HV-118 inhibits breast cancer cell viability, while showing minimal toxicity towards non-cancerous mammary epithelial cells. Therefore, preliminary data suggest HV-118 could be up to 20 times more potent than EHop-016.

To demonstrate that HV-118 will inhibit metastatic breast cancer progression more efficiently than Ehop-016, the molecular mechanisms of HV-118 in breast cancer cells was examined, and its efficacy to inhibit cancer progression validated in a mouse model of metastatic breast cancer.

Elucidation of the Molecular Mechanisms of HV-118.

To identify the mechanism of action of HV-118: 1) the effects of HV-118 on Rac-regulated cell functions were characterized; and 2) the activation status of known downstream targets of Rac using MDA-MB-231 and MDA-MB-435 metastatic breast cancer cells was determined.

Validation of HV-118 as an Inhibitor of Metastatic Breast Cancer Progression In Vivo.

Preliminary data supporting HV-118 as a potent inhibitor of Rac activation in breast cancer cells was confirmed. The in vivo efficacy of HV-118 is identified by testing HV-118 in immunocompromised mice inoculated with green fluorescent protein (GFP)-tagged MDA-MB-231 cells. Tumor growth and metastasis were assessed by fluorescent imaging. HV-118 toxicity was also determined.

Definitions

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw Ultra 13.0 (Perkin Elmer).

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$. Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_5$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments, alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthylenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, including an all-carbon 5-member/6-member or 6-member/6-member fused bicyclic ring, or a multicyclic fused ring (a "fused" ring system means that each ring in the system shares an adjacent pair of carbon atoms with each other ring in the system) group, where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_9$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like. Illustrative examples of cycloalkyl groups shown in graphical representations include the following entities, in the form of properly bonded moieties:

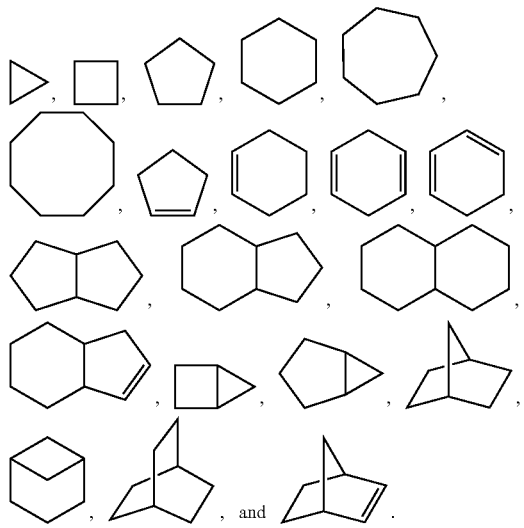

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3, 4-tetrahydropyridinyl, and the like. Illustrative examples of heterocycloalkyl groups shown in graphical representations include the following entities, in the form of properly bonded moieties:

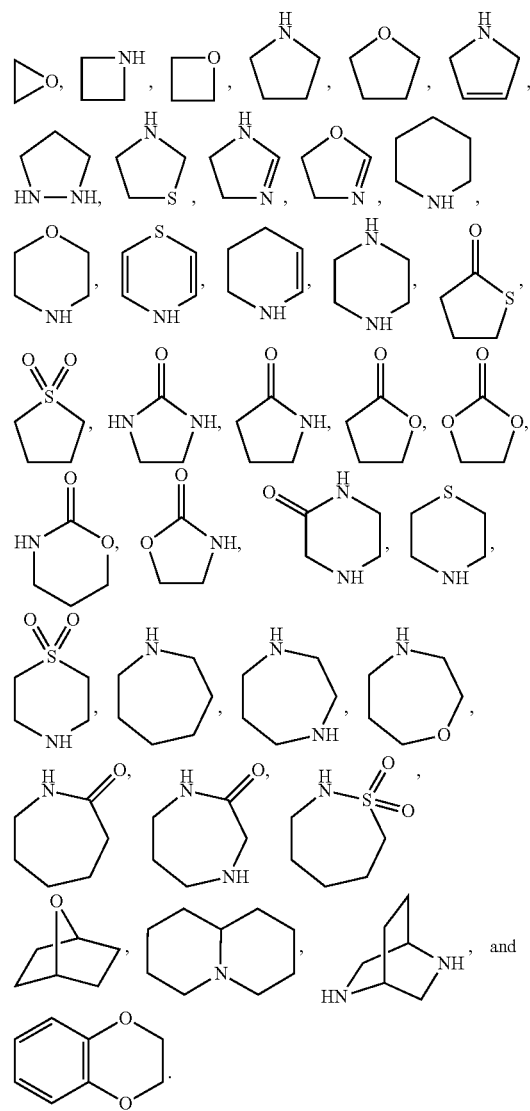

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like. Illustrative examples of heteroaryl groups shown in graphical representations, include the following entities, in the form of properly bonded moieties:

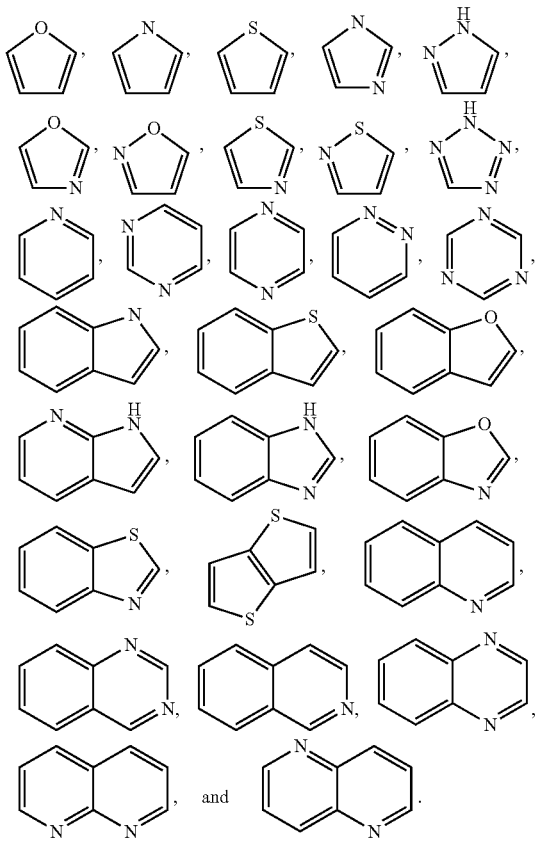

As used herein, "hydroxy" or ""hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group.

Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "cyano" refers to a —CN group.

The term "oxo" represents a carbonyl oxygen. For example, a cyclopentyl substituted with oxo is cyclopentanone.

As used herein, "bond" refers to a covalent bond.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_1$-$C_6$ alkyl, $C_2$-$C_6$ alkenyl, $C_2$-$C_6$ alkynyl, $C_3$-$C_6$ cycloalkyl, 3-to 7-membered heterocycloalkyl, $C_6$-$C_{10}$ aryl, or mono- or bicyclic heteroaryl is independently optionally substituted by $C_1$-$C_6$ alkyl" means that an alkyl may be but need not be present on any of the $C_1$-$C_6$ alkyl, $C_2$-$C_6$ alkenyl, $C_2$-$C_6$ alkynyl, $C_3$-$C_6$ cycloalkyl, 3-to 7-membered heterocycloalkyl, $C_6$-$C_{10}$ aryl, or mono- or bicyclic heteroaryl by replacement of a hydrogen atom for each alkyl group, and the description includes situations where the $C_1$-$C_6$ alkyl, $C_2$-$C_6$ alkenyl, $C_2$-$C_6$ alkynyl, $C_3$-$C_6$ cycloalkyl, 3-to 7-membered heterocycloalkyl, $C_6$-$C_{10}$ aryl, or mono- or bicyclic heteroaryl is substituted with an alkyl group and situations where the $C_1$-$C_6$ alkyl, $C_2$-$C_6$ alkenyl, $C_2$-$C_6$ alkynyl, $C_3$-$C_6$ cycloalkyl, 3-to 7-membered heterocycloalkyl, $C_6$-$C_{10}$ aryl, or mono- or bicyclic heteroaryl is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the term "pharmaceutically acceptable salt" refers to those salts which counter ions which may be used in pharmaceuticals. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The disclosure also relates to pharmaceutically acceptable prodrugs of the compounds and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound in accordance with the present disclosure). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof. For example, it will be appreciated that compounds depicted by a structural formula containing the symbol " ⁓ " include both stereoisomers for the carbon atom to which the symbol " ⁓ " is attached, specifically both the bonds " ▬ " and " ⫶⫶⫶ " are encompassed by the meaning of " ⁓ ".

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$ $^{36}Cl$, and $^{125}I$, respectively. Such isotopically labelled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

It should be understood that some of the ring structures described herein may be conjugated systems. Some of these conjugated systems may form aromatic rings. The graphical representations described herein should be understood as exemplary graphical representations of the possible other resonance structures or isomeric structures.

Example 1: Synthesis of Compounds

The synthesis of compounds according to the instant disclosure follows:

| Compound IDs From Instant Disclosure |
| --- |
| MBQ-1 (3a) |
| MBQ-2 (3b) |
| MBQ-3 (3c) |
| MBQ-4 (3d) |
| MBQ-5 |
| MBQ-6 (4a) |
| MBQ-7 (4b) |
| MBQ-8 (4c) |
| MBQ-9 (4d) |
| MBQ-10 (4e) |
| MBQ-11 (4f) |
| MBQ-12 (7a) |
| MBQ-13 (7b) |
| MBQ-14 (7c) |
| MBQ-15 (11a) |
| MBQ-16 (11b) |
| HV-107 |
| MBQ-17 (14a) |
| MBQ-18 (14b) |
| MBQ-19 (14c) |
| MBQ-20 (14d) |
| MBQ-21 (14f) |
| MBQ-22 (14e) |
| MBQ-23 (14g) |
| MBQ-24 (14h) |
| 29 |
| 32 |
| 33 |
| 34 |
| 35 |
| 36 |
| 37 |
| 38 |
| 39 |
| 40 |
| 41 |
| HV-118 |
| 8 |

General Remarks

All experiments were carried out in pre-dried glassware (≥1 h, 80-90° C.) under a nitrogen atmosphere. Nuclear magnetic resonance (NMR) spectra were obtained using a 400 MHz Bruker Avance UltraShield™ spectrometer. $^1$H (400 MHz) and $^{13}$C (100 MHz) NMR were recorded in CDCl$_3$ or DMSO-d$_6$, unless otherwise used, and the chemical shift were expressed in ppm relative to CDCl$_3$ (δ 7.26 for $^1$H and δ 77.0 for $^{13}$C) or DMSO-d$_6$ (δ 2.50 for $^1$H and δ 39.5 for $^{13}$C) as the internal standard. $^1$H NMR data is reported as position (δ), relative integral, multiplicity (s, singlet; d, doublet; t, triplet; q, quartet; dt, doublet of triplets; dd, doublet of doublets; dq, doublet of quartets; m, multiplet; br, broad peak), coupling constant (J, Hz), and the assignment of the atom. $^{13}$C NMR data are reported as position (δ) and assignment of the atom. Microwave reactions were conducted in a CEM Discovery Microwave for Drug Discovery, SP-1445.

Chemistry

Progress of the reaction was monitored via TLC analysis (General purpose silica gel on glass 5×20 cm with UV indicator, and visualized by UV fluorescent Spectroline E Series Ultraviolet lamps, in most cases followed by staining with I$_2$. The compounds were purified via column chromatography over silica gel (70-230 mesh, 60 Å) with the appropriate size column (24/40, 12 in.×0.5 in.) or (24/40, 12 in.×0.72 in.).

Synthesis of 2-substituted-nicotinamide Derivatives 3a-d

Synthesis of 2-chloro-N-(9-ethyl-9H-carbazol-3-yl)nicotinamide

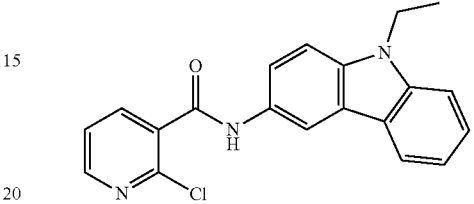

In a 50 mL three-neck round-bottom flask was charged 2-chloropyridine-3-carboxylic acid 1 (0.4726 g, 3.0 mmol), HOBT (0.4189 g, 3.1 mmol), EDAC (0.5943 g, 3.1 mmol). The solution was dissolved in DMF (5 mL) and 3-Amino-9-ethylcarbazole 2 (0.6308 g, 3.0 mmol) was added. After 15 min, Et$_3$N (0.859 mL, 6.0 mmol) was added and the mixture stirred at room temperature for 16 h. After completion of the reaction, water was added (30 mL) and the product was extracted using dichloromethane (30 mL). The organic layer was washed with brine and dried with Na$_2$SO$_4$, filtered and concentrated under reduced pressure. The crude oil was purified via column chromatography over silica gel and the product obtained as a white solid for the precursor 2-chloro-N-(9-ethyl-9H-carbazol-3-yl)nicotinamide (0.7565 g, 2.2 mmol, 73%). TLC analysis in CH$_2$Cl$_2$-MeOH (9:1). Rf=0.61. $^1$H NMR (400 MHz, CDCl$_3$) δ 1.46 (3H, t, J=7.3 Hz), 4.40 (2H, q, J=7.1 Hz), 7.43, (1H, t, J=8.6 Hz), 7.51 (11H, t, J=7.6 Hz), 7.64 (1H, d, J=2.3 Hz), 7.66 (1H, d, J=2.0 Hz), 8.13 (1H, d, J=7.3 Hz), 8.26 (1H, d, J=2.0 Hz), 8.28 (1H, d, J=1.8 Hz), 8.38 (1H, s), 8.47 (1H, d, J=1.8 Hz), 8.53 (1H, d, J=2.0 Hz), 8.54 (1H, d, J=2.0 Hz); $^{13}$C NMR (100 MHz, CDCl$_3$) 14.1, 38.0, 108.9, 113.6, 119.3, 121.1, 123.0, 123.2, 123.5, 126.4, 129.2, 132.0, 138.0, 140.3, 140.8, 147.4, 151.4, 162.9.

Synthesis of 2-(4-acetylpiperazin-1-yl)-N-(9-ethyl-9H-carbazol-3-yl)nicotinamide (3a)

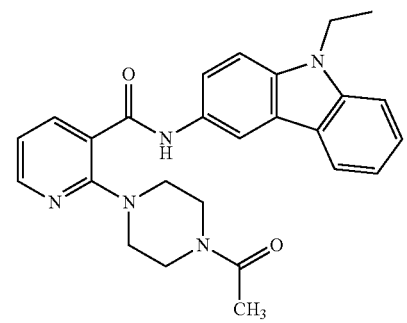 [SMILES: CCn1c2ccccc2c2cc(NC(=O)c3cccnc3N3CCN(C(C)=O)CC3)ccc21]

In a 50 mL three neck round bottom flask equipped with a reflux condenser was charged with 2-chloro-N-(9-ethyl- 9H-carbazol-3-yl)nicotinamide (0.1749 g, 0.5 mmol), DIPEA (0.52 mL, 3.0 mmol) and CuI (0.03 g, 0.16 mmol) in 5 mL of dioxane. After stirring for 5 min, 1-acetylpiperazine (0.077 g, 0.6 mmol) was added and the solution was heated at 80° C. for 8 h. After completion of the reaction, the mixture was allowed to reach room temperature, water was added (30 mL) and the product was extracted with dichloromethane (3×30 mL). The combined organic phases were washed with brine and dried over anhydrous $Na_2SO_4$, filtered and concentrated under reduced pressure. The crude oil product was purified via column chromatography over silica gel and the product 3a was obtained as a yellow solid (0.0506 g, 0.114 mmol, 23%). TLC analysis in $CH_2Cl_2$-MeOH (9:1), $R_f$=0.58. $^1$H NMR (400 MHz, CDCl$_3$) δ 1.25 (1H, t, J=7.2 Hz), 1.43 (3H, t, J=7.2 Hz), 2.09 (3H, s), 3.31 (4H, q, J=5.6 Hz), 3.64 (2H, t, J=5.2 Hz), 3.84 (2H, t, J=5.8 Hz), 4.12 (1H, q, J=7.2 Hz), 4.36 (2H, q, J=7.2 Hz), 7.22 (2H, m), 7.39 (2H, t, J=8.4 Hz), 7.47 (1H, t, J=8.0 Hz), 7.54 (1H, d, J=2.0 Hz), 7.56 (1H, d, J=1.6 Hz), 8.11 (1H, d, J=7.6), 8.43 (1H, t, J=2.0 Hz), 8.45 (1H, d, J=2.0 Hz), 8.63 (1H, d, J=1.6 Hz); $^{13}$C NMR (100 MHz, CDCl$_3$) δ 14.1, 21.3, 37.7, 41.5, 46.3, 51.5, 108.6, 108.8, 112.2, 118.5, 118.9, 120.1, 120.77, 122.4, 122.72, 123.4, 126.1, 129.8, 137.2, 140.4, 140.5, 150.0, 159.6, 163.1, 169.2.

Synthesis of N-(9-ethyl-9H-carbazol-3-yl)-2-morpholinonicotinamide (3b)

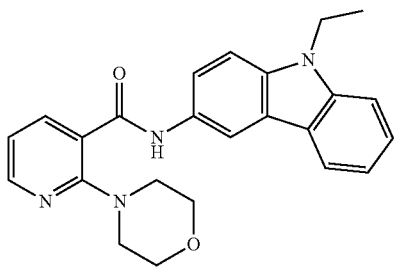 [SMILES: CCn1c2ccccc2c2cc(NC(=O)c3cccnc3N3CCOCC3)ccc21]

In a 50 mL three neck round bottom flask equipped with a reflux condenser was charged with 2-chloro-N-(9-ethyl-9H-carbazol-3-yl)nicotinamide (0.1749 g, 0.5 mmol), DIPEA (0.52 mL, 3.0 mmol) and CuI (0.03 g, 0.16 mmol) in 5 mL of dioxane. After stirring for 5 min, morpholine (0.052 mL, 0.6 mmol) was added and the solution was heated at 80° C. for 10 h. After completion of the reaction, the mixture was allowed to reach room temperature, water was added (30 mL) and the product was extracted with dichloromethane (3×30 mL). The combined organic phases were washed with brine and dried over anhydrous $Na_2SO_4$, filtered and concentrated under reduced pressure. The crude oil product was purified via column chromatography over silica gel and the product 3b was obtained as a white solid (0.0841 g, 0.21 mmol, 42%). TLC analysis in $CH_2Cl_2$-MeOH (9:1) $R_f$=0.79. $^1$H NMR (400 MHz, CDCl3) δ 1.46 (3H, t, J=7.2 Hz), 3.32 (4H, t, J=4.4 Hz), 3.95 (4H, t, J=4.4 Hz), 4.37 (2H, q, J=7.2 Hz), 7.24 (2H, m), 7.41 (1H, d, J=7.2 Hz), 7.48 (1H, t, J=7.2 Hz), 7.63 (1H, d, J=1.6 Hz), 7.66 (1H, d, J=1.6 Hz), 8.14 (1H, d, J=8.0 Hz), 8.46 (1H, d, J=4.4 Hz), 8.48 (1H, d, J=1.6 Hz), 8.67 (1H, s); $^{13}$C NMR (100 MHz, CDCl3) δ 14.1, 37.9, 52.1, 67.4, 108.8, 109.0, 112.3, 118.8, 119.1, 120.2, 121.0, 122.6, 123.0, 123.5, 126.3, 130.2, 137.4, 140.7, 140.7, 150.3, 160.2, 163.3.

Synthesis of N-(9-ethyl-9H-carbazol-3-yl)-2-(4-phenylpiperazin-1-yl)nicotinamide (3c)

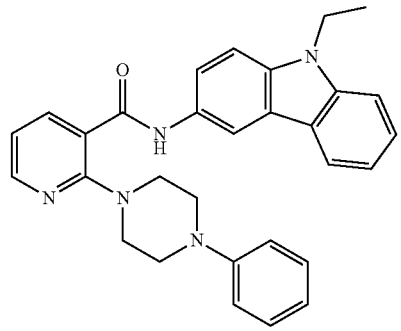 [SMILES: CCn1c2ccccc2c2cc(NC(=O)c3cccnc3N3CCN(c4ccccc4)CC3)ccc21]

In a 50 mL three neck round bottom flask equipped with a reflux condenser was charged with 2-chloro-N-(9-ethyl-9H-carbazol-3-yl)nicotinamide (0.1574 g, 0.45 mmol), DIPEA (0.52 mL, 3.0 mmol) and CuI (0.03 g, 0.16 mmol) in 5 mL of dioxane. After stirring for 5 min, 1-phenylpiperazine (0.070 mL, 0.46 mmol) was added and the solution was heated at 80° C. for 10 h. After completion of the reaction, the mixture was allowed to reach room temperature, water was added (30 mL) and the product was extracted with dichloromethane (3×30 mL). The combined organic phases were washed with brine and dried over anhydrous $Na_2SO_4$, filtered and concentrated under reduced pressure. The crude oil product was purified via column chromatography over silica gel and the product 3c was obtained as a brown solid (0.0476 g, 0.10 mmol, 22%). TLC analysis in $CH_2Cl_2$-MeOH (9:1) $R_f$=1.0. $^1$H NMR (400 MHz, CDCl$_3$) δ 1.43 (3H, t, J=7.2 Hz), 4.36 (2H, q, J=7.2 Hz), 7.29 (t, J=8.8 Hz), 7.39 (t, J=8.6 Hz), 7.47 (t, J=7.0 Hz), 7.54 (d, J=2.3 Hz), 7.56 (d, J=2.3 Hz), 8.09 (d, J=7.7 Hz), 8.47 (d, J=1.9 Hz), 8.49 (d, J=1.9), 8.51 (d, J=1.8 Hz), 8.52 (d, J=1.8 Hz), 8.73 (d, J=1.8 Hz); $^{13}$C NMR (100 MHz, CDCl$_3$) δ 13.8, 37.6, 49.7, 51.7, 108.5, 108.8, 112.2, 116.4, 118.5, 118.8, 120.0, 120.8, 122.5, 122.8, 123.3, 125.9, 129.3, 130.0, 137.1, 140.4, 140.5, 150.0, 163.1.

Synthesis of N-(9-ethyl-(H-carbazol-3-yl)-2-((3-morpholinopropyl)amino)nicotinamide (3d)

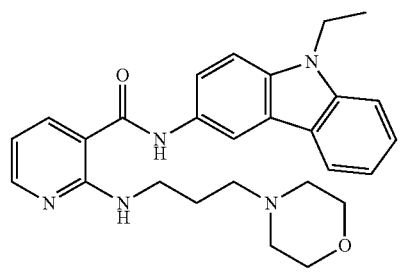 [SMILES: CCn1c2ccccc2c2cc(NC(=O)c3cccnc3NCCCN3CCOCC3)ccc21]

In a 50 mL three neck round bottom flask equipped with a reflux condenser was charged with 2-chloro-N-(9-ethyl-9H-carbazol-3-yl)nicotinamide (0.350 g, 1.00 mmol), DIPEA (0.52 mL, 3.0 mmol) and CuI (0.03 g, 0.16 mmol) in 5 mL of dioxane. After stirring for 5 min, 3-morpholinopropylamine (0.16 mL, 1.1 mmol) was added in one portion and the solution was heated at 80° C. for 10 h. After completion of the reaction, the mixture was allowed to reach room temperature, water was added (30 mL) and the product was extracted with dichloromethane (3×30 mL). The combined organic phases were washed with brine and dried over anhydrous $Na_2SO_4$, filtered and concentrated under reduced pressure. The crude oil product was purified via column chromatography over silica gel and the product 3d was obtained as a white solid (0.0985 g, 0.105 mmol, 11%). TLC analysis in $CH_2Cl_2$-MeOH (9:1), $R_f$=0.29. $^1$H NMR (400 MHz, $CDCl_3$) δ 1.44 (3H, t, J=7.2 Hz), 1.85 (2H, m), 2.47 (5H, t, J=7.2 Hz), 3.57 (2H, q, J=6.8 Hz), 3.72 (4H, t, J=4.6 Hz), 4.39 (2H, q, J=7.2 Hz), 6.56 (1H, q, J=5.1 Hz), 7.24 (1H, t, J=7.3 Hz), 7.41 (1H, d, J=5.8 Hz), 7.42 (1H, d, J=5.1 Hz), 7.48 (1H, t J=6.6 Hz), 7.53 (1H, d, J=1.8 Hz), 7.55 (1H, d, J=2.3 Hz), 7.76 (1H, d, J=2.0 Hz), 7.78 (1H, d, J=1.0 Hz), 7.84 (1H, s), 8.10 (1H, d, J=8.3 Hz), 8.27 (1H, d, J=2.3 Hz), 8.28 (1H, d, J=1.8 Hz), $^{13}$C NMR (100 MHz, $CDCl_3$) δ 13.8, 26.4, 37.6, 39.5, 53.8, 56.8, 66.9, 108.7, 110.4, 113.9, 118.9, 120.4, 120.7, 122.6, 123.2, 126.0, 129.0, 135.1, 137.6, 140.5, 157.1, 158.2, 166.9.

Synthesis of 2-substituted-nicotinamide Derivatives 4a-f

Synthesis of 2-(9-ethyl-9H-carbazol-3-ylamino)-N-(3-norpholinopropyl)nicotinamide (4a)

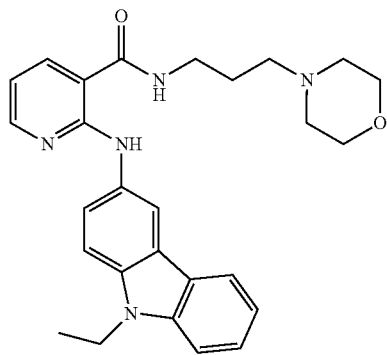 [SMILES: CCn1c2ccccc2c2cc(Nc3ncccc3C(=O)NCCCN3CCOCC3)ccc21]

Method A. Step (i) A microwave tube was charged with 2-chloronicotinic acid 1 (0.1576 g, 1.0 mmol), 9-ethyl-9H-carbazol-3-amine 2 (0.6318 g, 3.0 mmol), DIPEA (0.522 mL, 3.0 mmol), and water (1.5 mL). The solution was heated at 140° C. for 5 h under microwave conditions (Power level set to 200 W; Caution! Pressure may develop). After completion of the reaction, the mixture was allowed to cool to room temperature and transferred to a separatory funnel and diluted with dichloromethane (30 mL). The solution was washed with water (3×20 mL). The organic phase was separated and dried over anhydrous $Na_2SO_4$, filtered and concentrated under reduced pressure. The crude oil product was purified via column chromatography over silica gel and the product intermediate 2-((9-ethyl-9H-carbazol-3-yl) amino)nicotinic acid was obtained as a white solid (0.1286 g, 0.39 mmol, 39%). $^1$H NMR (400 MHz, $CDCl_3$) δ 1.32 (t, 3H, J=7.18 Hz), 4.44 (q, 2H, J=6.98 Hz), 6.81 (q, 1H, J=4.8 Hz), 7.17 (t, 1H, J=7.3 Hz), 7.44 (t, 1H, J=8.6 Hz), 7.58 (q, 2H, J=5.1 Hz), 7.66 (d, 1H, J=1.8 Hz), 7.68 (d, 1H, J=1.5 Hz), 8.13 (d, 1H, J=7.8 Hz), 8.23 (d, 1H, J=1.8 Hz), 8.25 (d, 1H, J=2.0 Hz), 8.35 (d, 1H, J=1.8 Hz), 8.38 (d, 1H, J=2.0 Hz), 8.42 (s, 1H), 10.37 (s, 1H); $^{13}$C NMR (100 MHz, $CDCl_3$) δ 13.7, 37.0, 106.8, 108.9, 109.0, 113.0, 113.1, 118.4, 120.4, 121.1, 122.1, 122.1, 125.2, 131.5, 136.1, 139.9, 140.4, 153.0, 156.4, 169.2. Step (ii) In a 50 mL three neck round bottom flask equipped with a reflux condenser was charged with 2-((9-ethyl-9H-carbazol-3-yl)amino)nicotinic acid (0.0634 g, 0.2 mmol), HOBt (0.0405 g, 0.2 mmol) and EDAC (0.0575 g, 0.3 mmol) in DMF (3 mL). To the solution was added 3-morpholinopropylamine (0.031 mL, 0.21 mmol). The solution is stirred at room temperature for 8 h until completed by TLC analysis. The reaction mixture is washed with water (10 mL) and extracted with ethyl acetate (3×20 mL). The combined organic phases are washed with brine and dried over anhydrous $Na_2SO_4$, filtered and concentrated under reduced pressure. The crude oil was purified via column chromatography over silica gel and the product 4a was obtained as a white solid (0.0458 g, 0.1 mmol, 50%). TLC analysis in $CH_2Cl_2$-MeOH (9:1), $R_f$=0.35. $^1$H NMR (400 MHz, $CDCl_3$) δ 1.43 (3H, t, J=7.6 Hz), 1.83 (3H, t, J=5.8 Hz), 2.54 (3H, s), 2.60 (2H, t, J=5.3 Hz), 3.60 (2H, q, J=5.8 Hz), 3.74 (4H, t, J=4.6 Hz), 4.37 (2H, q, J=7.3 Hz), 6.66 (1H, q, J=4.5 Hz), 7.19 (1H, t, J=7.8 Hz), 7.36 (1H, d, J=4.0 Hz), 7.39 (1H, d, J=3.5 Hz), 7.44 (1H, t, J=7.1 Hz), 7.69 (1H, d, J=1.5 Hz), 7.71 (1H, d, J=2.0 Hz), 7.74 (1H, d, J=1.5 Hz), 7.76 (1H, d, J=1.5 Hz), 8.08 (1H, d, J=7.8 Hz), 8.31 (1H, d, J=1.8 Hz), 8.32 (1H, d, J=1.7 Hz), 8.35 (1H, d, J=1.7 Hz), 10.53 (1H, s); $^{13}$C NMR (100 MHz, $CDCl_3$) δ 13.9, 23.65, 4.56, 40.9, 53.9, 59.0, 67.0, 108.4, 111.8, 113.7, 118.3, 120.6, 121.2, 125.40, 131.90, 135.4, 136.7, 140.4, 151.6, 156.3, 168.4.

Synthesis of tert-butyl 4-(2-(2-(9-ethyl-9H-carbazol-3-yl)amino)nicotinamido)ethyl)piperazine-1-carboxylate (4b)

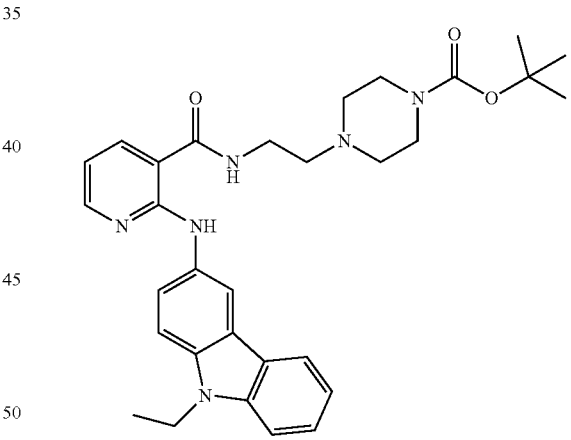

Method B. (i) In a 100 mL three-neck round-bottom flask was charged 2-chloronicotinic acid 1 (0.3151 g, 2.0 mmol), HOBt (0.4054 g, 3.0 mmol), and EDAC (0.5751 g, 3.0 mmol) were dissolved in $CH_2Cl_2$ (10 mL). After stirring for 10 min, 4-(2-aminoethyl)-1-boc-piperazine (0.4586 mL, 2.0 mmol) was added followed by $Et_3N$ (0.5733 mL, 4.0 mmol) and the reaction mixture stirred at room temperature for 16 h. After completion of the reaction, the solution was washed with water (30 mL), and the product was extracted with $CH_2Cl_2$ (3×20 mL). The combined organic phases were washed with brine, and dried over anhydrous $Na_2SO_4$, filtered, and concentrated under reduced pressure. The concentrated crude oil tert-butyl 4-(2-(2-chloronicotinamido) ethyl)piperazine-1-carboxylate intermediate was obtained (0.63 g, 1.71 mmol, 86%). The product was used in the next step without further purification. Step (ii) In a 100 mL three neck round bottom flask equipped with a stirring bar and reflux condenser, tert-butyl 4-(2-(2 chloronicotinamido) ethyl)piperazine-1-carboxylate (0.630 g, 1.71 mmol) and 9-ethyl-9H-carbazol-3-amine (0.0361 g, 1.72 mmol) were dissolved in 5 mL of DMSO. To the solution, CuI (0.0651 g, 0.3 mmol) and $Cs_2CO_3$ (1.11 g, 3.42 mmol) were added and heated at 90° C. for 24 hr. After the reaction was complete (analyzed by TLC), the mixture was allowed to reach room temperature. The mixture was washed with water (30 mL), and extracted with $CH_2Cl_2$ (3×30 mL). The combined organic phases were washed with brine and dried over anhydrous $Na_2SO_4$, filtered, and concentrated under reduced pressure. The crude oil was purified via column chromatography over silica gel and the product 4b was obtained as a white solid (0.08 g, 0.15 mmol, 9%). TLC analysis in $CH_2Cl_2$-MeOH (9:1), $R_f$=0.44. $^1$H NMR (400 MHz, $CDCl_3$) δ 1.26 (4H, t, J=7.1 Hz), 1.42 (3H, t, J=7.3 Hz), 1.46 (9H, s), 1.65 (3H, s), 2.04 (2H, s), 2.48 (3H, t, J=4.6 Hz), 2.65 (2H, t, J=5.9 Hz), 3.47 (4H, t, J=5.3 Hz), 3.56 (2H, q, J=5.6 Hz), 4.11 (1H, q, J=7.1 Hz), 4.34 (2H, q, J=7.6 Hz) 6.64 (1H, q, J=4.8 Hz), 7.19 (1H, t, J=6.3 Hz), 7.26 (1H, s,), 7.35 (1H, d, J=4.3 Hz), 7.39 (1H, d, J=3.8 Hz), 7.43 (1H, t, J=7.6 Hz), 7.65 (1H, d, J=1.8 Hz), 7.67 (1H, t, J=2.3 Hz), 7.69 (1H, d, J=2.0 Hz), 8.08 (1H, d, 7.6 Hz), 8.31 (1H, d, J=1.5 Hz), 8.32 (1H, d, J=1.8 Hz), 8.33 (1H, d, J=2.0 Hz), 10.40 (1H, s); $^{13}$C NMR (100 MHz, $CDCl_3$) δ 13.8, 37.5, 42.2, 44.8, 45.5, 66.6, 108.3, 112.8, 115.3, 118.3, 120.5, 120.7, 122.8, 123.2, 125.4, 131.6, 132.8, 136.5, 132.0, 140.3, 147.6, 167.8.

Synthesis of N-(3-(1H-imidazol-1-yl)propyl)-2-((9-ethyl-9H-carbazol-3-yl)amino)nicotinamide (4c)

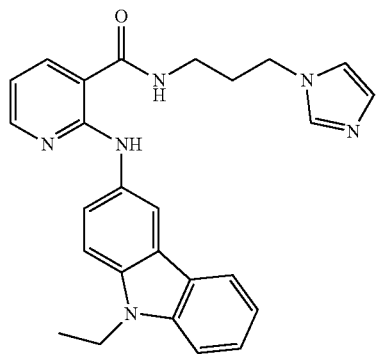 [SMILES: CCn1c2ccccc2c2cc(Nc3ncccc3C(=O)NCCCn3ccnc3)ccc21]

Method A. Step (i), the product intermediate 2-((9-ethyl-9H-carbazol-3-yl)amino)nicotinic acid was prepared as in procedure for compound 4a. Step (ii) In a 100 mL three-neck round-bottom flask was charged with 2-((9-ethyl-9H-carbazol-3-yl)amino)nicotinic acid (0.285 g, 0.9 mmol), HOBt (0.1351 g, 1.0 mmol), and EDAC (0.1917 g, 1.0 mmol) dissolved in $CH_2Cl_2$ (10 mL). To the solution, 1-(3-aminopropyl)imidazole (0.1190 mL, 1.0 mmol) was added. After 15 min of stirring, $Et_3N$ (0.286 mL, 2.0 mmol) was added and the reaction mixture was stirred at room temperature overnight. After the reaction was complete (analyzed by TLC), the mixture was washed with water (30 mL), and extracted with $CH_2Cl_2$ (3×20 mL). The combined organic phases were washed with brine and dried over anhydrous $Na_2SO_4$, filtered, and concentrated under reduced pressure. The crude was purified via column chromatography over silica gel and the product 4c was obtained as a white solid (0.0324 g, 0.074 mmol, 9%). TLC analysis in $CH_2Cl_2$-MeOH (9:1), $R_f$=0.50. $^1$H NMR (400 MHz, $CDCl_3$) δ 1.26 (4H, s), 1.42 (3H, t, J=7.2 Hz), 2.12 (5H, t, J=6.0 Hz), 3.44 (2H, q, J=6.8 Hz), 4.05 (2H, t, J=6.8 Hz), 4.35 (2H, q, J=7.2 Hz), 6.60 (1H, q, J=4.8 Hz), 6.93 (2H, s), 7.06 (1H, s), 7.16 (1H, t, J=3.2 Hz), 7.37 (1H, t, J=8.4 Hz), 7.40 (11H, t, J=8.8 Hz), 7.51 (1H, s), 7.67 (2H, t, J=8.8 Hz), 8.06 (1H, d, J=7.2 Hz), 8.28 (1H, d, J=4.4 Hz), 8.32 (1H, s), 10.36 (1H, s); $^{13}$C NMR (100 MHz, $CDCl_3$) δ 13.8, 29.7, 30.9, 37.2, 37.6, 44.8, 108.4, 110.1, 112.0, 113.9, 118.4, 118.9, 120.6, 121.4, 123.0, 123.1, 125.5, 129.5, 131.7, 135.6, 136.8, 137.1, 140.4, 151.8, 156.3, 168.5.

Synthesis of N-(4-Diethylamino-1-methyl-butyl)-2-(9-ethyl-9H-carbazol-3-ylamino)-nicotinamide (4d)

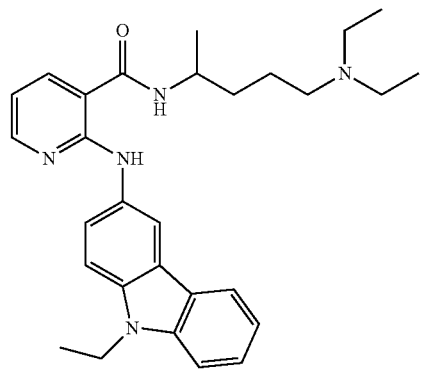 [SMILES: CCN(CC)CCCC(C)NC(=O)c1cccnc1Nc1ccc2c(c1)c1ccccc1n2CC]

Method A. Step (i), the product intermediate 2-((9-ethyl-9H-carbazol-3-yl)amino)nicotinic acid was prepared as in procedure for compound 4a. Step (ii) In a 100 mL three-neck round-bottom flask was charged with 2-((9-ethyl-9H-carbazol-3-yl)amino)nicotinic acid (0.9941 g, 3.0 mmol), HOBt (0.4054 g, 3.0 mmol), and EDAC (0.5751 g, 3.0 mmol) dissolved in $CH_2Cl_2$ (10 mL). After 15 min of stirring, 2-amino-5-diethylaminopentane (0.58 g, 3.0 mmol) was added followed by $Et_3N$ (0.43 mL, 3.0 mmol). The reaction mixture was stirred at room temperature for 16 h. After the reaction was complete (analysis by TLC), water (30 mL) was added, and the product extracted with $CH_2Cl_2$ (3×20 mL). The combined organic phases were washed with brine and dried over anhydrous $Na_2SO_4$, filtered, and concentrated under reduced pressure. The crude was purified via column chromatography over silica gel and the product 4c was obtained as a white solid (0.500 g, 1.0 mmol, 33.3%). TLC analysis in $CH_2Cl_2$-MeOH (9:1), $R_f$=0.42. $^1$H NMR (400 MHz, $CDCl_3$) δ 1.29 (10H, m), 1.42 (3H, t, J=7.2 Hz), 3.02 (4H, q, J=6.4 Hz), 4.38 (2H, q. J=7.2 Hz), 6.67 (1H, q, J=4.8 Hz), 7.16 (1H, t, J=6.8 Hz), 7.38 (2H, t, J=6.4 Hz), 7.46 (1H, t, J=8.4 Hz), 7.68 (1H, d, J=2.4 Hz), 7.71 (1H, d, J=2.0 Hz), 8.07 (1H, d, J=7.6 Hz), 8.12 (1H, d, J=7.2 Hz), 8.28 (1H, d, J=4.0 Hz), 8.32 (1H, d, J=1.6 Hz), 10.56 (1H, s); $^{13}$C NMR (100 MHz, $CDCl_3$) δ 9.0, 14.2, 21.8, 33.6, 37.9, 45.6, 47.2, 52.5, 108.7, 110.7, 112.7, 113.9, 118.7, 120.9, 121.5, 123.3, 125.7, 132.4, 136.9, 140.7, 151.8, 156.6, 168.7.

Synthesis of N-(2-(diethylamino)ethyl)-2-((9-ethyl-9H-carbazol-3-yl)amino)nicotinamide (4e)

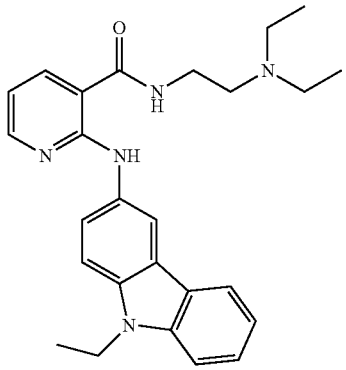 [SMILES: CCN(CC)CCNC(=O)c1cccnc1Nc1ccc2c(c1)c1ccccc1n2CC]

Method A. Step (i), the product intermediate 2-((9-ethyl-9H-carbazol-3-yl)amino)nicotinic acid was prepared as in procedure for compound 4a. Step (ii) In a 100 mL three-neck round-bottom flask was charged with 2-((9-ethyl-9H-carbazol-3-yl)amino)nicotinic acid (0.9941 g, 3.0 mmol), HOBt (0.4054 g, 3.0 mmol), and EDAC (0.5751 g, 3.0 mmol) dissolved in $CH_2Cl_2$ (10 mL). After 15 min of stirring, N,N-diethylethylenediamine (0.42 mL, 3.0 mmol) and $Et_3N$ (0.42 mL, 3.0 mmol) were added. The reaction mixture was stirred at room temperature for 16 h. After the reaction was complete (analysis by TLC), water (30 mL) was added, and the product extracted with $CH_2C_{12}$ (3×20 mL). The combined organic phases were washed with brine and dried over anhydrous $Na_2SO_4$, filtered, and concentrated under reduced pressure. The crude was purified via column chromatography over silica gel and the product (4e) was obtained as a white solid (0.7984 g, 1.8 mmol, 60%). TLC analysis in $CH_2Cl_2$-MeOH (9:1), $R_f$=0.67. $^1$H NMR (400 MHz, $CDCl_3$) δ 1.29 (3H, t, J=7.3 Hz), 1.42 (3H, t, J=7.3 Hz), 3.04 (q, J=6.8 Hz), 3.14 (t, J=5.0 Hz), 3.78 (q, J=5.56 Hz), 4.35 (q, J=7.1 Hz), 7.18 (t, J=7.6), 7.36 (d, J=4.8 Hz), 7.39 (d, J=3.8 Hz), 7.44 (t, J=7.1 Hz), 7.68 (d, J=2.0 Hz), 7.71 (d, J=2.78 Hz), 8.06 (d, J=7.6 Hz), 8.31 (d, J=1.8 Hz); $^{13}$C NMR (100 MHz, $CDCl_3$) δ 8.6, 13.5, 35.4, 37.2, 47.2, 51.6, 108.0, 108.0, 109.3, 112.1, 113.6, 118.0, 120.3, 121.1, 122.7, 122.8, 125.1, 131.6, 136.4, 140.0, 151.5, 156.1, 168.7.

Synthesis of 2-((9-ethyl-9H-carbazol-3-yl)amino)-N-(3,4,5-trimethoxyphenyl)nicotinamide (4f)

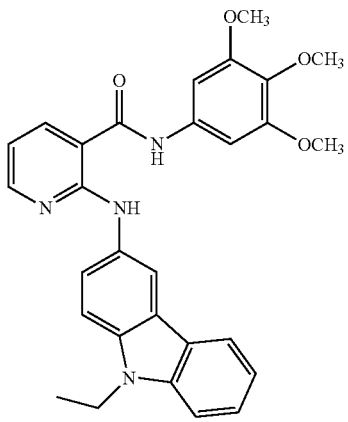 [SMILES: CCn1c2ccccc2c2cc(Nc3ncccc3C(=O)Nc3cc(OC)c(OC)c(OC)c3)ccc21]

Method B. Step (i) In a 100 mL three-neck round-bottom flask was charged 2-chloronicotinic acid 1 (0.1576 g, 1.0 mmol), HOBt (0.2027 g, 1.5 mmol), and EDAC (0.2876 g, 1.5 mmol) dissolved in $CH_2Cl_2$ (10 mL). The mixture was stirred for 10 min, then 3,4,5-trimethoxyaniline (0.1832 g, 1.0 mmol) and $Et_3N$ (0.3 mL, 2.0 mmol) were added. The mixture was stirred at room temperature for 16 h. After the reaction was complete (analyzed by TLC), the solution was washed with water (30 mL), and the product was extracted with $CH_2Cl_2$ (3×20 mL). The combined organic phases were washed with brine and dried over anhydrous $Na_2SO_4$, filtered, and concentrated under reduced pressure. The crude oil was purified via column chromatography over silica gel and the product 2-chloro-N-(3,4,5-trimethoxyphenyl)nicotinamide was obtained as a white solid (0.2828 g, 0.8762 mmol, 87.6%). TLC analysis in ethyl acetate-hexane (1:1), $R_f$=0.34. $^1$H NMR (400 MHz, $CDCl_3$) δ 3.88 (5H, s), 3.83 (3H, s), 6.94 (2H, s), 7.26 (1H, s), 7.39 (1H, q, J=4.76 Hz) 8.18 (1H, d, J=1.98 Hz), 8.50 (11H, d, J=1.97 Hz), 8.51 (1H, d, J=1.95 Hz); $^{13}$C NMR (100 MHz, $CDCl_3$) δ 14.66, 56.22, 60.98, 98.00, 122.97, 131.38, 133.38, 133.21, 135.51, 139.93, 146.92, 151.36, 153.51, 162.50. Step (ii) In a 100 mL three neck round bottom flask equipped with a stirring bar and reflux condenser, 2-chloro-N-(3,4,5-trimethoxyphenyl)nicotinamide (0.2828 g, 0.88 mmol) and 9-ethyl-9H-carbazol-3-amine 2 (0.1517 g, 0.7214 mmol) were dissolved in DMSO (3 mL). To the solution, CuI (40 mg, 0.21 mmol, 25%) and $Cs_2CO_3$ (1.0 g, 3.0 mmol) were added, and heated at 90° C. for 24 h. After the reaction was complete (analyzed by TLC), the mixture was allowed to reach room temperature. The mixture was washed with water (30 mL), and extracted with $CH_2Cl_2$ (3×30 mL). The combined organic phases were washed with brine and dried over anhydrous $Na_2SO_4$, filtered, and concentrated under reduced pressure. The crude oil was purified via column chromatography over silica gel and the product 4f was obtained as a white solid (0.0324 g, 0.0652 mmol, 8%). TLC analysis in ethyl acetate-hexane (1:1), $R_f$=0.35. $^1$H NMR (400 MHz, $CDCl_3$) δ 1.35 (10H, t, J=7.3 Hz), 1.49 (3H, t, J=7.6 Hz), 1.62 (7H, s), 2.08 (3H, s), 3.87 (8H, s), 4.17 (2H, q, J=7.3 Hz), 4.43 (1H, q, J=7.3 Hz), 5.51 (1H, s), 6.65 (1H, s), 6.95 (11H, q, J=4.6 Hz), 7.30 (1H, s), 7.47 (1H, d, J=8.3 Hz), 7.51 (2H, d, J=6.32 Hz), 8.09 (1H, d, J=9.4 Hz), 8.36 (1H, q, J=2.5 Hz), 8.41 (1H, d, J=2.0 Hz), 8.43 (1H, d, J=1.5 Hz); $^{13}$C NMR (100 MHz, $CDCl_3$) δ 13.9, 37.7, 56.3, 60.9, 68.4, 103.2, 108.7, 109.2, 112.9, 115.8, 117.7, 119.0, 120.6, 122.6, 123.7, 124.0, 126.1, 133.7, 136.0, 137.1, 138.2, 138.5, 140.5, 153.1, 153.6, 157.7, 163.0.

Synthesis of 2, 3-diamino-substituted Pyridine Derivatives 7a-c and 11a-b

Synthesis of (9-Ethyl-9H-carbazol-3-yl)-(3-nitro-pyridin-2-yl)-amine (6)

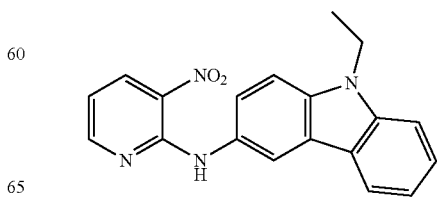

In a 100 mL three neck round bottom flask equipped with a stirring bar and reflux condenser, 2-chloro-3-nitropyridine 5 (0.31708 g, 2 mmol), 9-ethyl-9H-carbazol-3-amine 2 (0.42056 g, 2 mmol), and Et$_3$N (0.3582 mL, 2.5 mmol) were dissolved in THF (3 mL). The reaction mixture is refluxed for 2 h. After the reaction was complete (analyzed by TLC), the mixture was allowed to reach room temperature. The mixture was washed with water (30 mL), and extracted with ethyl acetate (3×30 mL). The combined organic phases were washed with brine and dried over anhydrous Na$_2$SO$_4$, filtered, and concentrated under reduced pressure. The crude was purified via column chromatography over silica gel and the product (9-Ethyl-9H-carbazol-3-yl)-(3-nitro-pyridin-2-yl)-amine 6 was obtained as a brown solid (0.16 g, 0.48 mmol, 24.1%). TLC analysis in CH$_2$C$_{12}$-MeOH (9:1), R$_f$=0.71. $^1$H NMR (400 MHz, DMSO-d$_6$) δ 1.34 (3H, t, J=7.1 Hz), 4.48 (2H, q, J=6.6 Hz), 6.94 (1H, q, J=4.4 Hz), 7.20 (1H, t, J=7.6 Hz), 7.47 (1H, t, J=7.2 Hz), 7.63 (2H, s), 8.15 (1H, d, J=8.0 Hz), 8.34 (s, 1H), 8.49 (1H, d, J=3.2 Hz), 8.57 (1H, d, J=8.4 Hz), 10.13 (1H, s); $^{13}$C NMR (100 MHz, DMSO-d$_6$) δ 14.2, 37.5, 109.4, 109.7, 114.2, 116.6, 119.2, 120.9, 122.5, 123.7, 126.3, 128.6, 130.3, 136.0, 137.6, 140.5, 151.1, 156.1.

Synthesis of N2-(9-Ethyl-9H-carbazol-3-yl)-pyridine-2,3-diamine (6a)

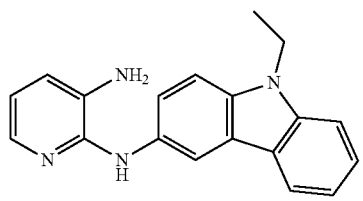 [SMILES: CCn1c2ccccc2c2cc(Nc3ncccc3N)ccc21]

In a 100 mL three neck round bottom flask equipped with a stirring bar and reflux condenser, 9-ethyl-N-(3-nitropyridin-2-yl)-9H-carbazol-3-amine 6 (0.16 g, 0.48 mmol) was dissolved in EtOH (25 mL) and water (25 mL). After stirring for 10 min, SnCl$_2$.2H$_2$O (0.27 mL, 1.44 mmol) and HCl (0.5 mL) were added, and the reaction mixture was refluxed for 5 h. After reaction completion (analysis by TLC), the mixture was allowed to reach room temperature and washed with 1M KOH. The layers were separated and the aqueous layer was further extracted with ethyl acetate (3×30 mL). The combined organic phases were washed with brine and dried over anhydrous Na$_2$SO$_4$, filtered and concentrated under reduced pressure. The crude oil product N$^2$-(9-Ethyl-9H-carbazol-3-yl)-pyridine-2,3-diamine 6a was utilized without further purification. TLC analysis in CH$_2$Cl$_2$-MeOH (9:1), R$_f$=0.43. $^1$H NMR (400 MHz, DMSO-d$_6$) δ 1.32 (3H, t, J=7.03 Hz), 4.40 (2H, q, J=6.97 Hz), 5.02 (2H, s), 6.56 (1H, dd, J=4.92, 7.22 Hz), 6.88 (1H, d, J=7.45 Hz), 7.14 (1H, t, J=7.40 Hz), 7.41 (1H, t, J=7.37 Hz), 7.49 (1H, d, J=8.19 Hz), 7.55 (1H, d, J=8.14 Hz), 7.66 (1H, d, J=12.57 Hz), 8.03 (1H, d, J=7.65 Hz), 8.36 (1H, s); $^{13}$C NMR (100 MHz, DMSO-d$_6$) δ 13.5, 36.7, 108.4, 108.7, 110.5, 114.4, 117.9, 118.8, 119.7, 119.8, 121.7, 122.0, 125.1, 130.1, 134.1, 134.3, 134.8, 139.6, 144.7.

Synthesis of N-[2-(9-Ethyl-9H-carbazol-3-ylamino)-pyridin-3-yl]-3-piperidin-1-yl-propionamide (7a)

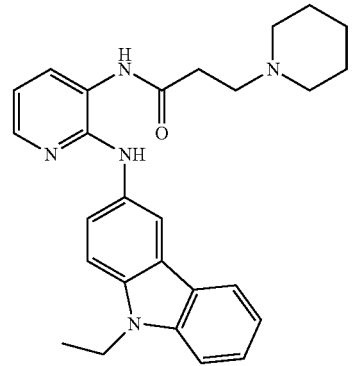 [SMILES: CCn1c2ccccc2c2cc(Nc3ncccc3NC(=O)CCN3CCCCC3)ccc21]

In a 100 mL three neck round bottom flask equipped with a stirring bar and reflux condenser, N$^2$-(9-ethyl-9H-carbazol-3-yl)pyridine-2,3-diamine 6a (0.160 g, 0.53 mmol), 1-piperidinepropionic acid (0.1570 g, 1.0 mmol), HOBt (0.2027 g, 1.5 mmol), and EDAC (0.2876 g, 1.5 mmol) dissolved in CH$_2$Cl$_2$ (10 mL). After stirring for 30 minutes, Et$_3$N (0.3 mL) was added and the reaction mixture stirred for 24 hr. After the reaction was complete (analyzed by TLC), the mixture was allowed to reach room temperature. The mixture was washed with water (30 mL), and extracted with CH$_2$Cl$_2$ (3×30 mL). The combined organic phases were washed with brine and dried over anhydrous Na$_2$SO$_4$, filtered, and concentrated under reduced pressure. The crude was purified via column chromatography over silica gel and the product 7a was obtained (0.1630 g, 0.37 mmol, 65%) as a yellow solid. TLC analysis in CH$_2$Cl$_2$-MeOH (9:1), R$_f$=0.53. $^1$H NMR (400 MHz, CDCl$_3$) δ 1.41 (3H, t, J=7.1 Hz), 1.67 (4H, t, J=6.1 Hz), 2.76 (2H, d, J=4.0 Hz), 2.85 (2H, d, J=4.6 Hz), 4.33 (2H, q, J=7.3 Hz), 6.75 (1H, q, J=5.1 Hz), 7.17 (1H, t, J=7.3 Hz), 7.35 (3H, t, J=9.1 Hz), 7.43 (1H, t, J=6.8 Hz), 7.53 (1H, d, J=8.1 Hz), 7.69 (1H, d, J=8.1 Hz), 8.05 (1H, d, J=10.3 Hz), 8.08 (1H, d, J=4.3 Hz); $^{13}$C NMR (400 MHz, CDCl$_3$) δ 13.9, 23.4, 25.1, 32.2, 37.6, 53.9, 54.3, 108.3, 108.5, 113.5, 114.5, 118.3, 120.6, 121.2, 122.9, 123.2, 125.4, 131.7, 132.6, 136.7, 140.3, 144.7, 150.5, 171.1.

Synthesis of N-(2-((9-ethyl-9H-carbazol-3-yl)amino)pyridin-3-yl)nicotinamide (7b)

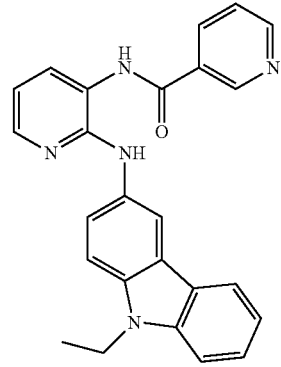 [SMILES: CCn1c2ccccc2c2cc(Nc3ncccc3NC(=O)c3cccnc3)ccc21]

Step (i) The $N^2$-(9-Ethyl-9H-carbazol-3-yl)-pyridine-2,3-diamine was prepared following procedure as in Step (i) 7a. Step (ii) In a 100 mL three neck round bottom flask equipped with a stirring bar and reflux condenser, $N^2$-(9-ethyl-9H-carbazol-3-yl)pyridine-2,3-diamine (0.21 g, 0.70 mmol) and nicotinoyl chloride hydrochloride (0.1780 g, 1.0 mmol) dissolved in THF (5 mL). To the mixture sodium bicarbonate (0.13 mL, 1.6 mL) was added. After stirring for 30 minutes, $Et_3N$ (0.1 mL) was added and the reaction mixture refluxed for 24 hr. After the reaction was complete (analyzed by TLC), the mixture was allowed to reach room temperature. The mixture was washed with water (30 mL), and extracted with $CH_2Cl_2$ (3×30 mL). The combined organic phases were washed with brine and dried over anhydrous $Na_2SO_4$, filtered, and concentrated under reduced pressure. The crude oil was purified via column chromatography over silica gel and the product 7b was obtained (0.240 g, 0.44 mmol, 63%) as a yellow solid. TLC analysis in ethyl acetate-hexane (1:3), $R_f$=0.60. $^1$H NMR (400 MHz, DMSO-$d_6$) δ 1.31 (3H, t, J=7.3 Hz) 4.43 (2H, q, J=7.3 Hz), 6.81 (1H, q, J=4.1 Hz), 7.15 (1H, t, J=7.8 Hz), 7.42 (1H, t, J=7.6 Hz), 7.5 (1 h, t, J=7.1 Hz), 7.67 (1H, d, J=8.6 Hz), 8.04 (1H, d, J=7.1 Hz), 8.27 (1H, s), 8.32 (1H, s), 8.41 (1H, d, J=8.6 Hz), 8.78 (1H, d, J=3.3 Hz), 9.23 (1H, s), 10.03 (1H, s); $^{13}$C NMR (100 MHz, DMSO-$d_6$) δ 13.8, 36.7, 108.8, 112.5, 113.2, 119.0, 119.9, 121.7, 123.1, 125.2, 129.9, 132.8, 134.7, 135.5, 139.7, 144.6, 148.9, 151.8, 164.6.

Synthesis of 2-(2-(9-ethyl-9H-carbazol-4-yl)amino-pyridin-3-yl)amino)-1-morpholinoethanone (7c)

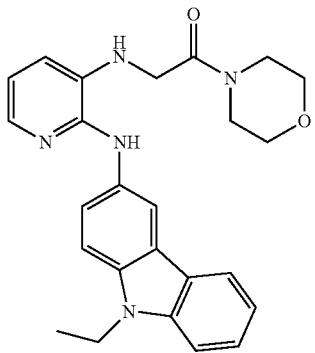 [SMILES: CCn1c2ccccc2c2cc(Nc3ncccc3NCC(=O)N3CCOCC3)ccc21]

The $N^2$-(9-Ethyl-9H-carbazol-3-yl)-pyridine-2,3-diamine was prepared following procedure as in Step (i) 7a. Step (ii) In a 100 mL three neck round bottom flask equipped with a stirring bar and reflux condenser, $N^2$-(9-ethyl-9H-carbazol-3-yl)pyridine-2,3-diamine 6a, 4-(chloroacetyl)morpholine (0.08 mL, 0.6 mmol) and $Et_3N$ (0.07 mL) were dissolved in THF (5 mL). The reaction mixture was refluxed for 24 h until the reaction was complete as indicated by TLC analysis. The mixture was washed with water (30 mL), and extracted with $CH_2Cl_2$ (3×30 mL). The combined organic phases were washed with brine and dried over anhydrous $Na_2SO_4$, filtered, and concentrated under reduced pressure. The crude was purified via column chromatography over silica gel and the product 7c was obtained as a white solid (0.18 g, 0.42 mmol, 70%). TLC analysis in $CH_2Cl_2$-MeOH (9:1), $R_f$=0.34. $^1$H NMR (400 MHz, CDCl$_3$) δ 1.45 (3H, t, J=7.1 Hz), 3.49 (2H, t, J=7.1 Hz) 3.72 (4H, t, J=6.0 Hz), 3.92 (2H, s), 4.38 (2H, q, J=6.8 Hz), 6.77 (1H, t, J=7.3 Hz), 6.90 (1H, d, J=6.3 Hz), 7.22 (1H, t, J=7.21 Hz), 7.29 (1H, s), 7.39 (1H, d, J=4.3 Hz), 7.41 (1H, d, J=4.3 Hz), 7.46 (1H, t, J=6.8 Hz), 7.52 (1H, d, J=8.6 Hz), 8.05 (2H, d, J=8.1 Hz); $^{13}$C NMR (100 MHz, CDCl$_3$) δ 13.9, 14.2, 21.0, 28.4, 29.7, 36.1, 37.6, 52.7, 56.3, 60.4, 108.4. 110.4, 112.0, 113.9, 118.4, 120.6, 121.4, 123.0, 125.4, 131.7, 135.3, 136.8, 140.3, 151.7, 154.7, 156.3, 168.3.

General Method for the Synthesis of 2-amino-3-nitropyridine derivatives (8a-b)

In a 100 mL three neck round bottom flask equipped with a stirring bar and reflux condenser, 2-chloro-3-nitropyridine 5, 1 equiv. of primary or secondary amine, and $Et_3N$ (1 equiv.) were dissolved in THF (3 mL). The reaction mixture is refluxed at 65° C. for 2 h. After the reaction was complete (analyzed by TLC), the mixture was allowed to reach room temperature. The mixture was washed with water (30 mL), and extracted with ethyl acetate (3×30 mL). The combined organic phases were washed with brine and dried over anhydrous $Na_2SO_4$, filtered, and concentrated under reduced pressure. The crude oil was purified via column chromatography with silica gel to obtain the appropriate 2-amino-3-nitropyridine derivative 8a or 8b.

(3-Morpholin-4-yl-propyl)-(3-nitro-pyridin-2-yl)-amine (8a)

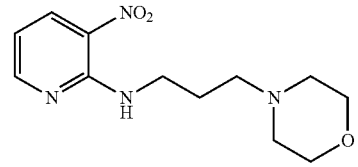 [SMILES: O=[N+]([O-])c1cccnc1NCCCN1CCOCC1]

$^1$H NMR (400 MHz, CDCl$_3$) δ 1.86 (2H, quint, J=6.66 Hz), 2.48 (6H, m), 3.69 (2H, t, J=6.51 Hz), 3.75 (4H, t, J=4.50 Hz), 6.61 (1H, t, J=5.70 Hz), 8.40 (1H, d, J=7.10 Hz), 8.62 (1H, br); $^{13}$C NMR (100 MHz, CDCl$_3$) δ 25.5, 40.3, 53.9, 57.2, 66.7, 111.4, 128.0, 135.2, 152.6, 155.7.

4-(3-Nitro-pyridin-2-yl)-morpholine (8b)

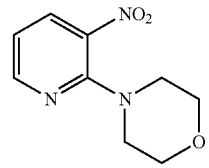 [SMILES: O=[N+]([O-])c1cccnc1N1CCOCC1]

$^1$H NMR (400 MHz, CDCl$_3$) δ 3.45 (4H, t, J=4.48 Hz), 3.79 (4H, t, J=4.33 Hz), 6.78 (1H, dd, J=4.48, 7.86 Hz), 8.12 (1H, d, J=7.98 Hz), 8.33 (1H, d, J=4.38 Hz); $^{13}$C NMR (100 MHz, CDCl$_3$) δ 48.4, 66.6, 113.8, 133.2, 135.6, 151.8, 152.7.

General Method for the Synthesis of 2,3-diaminopyridine Derivatives (9a-b)

In a 100 mL three neck round bottom flask equipped with a stirring bar and reflux condenser, 2-amino-3-nitropyridine derivative 8a or 8b was dissolved in EtOH (25 mL) and water (25 mL). After stirring for 10 min, $SnCl_2.2H_2O$ (1.5 equiv) and HCl were added, and the reaction mixture was refluxed at 80° C. for 5 h. After reaction completion (analysis by TLC), the mixture was allowed to reach room temperature and washed with 1M KOH. The layers were separated and the aqueous layer was further extracted with ethyl acetate (3×30 mL). The combined organic phases were washed with brine and dried over anhydrous Na₂SO₄, filtered and concentrated under reduced pressure. The crude solid was purified via column chromatography with silica gel to obtain the appropriate 2,3-diaminopyridine derivatives 9a or 9b.

N²-(3-Morpholin-4-yl-propyl)-pyridine-2,3-diamine (9a)

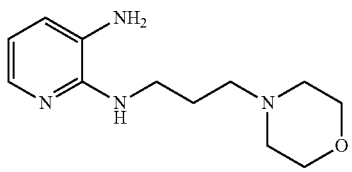

¹H NMR (400 MHz, CDCl₃) δ 1.84 (2H, quint, J=6.37 Hz), 2.48 (6H, q, J=6.48 Hz), 3.50 (2H, t, J=6.35 Hz), 3.73 (4H, t, J=4.64 Hz), 6.48 (1H, dd, J=5.11, 7.37 Hz), 6.81 (1H, dd, J=1.52, 7.37 Hz), 7.71 (1H, dd, J=1.52, 5.12 Hz); ¹³C NMR (100 MHz, CDCl₃) δ 25.3, 41.72, 53.8, 58.2, 67.0, 112.3, 121.2, 128.5, 138.8, 150.4.

2-Morpholin-4-yl-pyridin-3-ylamine (9b)

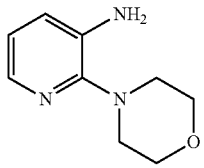 [SMILES: Nc1cccnc1N1CCOCC1]

¹H NMR (400 MHz, CDCl₃) δ3.13 (4H, t, J=4.73 Hz), 3.86 (4H, t, J=4.58 Hz), 6.85 (1H, dd, J=4.80, 7.73 Hz), 6.95 (1H, dd, J=1.65, 7.74 Hz), 7.81 (1H, dd, J=1.64, 4.80 Hz); ¹³C NMR (100 MHz, CDCl₃) δ 49.1, 67.4, 119.7, 121.7, 135.4, 137.8, 150.7.

Synthesis of 9-ethyl-9H-carbazole-3-carboxylic acid (10)

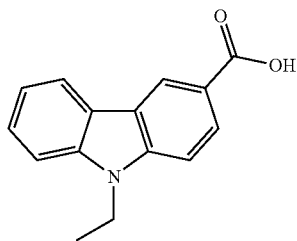 [SMILES: CCn1c2ccccc2c2cc(C(=O)O)ccc21]

In a 100 mL three neck round bottom flask equipped with a stirring bar and reflux condenser, 9-ethyl-3-carbazolecarboxaldehyde (0.66 g, 3.0 mmol), KMnO₄ (0.474 g, 3.0 mmol), and NaOH (0.120 g, 3.0 mmol) were added dissolved in water (10 mL). The reaction mixture was refluxed for 3 h with vigorous magnetic stirring. As the reaction progresses, the intense purple color (manganese VII) will gradually disappear as it is reduced (to manganese IV) which precipitates as brown manganese dioxide. After 3 h, the reaction is allowed to reach room temperature, and the manganese dioxide precipitate was filtered with a Buchner funnel. The filtrate was pour into a separatory funnel and acidified with 1M HCl (until reach pH 6.5-7.5). The carbazole carboxylic acid precipitate 10 was vacuum filtered and washed with water (2×50 mL). The product was purified by recrystallization in CH₂Cl₂-MeOH (9:1). R$_f$=0.64. ¹H NMR (400 MHz, DMSO-d₆) δ 1.33 (3H, t, J=7.0 Hz), 4.48 (2H, q, J=6.74 Hz), 7.26 (1H, t, J=7.35 Hz), 7.51 (1H, t, J=7.54 Hz), 7.65 (1H, d, J=3.74 Hz), 7.68 (1H, d, J=4.26 Hz), 8.06 (1H, d, J=8.66 Hz), 8.27 (1H, d, J=7.94), 8.78 (1H, s), 12.52 (1H, bs); ¹³C NMR (100 MHz, DMSO-d₆) δ 13.7, 37.2, 108.8, 109.5, 119.7, 120.7, 121.1, 121.9, 122.3, 122.5, 140.2, 142.1, 168.0.

Synthesis of 9-Ethyl-9H-carbazole-3-carboxylic Acid [2-(3-morpholin-4-yl-propylamino)-pyridin-3-yl]-amide (11a)

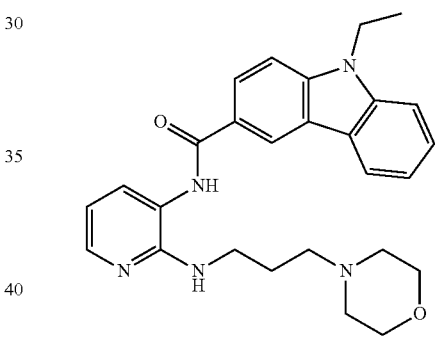

In a 100 mL three-neck round-bottom flask was charged with N²-(3-Morpholin-4-yl-propyl)-pyridine-2,3-diamine derivative 9a (0.210 g, 0.880 mmol), 9-ethyl-9H-carbazole-3-carboxylic acid 10 (0.239 g, 1.0 mmol), HOBt (0.270 g, 2.0 mmol), and EDAC (0.3830 g, 2.0 mmol) dissolved in THF (10 mL). The mixture was stirred for 10 min, then Et₃N (0.3 mL, 2.0 mmol) was added. The mixture was stirred at room temperature for 16 h. After the reaction was complete (analyzed by TLC), the solution was washed with water (30 mL), and the product was extracted with CH₂Cl₂ (3×20 mL). The combined organic phases were washed with brine and dried over anhydrous Na₂SO₄, filtered, and concentrated under reduced pressure. The crude was purified via column chromatography over silica gel and the product 11a was obtained as a white solid (0.180 g, 0.390 mmol, 45%). TLC analysis in CH₂Cl₂-MeOH (9:1), R$_f$=0.52. ¹H NMR (400 MHz, DMSO-d₆) δ 1.34 (3H, t, J=7.8 Hz), 1.72 (2H, t, J=6.8 Hz), 2.34 (5H, s), 3.50 (4H, s), 4.50 (2H, q, J=7.1 Hz), 6.09 (1H, t, J=4.6 Hz), 6.59 (1H, t, J=6.8 Hz), 7.28 (1H, t, J=7.6 Hz), 7.50 (1H, d, J=6.3 Hz), 7.52 (1H, d, J=7.8 Hz), 7.69 (1H, d, J=8.9 Hz), 7.71 (1H, d, J=8.6 Hz), 7.95 (1H, d, J=4.3 Hz), 8.14 (1H, d, J=8.1 Hz), 8.23 (1H, d, J=7.8 Hz) 8.86 (1H, s); ¹³C NMR (100 MHz, DMSO-d6) δ 13.6, 25.8, 30.7, 37.2, 53.4, 56.2, 66.1, 108.5, 109.6, 111.2, 119.3, 119.5, 120.5, 120.8, 121.7, 122.4, 124.9, 125.8, 126.3, 133.6, 140.2, 141.4, 144.7, 154.0, 166.5.

Synthesis of 9-Ethyl-9H-carbazole-3-carboxylic Acid (2-morpholin-4-yl-pyridin-3-yl)-amide (11b)

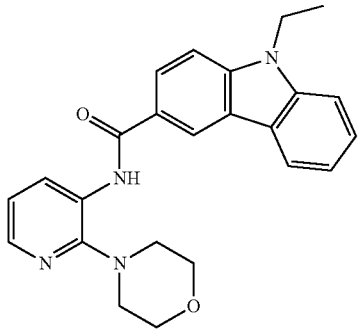 [SMILES: CCn1c2ccccc2c2cc(C(=O)Nc3cccnc3N3CCOCC3)ccc21]

In a 100 mL three-neck round-bottom flask was charged with 2-Morpholin-4-yl-pyridin-3-ylamine derivative 9b (0.180 g, 1.0 mmol), 9-ethyl-9H-carbazole-3-carboxylic acid 10 (0.1196 g, 0.5 mmol), HOBt (0.0675 g, 0.5 mmol), and EDAC (0.0958 g, 0.5 mmol) dissolved in THF (10 mL). The mixture was stirred for 10 min, then $Et_3N$ (0.3 mL, 2.0 mmol) was added. The mixture was stirred at room temperature for 16 h. After the reaction was complete (analyzed by TLC), the solution was washed with water (30 mL), and the product was extracted with $CH_2Cl_2$ (3×20 mL). The combined organic phases were washed with brine and dried over anhydrous $Na_2SO_4$, filtered, and concentrated under reduced pressure. The crude was purified via column chromatography over silica gel and the product 11b was obtained as a white solid (0.1271 g, 0.320 mmol, 32%). TLC analysis in $CH_2Cl_2$-MeOH (9:1), $R_f$=0.93. $^1$H NMR (400 MHz, $CDCl_3$) δ 1.49 (3H, t, J=7.1 Hz), 3.17 (4H, t, J=4.8 Hz), 3.99 (4H, t, J=4.8 Hz), 4.44 (2H, q, J=6.8 Hz), 7.16 (1H, d, J=4.3 Hz), 7.17 (1H, d, J=4.44 Hz), 7.36 (1H, t, J=7.6 Hz) 7.49 (1H, d, J=7.8 Hz), 7.53 (1H, d, J=8.3 Hz), 7.55 (1H, d, J=8.1 Hz), 8.03 (1H, d, J=2.0 Hz), 8.05 (1H, d, J=1.8 Hz) 8.14 (1H, d, J=1.8 Hz), 8.15 (1H, d, J=1.8 Hz), 8.71 (1H, d, J=1.8 Hz), 8.85 (1H, d, J=1.8 Hz) 8.86 (1H, d, J=1.5 Hz), 9.06 (1H, s); $^{13}$C NMR (100 MHz, $CDCl_3$) δ 13.8, 37.9, 50.6, 67.6, 108.6, 109.0, 119.9, 120.6, 120.9, 122.8, 123.1, 124.4, 124.8, 126.7, 127.3, 128.7, 140.7, 142.1, 142.4, 152.7, 165.9.

Synthesis of orhto-diamide Derivatives 14a-h

Synthesis of 3-((9-ethyl-9H-carbazol-3-yl)carbamoyl)pyrazine-2-carboxylic Acid Precursor (13) for Compounds 14a-d

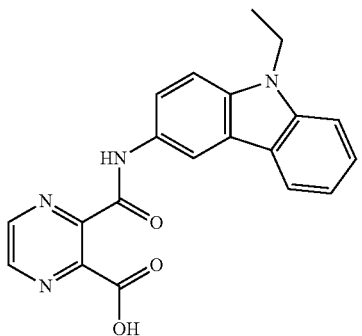 [SMILES: CCn1c2ccccc2c2cc(NC(=O)c3nccnc3C(=O)O)ccc21]

In a 100 mL flask, 2,3-pyrazinedicarboxylic anhydride 12 (0.7505 g, 5 mmol) was reacted with 2 (1.0511 g, 5 mmol) in dry THF (10 mL) stirred overnight at rt. The mixture was transferred to a separatory funnel and extracted with $CH_2Cl_2$ (3×10 mL) and NaOH (1N) (10 mL). The organic phase was separated and HCl (1N) (10 mL) was added to the aqueous phase until a pH=2 was reached and a precipitate formed. The solid was filtered and washed with water (20 mL), and concentrated under reduced pressure to provide 13 (1.73 g, 4.8 mmol, 96%), as a yellow solid.

$^1$H NMR (400 MHz, DMSO-$d_6$) δ 1.33 (3H, t, J=7.02 Hz), 2.51 (4H, d, J=1.59 Hz), 4.46 (2H, q, J=7.01 Hz), 7.21 (1H, t, J=7.52 Hz), 7.47 (1H, t, J=7.66), 7.59 (1H, d, J=4.10 Hz), 7.61 (1H, d, J=3.48 Hz), 7.73 (1H, d, J=7.27 Hz), 8.58 (1H, s), 8.63 (2H, s); $^{13}$C NMR (100 MHz, DMSO-$d_6$) δ 14.2, 37.5, 109.4, 109.7, 110.95, 119.1, 119.7, 120.6, 122.3, 122.6, 126.2, 131.8, 136.8, 140.5, 141.8, 144.8, 145.8, 164.3.

Synthesis of $N^2$-(9-ethyl-9H-carbazol-3-yl)-$N^3$-(2morpholinoethyl)pyrazine-2,3-dicarboxamide (14a)

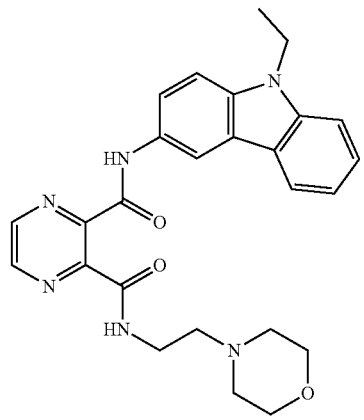 [SMILES: CCn1c2ccccc2c2cc(NC(=O)c3nccnc3C(=O)NCCN3CCOCC3)ccc21]

In an oven dried 25 mL three-neck round bottom flask, 13 (0.0945 g, 0.20 mmol) was dissolved in THF (8 mL). Then, 4-(2-aminoethyl)morpholine (28.9 μL, 0.22 mmol) was added with HOBt (0.02703 g, 0.20 mmol) and EDC (0.0460 g, 0.24 mmol). The mixture was stirred at room temperature for 3 h. The mixture was transferred to a separatory funnel and extracted with $CH_2C_2$ (3×10 mL) and washed with $NaHCO_3$ (1N) (10 mL). The organic phase was separated, dried over anhydrous $Na_2SO_4$, filtered and concentrated under reduced pressure. The crude product was purified by silica gel column chromatography with $CH_2Cl_2$-MeOH (via gradient starting of 99:1) to provide 14a (0.04 g, 0.085 mmol, 42.3%). $R_f$=0.52 $^1$H NMR (400 MHz, $CDCl_3$) δ 1.42 (3H, t, J=7.2 Hz), 2.59 (3H, s), 2.74 (2H, t, J=5.6 Hz), 3.69 (5H, m, J=4.0 Hz), 4.35 (2H, q, J=7.6 Hz), 7.22 (1H, t, J=7.6 Hz), 7.26 (1H, s), 7.35 (1H, d, J=8.8 Hz), 7.38 (1H, d, J=8.0 Hz), 7.47 (1H, t, J=7.2 Hz), 7.68 (1H, d, J=8.4 Hz), 8.10 (1H, d, J=8.0 Hz), 8.56 (1H, s), 8.66 (1H, d, J=12.0 Hz), 9.52 (1H, s); $^{13}$C NMR (100 MHz, $CDCl_3$) δ 36.0, 37.6, 53.2, 56.7, 66.5, 108.5, 108.5, 112.7, 118.8, 119.2, 120.7, 122.8, 123.0, 125.9, 129.2, 137.4, 140.4, 143.4, 144.8, 145.1, 148.6, 160.9, 165.7.

Synthesis of N²-(9-ethyl-9H-carbazol-3-yl)-N³-(3-morpholinopropyl)pyrazine-2,3-dicarboxamide (14b)

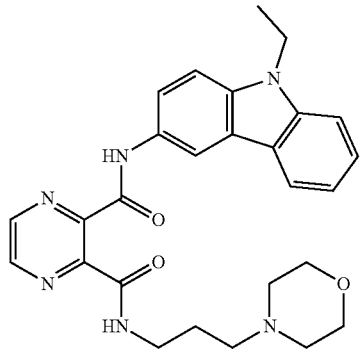 [SMILES: CCn1c2ccccc2c2cc(NC(=O)c3nccnc3C(=O)NCCCN3CCOCC3)ccc21]

In an oven dried 25 mL three-neck round bottom flask, 13 (0.0945 g, 0.20 mmol) was dissolved in dried distilled THF (10 mL). Then, 3-morpholinopropan-1-amine (43.80 µL, 0.30 mmol) was added with HOBt (0.02703 g, 0.20 mmol) and EDC (0.0460 g, 0.24 mmol). The mixture was stirred at room temperature overnight. The reaction mixture was concentrated and no extraction to the crude was performed. The crude product was purified by silica gel column chromatography with CH₂Cl₂-MeOH (via gradient starting of 9:1) to provide 14b (0.030 g, 0.062 mmol, 31%). $R_f$=0.50. ¹H NMR (400 MHz)(CDCl₃) δ 1.40 (3H, t, J=7.19 Hz), 1.84 (2H, m), 2.47 (4H, s), 2.58 (2H, t, J=6.03 Hz), 3.59 (4H, t, J=4.37 Hz), 3.69 (2H, q, J=5.67 Hz), 4.31 (2H, q, J=7.19 Hz), 7.21, (1H, t, J=7.47 Hz), 7.26 (1H, s), 7.32 (1H, d, J=8.70 Hz), 7.37 (1H, d, J=8.15 Hz), 7.47 (1H, t, J=7.31 Hz), 7.68 (1H, d, J=8.69 Hz), 8.09 (1H, d, J=7.27 Hz), 8.44 (1H, d, J=4.78 Hz), 8.58 (1H, d, J=1.92 Hz), 8.63 (1H, s), 9.45 (1H, s); ¹³CNMR (100 MHz, CDCl₃) δ 13.8, 24.4, 37.5, 40.2, 53.6, 58.2, 66.9, 108.4, 108.5, 112.6, 118.8, 119.2, 120.8, 122.8, 123.0, 125.8, 129.3, 137.3, 140.4, 143.5, 144.3, 145.7, 148.4, 161.2, 165.1.

Synthesis of Pyrazine-2,3-dicarboxylic acid 2-[(9-ethyl-9H-carbazol-3-yl)-amide]-3-[(3-imidazol-1-yl-propyl)-amide] (14c)

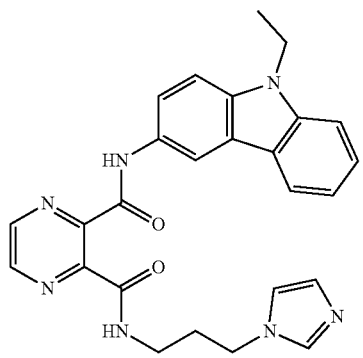 [SMILES: CCn1c2ccccc2c2cc(NC(=O)c3nccnc3C(=O)NCCCn3ccnc3)ccc21]

In an oven dried 25 mL three-neck flask, 13 (0.0945 g, 0.20 mmol) was dissolved in dried distilled THF (10 mL). Then, 3-(1H-imidazol-1-yl)propan-1-amine (35.8 µL, 0.30 mmol) was added with HOBt (0.02703 g, 0.20 mmol) and EDC (0.0460 g, 0.24 mmol). The mixture was stirred at room temperature overnight. No extraction was done. The crude product was purified by silica gel column chromatography with CH₂Cl₂/Methanol (via gradient starting of 9:1) to provide 14c (0.050 g, 0.106 mmol, 53%). $R_f$=1.3. ¹H NMR (400 MHz, CDCl₃) δ 1.38 (3H, t, J=7.20 Hz), 2.06 (2H, m), 3.44 (2H, t, J=6.0 Hz), 4.08 (2H, t, J=7.20 Hz), 4.27 (2H, q, J=7.2 Hz), 6.92 (2H, d, J=22.0 Hz), 7.19 (1H, t, J=7.6 Hz), 7.30 (1H, d, J=8.0 Hz), 7.35 (1H, d, J=15.2 Hz), 7.46 (1H, t, J=7.20 Hz), 7.52, 7.99 (1H, d, J=11.2 Hz), 8.45 (2H, s), 8.50 (1H, s); 9.72 (1H, s); ¹³C NMR (100 MHz, CDCl₃) δ 13.7, 31.0, 36.8, 37.5, 44.4, 108.5, 108.5, 112.3, 118.8, 118.9, 120.6, 122.6, 122.9, 125.9, 128.9, 129.3, 137.3, 140.3, 143.3, 144.6, 144.7, 148.3, 160.8, 165.9.

Synthesis of N²-(9-ethyl-9H-carbazol-3-yl)-N³-(2-methoxyethyl)pyrazine-2,3-dicarboxamide (14d)

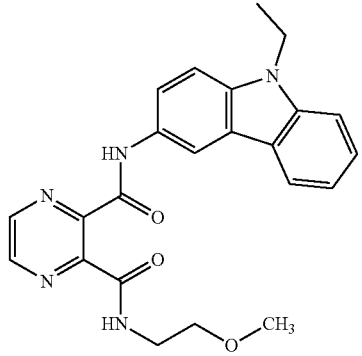 [SMILES: CCn1c2ccccc2c2cc(NC(=O)c3nccnc3C(=O)NCCOC)ccc21]

In an oven dried 25 mL three-neck round bottom flask, 13 (0.0945 g, 0.20 mmol) was dissolved in dried distilled THF (10 mL). Then, 3-(1H-imidazol-1-yl)propan-1-amine (19.13, 0.22 mmol) was added with Et₃N (69.74 µL, 0.50 mmol), HOBt (0.02703 g, 0.20 mmol) and EDC (0.0460 g, 0.24 mmol). The mixture was stirred at room temperature overnight. No extraction was performed. The crude product was concentrated and purified by silica gel column chromatography with CH₂Cl₂-MeOH (via gradient starting of 9:1) to provide 14d (0.010 g, 0.024 mmol, 12.0%). $R_f$=0.54. ¹H NMR (400 MHz, CDCl₃) δ 1.44 (3H, t, J=7.2 Hz), 3.41 (3H, s), 3.67 (2H, t, J=5.60 Hz), 3.79 (2H, q, J=5.20 Hz), 4.38 (2H, q, J=7.20 Hz), 7.09 (11H, s), 7.22 (11H, t, J=12.8 Hz), 7.40 (2H, t, J=8.0 Hz), 7.51J (1H, t, J=10.4 Hz), 8.11 (1H, d, J=7.6 Hz), 8.58 (1H, d, J=2.0 Hz), 8.70 (2H, q, J=2.4 Hz), 9.36J (1H, s); ¹³C NMR (100 MHz, CDCl₃) δ 13.0, 37.6, 39.7, 58.8, 70.9, 108.5, 112.8, 118.8, 119.2, 120.82, 122.8, 123.1, 125.9, 129.3, 137.5, 140.5, 143.6, 144.6, 145.6, 148.1, 161.0, 165.3.

Synthesis of 2-((9-ethyl-9H-carbazol-3-yl)carbamoyl)benzoic Acid Precursor (13) for Compounds 14e-f

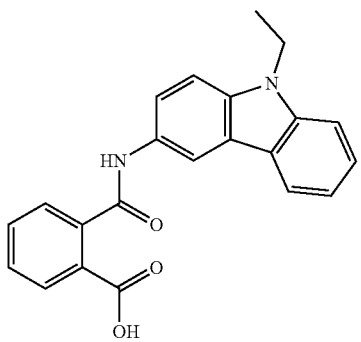 [SMILES: CCn1c2ccccc2c2cc(NC(=O)c3ccccc3C(=O)O)ccc21]

In a 100 mL one-neck flask, carbazole 2 (1.4812 g, 10 mmol), was reacted with phthalic anhydride 12 (2.1021 g, 10 mmol) in dry THF stirred for 3 h at room temperature. The reaction mixture was transferred to a separatory funnel and extracted with $CH_2Cl_2$ (3×10 mL) and NaOH (1N) (10 mL). The organic phase was separated, and HCl (1N) (10 mL) was added to the aqueous phase until a pH=2 was reached and a precipitate formed. The solid was filtered and washed with water (30 mL), and concentrated under reduced pressure to provide 13 (2.78 g, 7.76 mmol, 77.6%), as a white solid. TLC showed the product to be pure: $CH_2Cl_2$-MeOH (9:1). $R_f$=0.45. $^1$H NMR (400 MHz, DMSO-$d_6$) δ 1.31 (3H, t, J=6.8 Hz), 4.51 (2H, q, J=8.4 Hz), 7.19 (1H, t, J=8.0 Hz), 7.45 (3H, m), 7.56 (2H, t, J=4.0 Hz), 7.69 (2H, d, J=8.4 Hz), 7.84 (1H, t, J=7.6 Hz), 8.10 (1H, d, J=3.2 Hz), 8.53 (1H, s), 12.43 (1H, s); $^{13}$C NMR (400 MHz, DMSO-$d_6$) δ 13.7, 37.0, 109.0, 109.2, 111.4, 118.6, 119.4, 120.2, 121.9, 122.2, 125.7, 128.7, 128.9, 129.5, 129.6, 132.0, 134.9, 136.2, 138.1, 140.0, 166.3, 172.3.

Synthesis of $N^1$-(9-ethyl-9H-carbazol-3-yl)-$N^2$-(2-methoxyethyl)phthalamide (14e)

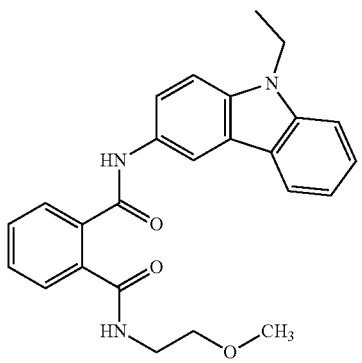 [SMILES: CCn1c2ccccc2c2cc(NC(=O)c3ccccc3C(=O)NCCOC)ccc21]

In a three-neck round bottom flask, 13 (0.0941 g, 0.20 mmol) was dissolved in dry THF (6 mL). Then, 2-methoxyethanamine (18.11 μL, 0.30 mmol) was added with HOBt (0.02703 g, 0.20 mmol) and EDC (0.0460 g, 0.24 mmol). The mixture was stirred at room temperature overnight. The reaction mixture was transferred to a separatory funnel and extracted with $CH_2Cl_2$ (3×10 mL) and NaHCO$_3$ (1N) (10 mL). The organic phase was dried over anhydrous Na$_2$SO$_4$, filtered and concentrated under reduced pressure. The crude product was purified by silica gel column chromatography with $CH_2Cl_2$-Methanol (via gradient starting of 99:1) to provide 14e (0.0349 g, 0.084 mmol, 42%). TLC showed the product to be pure: $CH_2Cl_2$-MeOH (9:1). $R_f$=0.61. $^1$H NMR (400 MHz, CDCl$_3$) δ 1.40 (3H, t, J=7.2 Hz), 3.24 (3H, s), 3.46 (2H, t, J=5.2 Hz), 3.61 (2H, q, J=5.2 Hz), 4.33 (2H, q, J=7.2 Hz), 6.82 (1H, t, J=5.2 Hz), 7.21 (1H, t, J=7.6 Hz), 7.32 (1H, d, J=8.4 Hz), 7.38 (1H, d, J=8.0 Hz), 7.45 (1H, d, J=7.2 Hz), 7.50 (1H, t, J=3.6 Hz), 7.52 (1H, d, J=9.6 Hz) 7.65 (1H, d, J=8.8 Hz), 7.85 (1H, d, J=9.2 Hz), 8.51 (1H, s), 9.30 (1H, s); $^{13}$C NMR (400 MHz, CDCl$_3$) δ 13.8, 37.5, 40.0, 58.7, 60.4, 70.7, 108.4, 108.5, 112.7, 118.69, 119.4, 120.7, 122.9, 123.0, 125.8, 127.8, 129.4, 130.2, 130.3, 132.0, 134.6, 135.1, 137.2, 140.4, 166.3, 170.2.

Synthesis of $N^1$-(9-ethyl-9H-carbazol-3-yl)-$N^2$-(2-hydroxyethyl)phthalamide (14f)

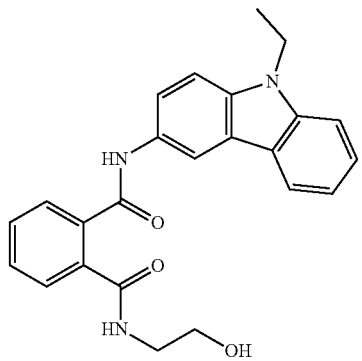 [SMILES: CCn1c2ccccc2c2cc(NC(=O)c3ccccc3C(=O)NCCO)ccc21]

In a three-neck round flask, 13 (0.0941 g, 0.20 mmol) was dissolved in dry THF (5 mL). Then, 2-aminoethanol (19.13 μL, 0.22 mmol) was added with Et$_3$N (69.74 μL, 0.50 mL) followed by HOBt (0.0270 g, 0.20 mmol) and EDC (0.0460 g, 0.24 mmol). The mixture was stirred at room temperature for 2 hr. Then, DMF (23.1 μL, 0.30 mmol) was added and the reaction was left stirring for 1 hr. The reaction mixture was transferred to a separatory funnel and extracted with EtOAc (3×10 mL) and NaHCO$_3$ (1N) (10 mL). The organic phase was dried over anhydrous Na$_2$SO$_4$, filtered and concentrated under reduced pressure. The crude product was purified by silica gel column chromatography with $CH_2Cl_2$-MeOH (via gradient starting of 99:1) to provide product 14f (50.0 mg, 0.125 mmol, 62.3%). TLC showed the product to be pure: $CH_2Cl_2$-MeOH (9:1). $R_f$=0.50. $^1$H NMR (400 MHz, CDCl$_3$) δ 1.38 (3H, t, J=7.2 Hz), 3.53 (2H, q, J=5.2 Hz), 3.73 (2H, t, J=4.8 Hz), 4.25 (2H, q, J=7.2 Hz), 7.11 (1H, t, J=5.2 Hz), 7.19 (1H, t, J=7.2 Hz), 7.26 (1H, d, J=8.8 Hz), 7.36 (1H, d, J=8.0 Hz), 7.40 (1H, d, J=6.8 Hz), 7.42 (1H, t, J=4.8 Hz), 7.47 (1H, t, J=7.2 Hz), 7.63 (1H, d, J=8.4 Hz), 7.68 (1H, d, J=8.0 Hz), 8.03 (1H, d, J=8.0 Hz), 8.43 (1H, s), 9.27 (1H, s); $^{13}$C NMR (400 MHz, CDCl$_3$) δ 13.6, 37.1, 43.1, 60.7, 108.1, 108.2, 112.6, 118.4, 119.5, 120.5, 122.5, 125.4, 127.3, 127.8, 129.4, 129.7, 130.2, 134.9, 135.0, 136.9, 140.1, 167.4, 170.5.

Synthesis of 2-((9-ethyl-9H-carbazol-3-yl)carbamoyl)cyclohexanecarboxylic Acid Precursor (13) for Compounds 14g-h. F

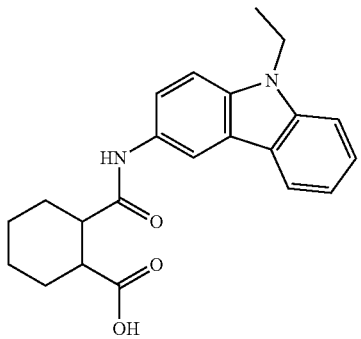 [SMILES: CCn1c2ccccc2c2cc(NC(=O)C3CCCCC3C(=O)O)ccc21]

In a 100 mL flask, carbazole 2 (1.2334 g, 8 mmol) was reacted with 1,2-cyclohexanedicarboxylic anhydride (predominantly cis) 12 (1.2612 g, 6 mmol) in dry THF stirred for 8 h at 70° C. The reaction mixture was extracted with ethyl acetate (3×10 mL) and NaOH (1N). The organic phase was separated and HCl (1N) (10 mL) was added to the aqueous phase until a pH=2 was reached and a precipitate formed. The solid was filtered and washed with water (30 mL), and concentrated under reduced pressure to provide 13 (1.06 g, 2.91 mmol, 48.5%), as a white solid. TLC showed the product to be pure: $CH_2Cl_2$-MeOH (9:1) $R_f$=0.45. $^1$H NMR (400 MHz, $CDCl_3$) δ 1.29 (3H, t, J=7.2 Hz), 1.69 (2H, m), 2.12 (2H, m, J=8.8 Hz), 2.50 (1H, s), 2.61 (1H, t, J=4.0 Hz), 2.95 (1H, q, J=4.4 Hz), 4.43 (2H, q, J=13.6 Hz), 7.16 (1H, t, J=7.6 Hz), 7.43 (1H, t, J=7.6 Hz), 7.52 (1H, t, J=9.2 Hz), 7.54 (1H, d, J=4.0 Hz), 7.56 (1H, d, J=3.6 Hz), 8.04 (1H, d, J=8.0 Hz), 8.43 (1H, s), 10.22 (1H, s); $^{13}$C NMR (400 MHz, $CDCl_3$) δ 13.6, 21.5, 22.8, 24.1, 25.9, 27.87, 28.4, 38.9, 108.7, 109.0, 111.0, 118.4, 119.0, 120.1, 121.8, 122.1, 125.6, 131.7, 135.9, 139.9, 172.4, 175.7.

Synthesis of cyclohexane-1,2-dicarboxylic acid 1-[(9-ethyl-9H-carbazol-3-yl)-amide]-2-[(2-morpholin-4-yl-ethyl)-amide (14g)

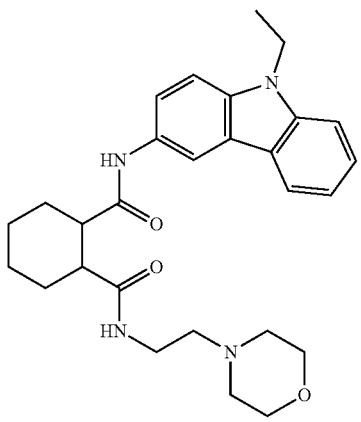 [SMILES: CCn1c2ccccc2c2cc(NC(=O)C3CCCCC3C(=O)NCCN3CCOCC3)ccc21]

In a three-neck round bottom flask, 13 (0.0728 g, 0.20 mmol) was dissolved in dried distilled THF (10 mL). Then, 2-morpholinoethanamine (44.6 µL, 0.34 mmol) was added with HOBt (0.02703 g, 0.20 mmol) and EDC (0.0460 g, 0.24 mmol). The mixture was stirred at room temperature overnight. The reaction mixture was concentrated and no extraction was done. The crude product was purified by silica gel column chromatography with $CH_2Cl_2$/Methanol (via gradient starting of 99:1) to provide 14g (60 mg, 82.38%). TLC showed the product to be pure: $CH_2Cl_2$-MeOH (9:1). $R_f$=0.50. $^1$H NMR (400 MHz, $CDCl_3$) δ 1.38 (3H, t, J=7.2 Hz), 1.50 (2H, m), 1.77 (2H, m), 1.96 (2H, q, J=3.6 Hz), 2.14 (1H, q, J=3.2 Hz), 2.28 (4H, t, J=4.0 Hz), 2.37 (2H, t, J=2.8 Hz), 2.75 (1H, m), 3.02 (1H, q, J=4.4 Hz), 3.33 (2H, q, J=5.6 Hz), 3.59 (4H, t, J=1.6 Hz), 4.31 (2H, q, J=7.2 Hz), 7.20 (1H, t, J=7.6 Hz), 7.26 (1H, d, J=8.8 Hz), 7.37 (1H, d, J=8.0 Hz), 7.47 (1H, t, J=9.6 Hz), 7.49 (1H, d, J=8.8 Hz), 8.04 (1H, d, J=8.0 Hz), 8.36 (1H, s), 8.45 (1H, s); $^{13}$C NMR (100 MHz, $CDCl_3$) δ 13.8, 23.0, 24.0, 24.5, 26.9, 27.8, 37.5, 39.4, 45.1, 45.5, 53.6, 57.7, 66.8, 108.3, 108.45, 112.3, 118.6, 119.1, 120.6, 122.8, 122.9, 125.7, 130.2 136.9, 140.3, 172.5, 174.8.

Synthesis of cyclohexane-1,2-dicarboxylic acid 1-[(9-ethyl-9H-carbazol-3-yl)-amide]-2-[(3-morpholin-4-yl-propyl)-amide] (14h)

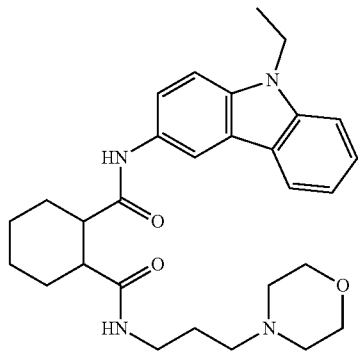 [SMILES: CCn1c2ccccc2c2cc(NC(=O)C3CCCCC3C(=O)NCCCN3CCOCC3)ccc21]

In a three-neck round bottom flask, 13 (0.0728 g, 0.20 mmol) was dissolved in dried distilled THF (10 mL). Then, 3-morpholinopropan-1-amine (49.7 µL, 0.34 mmol) was added with HOBt (0.02703 g, 0.20 mmol) and EDC (0.0460 g, 0.24 mmol). The mixture was stirred at room temperature overnight. The reaction mixture was concentrated and no extraction was performed. The crude product was purified by silica gel column chromatography with $CH_2Cl_2$-MeOH (via gradient starting of 99:1) to provide 14h (0.06 g, 0.12 mmol, 61.1%). $R_f$=0.61. $^1$H NMR (400 MHz, $CDCl_3$) δ 1.40 (3H, t, J=7.2 Hz), 1.56 (3H, m), 1.76 (1H, m), 1.89 (2H, m), 2.00 (2H, q, J=4.0 Hz), 2.09 (2H, q, J=3.2 Hz), 2.31 (6H, t, J=6.0 Hz), 2.71 (1H, m), 3.01 (1H, q, J=4.8 Hz), 3.32 (2H, q, J=6.4 Hz), 3.62 (4H, t, J=4.8 Hz), 4.34 (2H, q, J=7.2 Hz), 7.20 (1H, t, J=7.2 Hz), 7.30 (1H, d, J=4.4 Hz), 7.40 (1H, d, J=8.0 Hz), 7.46 (1H, t, J=6.8 Hz), 7.52 (1H, d, J=8.8 Hz), 8.04 (1H, d, J=10.4 Hz), 8.38 (1H, s), 8.43 (1H, s); $^{13}$C NMR (400 MHz, $CDCl_3$) δ 13.8, 23.0, 24.5, 26.9, 27.8, 37.5, 39.4, 45.1, 45.5, 53.6, 57.7, 66.8, 108.3, 108.5, 112.3, 118.6, 119.1, 120.6, 122.8, 122.9, 125.7, 130.2, 136.9, 140.3, 172.5, 174.8.

General Remarks

All experiments were carried out in pre-dried glassware (≥1 h, 80-90° C.) under a nitrogen atmosphere. Nuclear magnetic resonance (NMR) spectra were obtained using a 400 MHz Bruker Avance UltraShield™ spectrometer. $^1$H (400 MHz) and $^{13}$C (100 MHz) NMR were recorded in CDCl$_3$ or DMSO-d$_6$, unless otherwise used, and the chemical shift were expressed in ppm relative to CDCl$_3$ (7.26 for $^1$H and δ 77.0 for $^{13}$C) or DMSO-d$_6$ (δ 2.50 for $^1$H and δ 39.5 for $^{13}$C) as the internal standard. $^1$H NMR data is reported as position (δ), relative integral, multiplicity (s, singlet; d, doublet; t, triplet; q, quartet; dt, doublet of triplets; dd, doublet of doublets; dq, doublet of quartets; m, multiplet; br, broad peak), coupling constant (J, Hz), and the assignment of the atom. $^{13}$C NMR data are reported as position (δ) and assignment of the atom. Microwave reactions were conducted in a CEM Discovery Microwave for Drug Discovery, SP-1445.

Chemistry

Progress of the reaction was monitored via TLC analysis (General purpose silica gel on glass 5×20 cm with UV indicator, and visualized by UV fluorescent Spectroline E Series Ultraviolet lamps, in most cases followed by staining with I$_2$. The compounds were purified via column chromatography over silica gel (70-230 mesh, 60 Å) with the appropriate size column (24/40, 12 in.×0.5 in.) or (24/40, 12 in.×0.72 in.).

Synthesis of N$^2$-(5-(diethylamino)pentan-2-yl)-N$^4$-(9-ethyl-9H-carbazol-3-yl)pyrimidine-2,4-diamine (32) via N-(2-chloropyrimidin-4-yl)-9-ethyl-9H-carbazol-3-amine (30) with 2-Amino-5-diethylaminopentane In a test tube, 30 (100 mg, 0.31 mmol) was dissolved in DMSO (1 mL). Cesium Carbonate (202 mg, 0.62 mol) and 2-Amino-5-diethylaminopentane (180.2 μL, 0.93 mol) were added. The mixture was stirred in a CEM Discover Model Discover/Electromagnetic stir no. SP-1445 microwave at 120° C. for 6 h. The reaction was transferred to a separatory funnel, and an extraction was done using CH$_2$C$_{12}$ (10 mL) and distilled H$_2$O (5 mL). The aqueous phase and the organic phase were separated, and the aqueous phase was extracted with CH$_2$C$_{12}$ (5 mL). Afterwards, then the organic phase was extracted with brine, dried over Na$_2$SO$_4$, filtered and concentrated under vacuum on rotavap. The crude product was purified by silica gel column chromatography (CH$_2$Cl$_2$/methanol 9:1 as eluent and 100RL Et$_3$N) to obtain 32 in a yield of 0.03 g (0.08 mol, 21.8%). TLC analysis showed the product to be pure: (CH$_2$Cl$_2$/methanol 3:1) Rf=0.5.

Synthesis of N$^2$-(3-(1H-imidazol-1-yl)propyl)-N$^4$-(9-ethyl-9H-carbazol-3-yl)pyrimidine-2,4-diamine (33) with N-(2-chloropyrimidin-4-yl)-9-ethyl-9H-carbazol-3-amine (30) and 1-(3-Aminopropyl)imidazole In a test tube, 30 (100 mg, 0.31 mmol) was dissolved in DMSO (1 mL). 1-(3-Aminopropyl)imidazole (37.0 μL, 0.31 mol) were added. The mixture was stirred in the microwave at 160° C. for 3 h. The reaction was transferred to a separatory funnel, and an extraction was done using CH$_2$Cl$_2$ (10 mL) and distilled H$_2$O (5 mL). The aqueous phase and the organic phase were separated, and the aqueous phase was extracted with CH$_2$Cl$_2$ (5 mL). Afterwards, the organic phase was extracted with brine, dried over Na$_2$SO$_4$, filtered and concentrated under vacuum on rotavap. The crude product was purified by silica gel column chromatography (CH$_2$Cl$_2$/methanol 9:1 as eluent and 100 μL Et$_3$N) to obtain 33 in a yield of 41.7% (0.053 g, 0.13 mmol). TLC analysis showed the product to be pure: (CH$_2$Cl$_2$/methanol 3:1) Rf=0.53.

Synthesis of N$^4$-(9-ethyl-9H-carbazol-3-yl)-N$^2$-(piperidin-2-ylmethyl)pyrimidine-2,4-diamine (34) with N-(2-chloropyrimidin-4-yl)-9-ethyl-9H-carbazol-3-amine (30) and 2-(Aminomethyl)piperidine In a test tube, 30 (100 mg, 0.31 mmol) was dissolved in 1,4-Dioxane (1 mL). Cesium Carbonate (101 mg, 0.31 mol) and 2-(Aminomethyl)piperidine (37.6 μL, 0.31 mol) were added. The mixture was stirred in the microwave at 160° C. for 3 h. The reaction was transferred to a separatory funnel, and an extraction was done using CH$_2$Cl$_2$ (10 mL) and distilled H$_2$O (5 mL). The aqueous phase and the organic phase were separated, and the aqueous phase was extracted with CH$_2$Cl$_2$ (5 mL). Afterwards, the organic phase was extracted with brine, dried over Na$_2$SO$_4$, filtered and concentrated under vacuum on rotavap. The crude product was purified by silica gel column chromatography (CH$_2$Cl$_2$/methanol 9:1 as eluent and 100 μL Et$_3$N) to obtain 34 in a yield of 16.1% (0.02 g, 0.05 mmol). TLC analysis showed the product to be pure: (CH$_2$Cl$_2$/methanol 3:1) Rf=0.36.

Synthesis of N$^4$-(9-ethyl-9H-carbazol-3-yl)-N$^2$-(2-(1-methylpyrrolidin-2-yl)ethyl)pyrimidine-2,4-diamine (35) with N-(2-chloropyrimidin-4-yl)-9-ethyl-9H-carbazol-3-amine (30) and 2-(2-Aminoethyl)-1-methylpyrrolidine In a test tube, 30 (100 mg, 0.31 mmol) was dissolved in DMSO (1 mL). Cesium Carbonate (202 mg, 0.62 mol) and 2-(2-Aminoethyl)-1-methylpyrrolidine (74.0 L, 0.62 mol) were added. The mixture was stirred in the microwave at 120° C. for 6 h. The mixture was stirred in the microwave at 120° C. for 6 h. The reaction was transferred to a separatory funnel, and an extraction was done using CH$_2$Cl$_2$ (10 mL) and distilled H$_2$O (5 mL). The aqueous phase and the organic phase were separated, and the aqueous phase was extracted with CH$_2$Cl$_2$ (5 mL). Afterwards, the organic phase was extracted with brine, dried over Na$_2$SO$_4$, filtered and concentrated under vacuum on rotavap. The crude product was purified by silica gel column chromatography (CH$_2$Cl$_2$/methanol 9:1 as eluent and 100 μL Et$_3$N) to obtain 35 in a yield of 0.04 g (0.10 mol, 31.1%). TLC analysis showed the product to be pure: (CH$_2$Cl$_2$//methanol 3:1) Rf=0.5

Synthesis of 2-((4-((9-ethyl-9H-carbazol-3-yl)amino)pyrimidin-2-yl)amino) ethanol (36) with N-(2-chloropyrimidin-4-yl)-9-ethyl-9H-carbazol-3-amine (30) and 2-aminoethanol In a test tube, 30 (80 mg, 0.25 mmol) was dissolved in 1,4-Dioxane (3 mL). DIPEA (87 μL, 0.5 mmol) and 2-aminoethanol (23 μL, 0.375 mmol) were added. The mixture was stirred in the microwave at 160° C. for 4-6 h. The reaction was transferred to a separatory funnel, and an extraction was done using EtOAc (50 mL) and distilled H$_2$O (50 mL). The aqueous phase and the organic phase were separated, and the aqueous phase was extracted with EtOAc (50 mL). Afterwards, the combined organic phase was extracted with brine, dried over Na$_2$SO$_4$, and filtered. The flask was put in the rotovap to eliminate the dissolvent and concentrated under vacuum. The crude product was purified by silica gel column chromatography (gradient 1%-10% methanol in dichloromethane) to obtain 36 in a yield of 20.1 mg (0.056 mmol, 23.1%). TLC analysis showed the product to be pure: (CH$_2$Cl$_2$/MeOH 3:1).

Synthesis of 2-(2-((4-((9-ethyl-9H-carbazol-3-yl)amino)pyrimidin-2-yl)amino) ethoxy)ethanol (37) with N-(2-chloropyrimidin-4-yl)-9-ethyl-9H-carbazol-3-amine (30) and 2-(2-aminoethoxy)ethanol In a test tube, 30 (80 mg, 0.25 mmol) was dissolved in 1,4-Dioxane (3 mL). DIPEA (87 µL, 0.5 mmol) and 2-(2-aminoethoxy)ethanol (38 µL, 0.375 mmol) were added. The mixture was stirred in the microwave at 160° C. for 4-6 h. The reaction was transferred to a separatory funnel, and an extraction was done using EtOAc (50 mL) and distilled H$_2$O (50 mL). The aqueous phase and the organic phase were separated, and the aqueous phase was extracted with EtOAc (50 mL). Afterwards, the organic phase was extracted with brine, dried over Na$_2$SO$_4$, and filtered. The flask was rotovap to eliminate the disolvent and concentrated under vacuum. The crude product was purified by silica gel column chromatography (gradient 1%-10% methanol in dichloromethane) to obtain 38 in a yield of 49.9 mg (0.128 mmol, 50.1%). TLC analysis showed the product to be pure: (CH$_2$Cl$_2$/MeOH 3:1).

Synthesis of N$^4$-(9-ethyl-9H-carbazol-3-yl)-N$^2$-(2-methoxyethyl)pyrimidine-2,4-diamine (38) with N-(2-chloropyrimidin-4-yl)-9-ethyl-9H-carbazol-3-amine (30) and 1-methoxypropane In a test tube, 30 (80 mg, 0.25 mmol) was dissolved in 1,4-Dioxane (3 mL). DIPEA (87 µL, 0.5 mmol) and 2-methoxyethylamine (33 µL, 0.375 mmol) were added. The mixture was stirred in the microwave at 160° C. for 4-6 h. The reaction was transferred to a separatory funnel, and an extraction was done using EtOAc (50 mL) and distilled H$_2$O (50 mL). The aqueous phase and the organic phase were separated, and the aqueous phase was extracted with EtOAc (50 mL). Afterwards, the organic phase was extracted with brine, dried over Na$_2$SO$_4$, and air filtered to then rotovap and concentrated under vacuum. The crude product was purified by silica gel column chromatography (gradient 1%-10% methanol in dichloromethane) to obtain 38 in a yield of 53 mg (0.147 mmol, 58.9%). TLC analysis showed the product to be pure: (CH$_2$Cl$_2$/MeOH 3:1).

Synthesis of N$^2$-(2,4-dimethoxybenzyl)-N$^4$-(9-ethyl-9H-carbazol-3-yl) pyrimidine-2,4-diamine (39) with N-(2-chloropyrimidin-4-yl)-9-ethyl-9H-carbazol-3-amine (30) and (2,4-dimethoxyphenyl)methanamine In a test tube, 30 (80 mg, 0.25 mmol) was dissolved in 1,4-Dioxane (XmL). DIPEA (87 µL, 0.5 mmol) and 2,4-dimethoxybenzylamine (56 µL, 0.375 mol) were added. The mixture was stirred in the microwave at 160° C. for 4-6 h. The reaction was transferred to a separatory funnel, and an extraction was done using EtOAc (50 mL) and distilled H$_2$O (50 mL). The aqueous phase and the organic phase were separated, and the aqueous phase was extracted with EtOAc (50 mL). Afterwards, the organic phase was extracted with brine, dried over Na$_2$SO$_4$, and filtered. The flask was rotovap to eliminate the dissolvent and concentrated under vacuum. The crude product was purified by silica gel column chromatography (gradient 1%-10% methanol in dichloromethane) to obtain 39 in a yield of 28.5 mg (0.063 mmol, 25.2%). TLC analysis showed the product to be pure: (CH$_2$Cl$_2$/MeOH 3:1).

Synthesis of N$^4$-(9-ethyl-9H-carbazol-3-yl)-N$^2$-(2,4,6-trimethoxyphenyl) pyrimidine-2,4-diamine (40) with N-(2-chloropyrimidin-4-yl)-9-ethyl-9H-carbazol-3-amine (30) and 2,4,6-trimethoxyaniline In a test tube, 30 (80 mg, 0.25 mmol) was dissolved in 1,4-Dioxane (3 mL). DIPEA (87 µL, 0.5 mmol) and 2,4,6-trimethoxyaniline (68 mg, 0.375 mmol) were added. The mixture was stirred in the microwave at 160° C. for 4-6 h. The reaction was transferred to a separatory funnel, and an extraction was done using EtOAc (50 mL) and distilled H$_2$O (50 mL). The aqueous phase and the organic phase were separated, and the aqueous phase was extracted with EtOAc (50 mL). Afterwards, the organic phase was extracted with brine, dried over Na$_2$SO$_4$, and filtered. The flask was rotovap to eliminate the dissolvent and concentrated under vacuum. The crude product was purified by silica gel column chromatography (gradient 1%-10% methanol in dichloromethane) to obtain 40 in a yield of 71.4 mg (0.152 mmol, 60.9%). TLC analysis showed the product to be pure: (CH$_2$Cl$_2$/MeOH 3:1).

Synthesis of 1-(5-chloro-2,4-dimethoxyphenyl)-3-(4-((9-ethyl-9H-carbazol-3-yl)amino)pyrimidin-2-yl) urea (41) with N$^4$-(9-ethyl-9H-carbazol-3-yl)-6-methylpyrimidine-2,4-diamine (30a) and 1-chloro-5-cyanato-2,4-dimethoxybenzene A 100 mL round flask was charged with 30a (96.22 mg) was dissolved in THF (1 mL). 1-chloro-5-cyanato-2,4-dimethoxybenzene (66.22 mg, 0.31 mol) and Et$_3$N (127 µL, 0.93 mmol) were added. The mixture was stirred overnight at rt. The reaction was transferred to a separatory funnel, and an extraction was done using CH$_2$Cl$_2$ (10 mL) and distilled H$_2$O (5 mL). The aqueous phase and the organic phase were separated, and the aqueous phase was extracted with CH$_2$Cl$_2$ (5 mL). Afterwards, the organic phase was extracted with brine, dried over Na$_2$SO$_4$, filtered and concentrated under vacuum on rotavap. The crude product was purified by silica gel column chromatography (CH$_2$Cl$_2$/methanol 9:1 as eluent and 100 µL Et$_3$N) to obtain 41 in a yield of 18.7% (0.03 g, 0.06 mmol). TLC analysis showed the product to be pure: (CH$_2$C$_2$/methanol 3:1) Rf=0.48.

Synthesis of (2-Chloro-6-methyl-pyrimidin-4-yl)-(9-ethyl-9H-carbazol-3-yl)-amine, HV-118

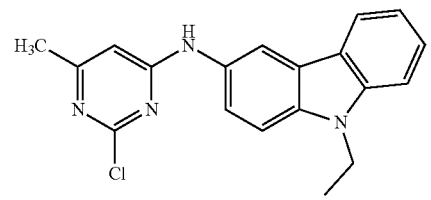 [SMILES: CCn1c2ccccc2c2cc(Nc3cc(C)nc(Cl)n3)ccc21]

In a 250 mL three neck round bottom flask was charged with 1.23 g (7.55 mmol) of 2,4-dichloro-6-methylpyrimidine 6 (previously purified with ethyl acetate), 1.587 g (7.55 mmol) of 3-amino-9-ethylcarbazole 2, and 1.05 mL (7.55 mmol) of triethylamine dissolved in THF. The mixture was stirred for 1 h until all reagents dissolve. Then the solution was refluxed overnight at 76° C. After the reaction was complete (monitored by TLC), water (100 mL) was added, and the product extracted with ethyl acetate (3×40 mL). The combined organic phases were washed with brine and dried over anhydrous Na$_2$SO$_4$ (1 h), filtered, and concentrated under reduced pressure. The crude was purified via column chromatography over silica gel, and the product HV-118 was obtained pure as a yellow solid (0.440 g, 1.31 mmol) in 17% yield. $^1$H NMR (400 MHz, CDCl$_3$) δ 1.43 (3H, t, J=6.40 Hz), 2.40 (s, 3H), 4.36 (q, 2H, J=6.80 Hz), 6.61 (s, 1H), 7.20 (d, 1H, J=1.1 Hz), 7.21 (d, 1H, J=5.93 Hz), 7.38 (d, 1H, J=9.23 Hz), 7.39 (d, 1H, J=9.44 Hz), 7.46 (t, 1H, J=7.04 Hz), 7.60 (d, 1H, J=8.00 Hz), 8.08 (d, 1H, J=7.80 Hz), 8.33 (s, 1H); $^{13}$C NMR (100 MHz, CDCl$_3$) δ 13.8, 23.9, 37.7, 100.1, 108.8, 109.3, 117.8, 119.2, 120.6, 122.3, 123.6, 123.7, 126.4, 128.0, 138.5, 140.5, 160.2, 164.6, 168.5.

Synthesis of N$^4$-(9-Ethyl-9H-carbazol-3-yl)-6-methyl-N$^2$-(3-morpholin-4-yl-propyl)-pyrimidine-2,4-diamine (8)

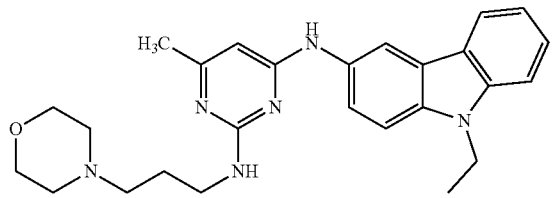 [SMILES: CCn1c2ccccc2c2cc(Nc3cc(C)nc(NCCCN4CCOCC4)n3)ccc21]

In a microwave test tube equipped with a magnetic stirrer, the compound HV-118 (0.0508 g, 0.15 mmol) was dissolved in 2 mL of dioxane. Then, 3-morpholinopropylamine 4 (0.023 mL, 0.16 mmol) and Cs$_2$CO$_3$ (0.1456 g, 0.45 mmol) were added. The mixture was stirred for 1 h until all reagents dissolve completely. The mixture was heated to 160° C. for 2 h. After the reaction was complete (monitored by TLC), water was added (5 mL), and the product extracted with ethyl acetate (4×10 mL). The combined organic phases were washed with brine and dried over anhydrous Na$_2$SO$_4$ (1 h), filtered, and concentrated under reduced pressure. The crude was purified via column chromatography over silica gel, and the product 8 was obtained pure as a pale yellow solid. $^1$H NMR (400 MHz, CDCl$_3$) δ 1.25 (br, 2H), 1.46 (t, 3H, J=7.20 Hz), 1.82 (quin, 2H, J=6.73 Hz), 2.17 (d, 2H, J=4.44 Hz), 2.46 (t, 4H, J=7.08 Hz), 3.48 (q, 2H, J=6.61 Hz), 3.72 (t, 4H, J=4.62 Hz), 4.39 (q, 2H, J=7.20 Hz), 5.76 (s, 1H), 6.87 (br, 1H), 7.23 (d, 1H, J=7.19 Hz), 7.25 (s, 1H), 7.35 (dd, 1H, J=1.90, 8.60 Hz), 7.39 (d, 1H, J=7.76 Hz), 7.42 (d, 1H, J=8.56 Hz), 7.49 (t, 1H, J=8.06 Hz), 8.04 (s, 1H), 8.06 (d, 1H, J=7.59 Hz); $^{13}$C NMR (100 MHz, CDCl$_3$) δ 13.8, 22.9, 26.3, 37.7, 39.9, 53.7, 56.7, 66.9, 92.7, 108.7, 108.9, 116.7, 119.0, 120.5, 122.5, 123.0, 123.4, 126.1, 129.5, 137.9, 140.5, 163.4.

The NMR data for various compounds according to the instant disclosure follows.

Example 2: Synthesis of HV-107 (aka "Compound 11b")

The instant example describes the synthesis of 9-Ethyl-9H-carbazole-3-carboxylic acid (2-morpholin-4-yl-pyridin-3-yl)-amide (aka HV-107 or Compound 11b):

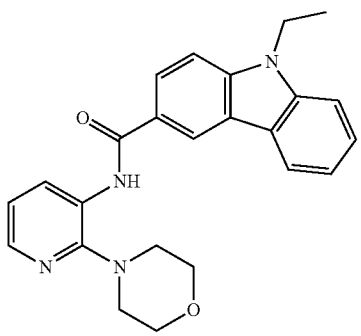 [SMILES: CCn1c2ccccc2c2cc(C(=O)Nc3cccnc3N3CCOCC3)ccc21]

In a 100 mL three-neck round-bottom flask was charged with 2-Morpholin-4-yl-pyridin-3-ylamine derivative 9b (0.180 g, 1.0 mmol), 9-ethyl-9H-carbazole-3-carboxylic acid 10 (0.1196 g, 0.5 mmol), HOBt (0.0675 g, 0.5 mmol), and EDAC (0.0958 g, 0.5 mmol) dissolved in THF (10 mL). The mixture was stirred for 10 min, then Et$_3$N (0.3 mL, 2.0 mmol) was added. The mixture was stirred at room temperature for 16 h. After the reaction was complete (analyzed by TLC), the solution was washed with water (30 mL), and the product was extracted with CH$_2$Cl$_2$ (3×20 mL). The combined organic phases were washed with brine and dried over anhydrous Na$_2$SO$_4$, filtered, and concentrated under reduced pressure. The crude was purified via column chromatography over silica gel and the product 11B was obtained as a white solid (0.1271 g, 0.320 mmol, 32%). TLC analysis in CH$_2$Cl$_2$-MeOH (9:1), Rf=0.93. $^1$HNMR (400 MHz, CDCl3) δ 1.49 (3H, t, J=7.1 Hz), 3.17 (4H, t, J=4.8 Hz), 3.99 (4H, t, J=4.8 Hz), 4.44 (2H, q, J=6.8 Hz), 7.16 (1H, d, J=4.3 Hz), 7.17 (1H, d, J=4.44 Hz), 7.36 (1H, t, J=7.6 Hz) 7.49 (1H, d, J=7.8 Hz), 7.53 (1H, d, J=8.3 Hz), 7.55 (1H, d, J=8.1 Hz), 8.03 (1H, d, J=2.0 Hz), 8.05 (1H, d, J=1.8 Hz) 8.14 (1H, d, J=1.8 Hz), 8.15 (1H, d, J=1.8 Hz), 8.71 (1H, d, J=1.8 Hz), 8.85 (1H, d, J=1.8 Hz) 8.86 (1H, d, J=1.5 Hz), 9.06 (1H, s); 13C NMR (100 MHz, CDCl3) δ 13.8, 37.9, 50.6, 67.6, 108.6, 109.0, 119.9, 120.6, 120.9, 122.8, 123.1, 124.4, 124.8, 126.7, 127.3, 128.7, 140.7, 142.1, 142.4, 152.7, 165.9.

Example 3: Synthesis of HV-118

The instant example describes the synthesis of (2-Chloro-6-methyl-pyrimidin-4-yl)-(9-ethyl-9H-carbazol-3-yl)-amine (aka HV-118):

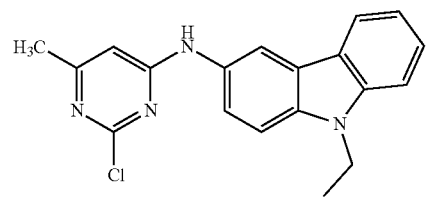 [SMILES: CCn1c2ccccc2c2cc(Nc3cc(C)nc(Cl)n3)ccc21]

In a 250 mL three neck round bottom flask was charged with 1.23 g (7.55 mmol) of 2,4-dichloro-6-methylpyrimidine 6 (previously purified with ethyl acetate), 1.587 g (7.55 mmol) of 3-amino-9-ethylcarbazole 2, and 1.05 mL (7.55 mmol) of triethylamine dissolved in THF. The mixture was stirred for 1 h until all reagents dissolve. Then the solution was refluxed overnight at 76° C. After the reaction was complete (monitored by TLC), water (100 mL) was added, and the product extracted with ethyl acetate (3×40 mL). The combined organic phases were washed with brine and dried over anhydrous Na$_2$SO$_4$ (1 h), filtered, and concentrated under reduced pressure. The crude was purified via column chromatography over silica gel, and the product HV-118 was obtained pure as a yellow solid (0.440 g, 1.31 mmol) in 17% yield. $^1$H NMR (400 MHz, CDCl$_3$) δ 1.43 (3H, t, J=6.40 Hz), 2.40 (s, 3H), 4.36 (q, 2H, J=6.80 Hz), 6.61 (s, 1H), 7.20 (d, 1H, J=1.1 Hz), 7.21 (d, 1H, J=5.93 Hz), 7.38 (d, 1H, J=9.23 Hz), 7.39 (d, 1H, J=9.44 Hz), 7.46 (t, 1H, J=7.04 Hz), 7.60 (d, 1H, J=8.00 Hz), 8.08 (d, 1H, J=7.80 Hz), 8.33 (s, 1H); $^{13}$C NMR (100 MHz, CDCl$_3$) δ 13.8, 23.9, 37.7, 100.1, 108.8, 109.3, 117.8, 119.2, 120.6, 122.3, 123.6, 123.7, 126.4, 128.0, 138.5, 140.5, 160.2, 164.6, 168.5.

Example 4: Scheme 1 Compounds

The growth inhibitory potency against MCF-7 and MDA-Mb-231 breast cancer cells was tested and the resulting data is on Table 1. Among the two series of compounds 3a-d and 4a-f, compounds 4a and 4c-e demonstrate moderate antiproliferative activity with GI50 in the range of 13.4-28.3 pM on MCF-7 cancer cell line. As for MDA-MB-231 cell line, compounds 3d and 4d-e showed GI50 in the range of 18-19.3 µM, and the remaining compounds showed GI above 50 pM. The three-carbon atom aliphatic chain connected between the morpholine group and the pyridine ring, as seen in compound 3d, showed a moderate increase in growth inhibitory potency against MDA-MB-231 cell line. The effect of substituting the amino carbazole at the 2-position of the pyridine ring and amide-linked with primary aliphatic amines at 3-position, as seen for compounds 4a-e, resulted in improved cytotoxicity against both cancer cell lines.

TABLE 1

Growth inhibition and anti-migration activity for compounds 3a-d and 4a-f on MCF-7 and MDA-MB-231 cell lines.

| Cmpd | R = | GI$_{50}$ (µM)$^a$ MCF-7 | MDA-MB-231 | Migration (%)$^{b,c}$ |
|---|---|---|---|---|
| 3a | [piperazine-N-acetyl] | >50 | >50 | 93 ± 11.67 |
| 3b | [morpholine] | >50 | >50 | 68 ± 10.54 |
| 3c | [4-phenylpiperazine] | >50 | >50 | 99 ± 1.89 |
| 3d | [NH-propyl-morpholine] | >50 | 19 | 76 ± 7.87 |
| MBQ-5 | [thiomorpholine] | >50 | >50 | 54 ± 8.75 |
| 4a | [NH-propyl-morpholine] | 28 | >50 | 99 ± 1.28 |
| 4b | [NH-ethyl-piperazine-Boc] | >50 | >50 | 95 ± 9.80 |
| 4c | [NH-propyl-imidazole] | 27 | >50 | 93 ± 2.01 |
| 4d | [NH-CH(CH3)-propyl-N(Et)2] | 13 | 18 | 91 ± 14.10 |
| 4e | [NH-ethyl-N(Et)2] | 14 | 18 | 99 ± 4.12 |

TABLE 1-continued

Growth inhibition and anti-migration activity for compounds 3a-d and 4a-f on MCF-7 and MDA-MB-231 cell lines.

| Cmpd | R = | GI$_{50}$ (μM)[a] MCF-7 | MDA-MB-231 | Migration (%)[b,c] |
|---|---|---|---|---|
| 4f | 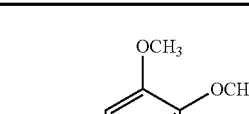 | >50 | >50 | 92 ± 8.55 |
| EHop-016 | | 14 | 15 | 67 ± 7.55 |

[a] GI$_{50}$ = compound concentration required to inhibit MDA-MB-231 proliferation by 50% after 24 h treatment. Values are expressed as the mean of triplicate experiments, and standard deviation (SD) are <10%.
[b] After 24 h, MDA-MB-231 cellular migration was determined by measuring the distance traveled from the edge of the scratch toward the center of the scratch, relative to control.
[c] Percent relative migration values at 10 μM are the average of three independent experiments.

Example 5: Scheme 2 Compounds

To test the effect of reversing the orientation of the amide linkage at position-3 of the pyridine ring, a series 2,3-diamino-substituted pyridine derivatives represented by 7a-c and 11a-b was synthesized (scheme 2). Among the five compounds synthesized, three compounds (7a-b and 11a) exhibited moderate anti-proliferative activity, and for compounds (7c) and (11b) minimal cytotoxicity was observed at concentrations ≤50 μM in MDA-MB-231 cancer cells (see Table 2).

TABLE 2

Growth inhibition and anti-migration activity for compounds 7a-c and 11a-b on MCF-7 and MDA-MB-231 cell lines.

| Cmpd | R = | GI$_{50}$ (μM)[a] MCF-7 | MDA-MB-231 | Migration (%)[b,c] |
|---|---|---|---|---|
| 7a | 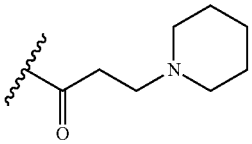 [SMILES: *C(=O)CCN1CCCCC1] | 15 | 23 | 99 ± 4.29 |
| 7b | 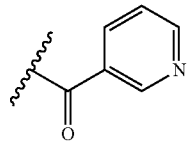 [SMILES: *C(=O)c1cccnc1] | 41 | 31 | 81 ± 11.12 |
| 7c | 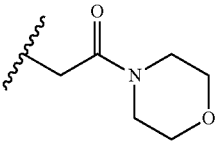 [SMILES: *CC(=O)N1CCOCC1] | 23 | >50 | 81 ± 8.27 |
| 11a | 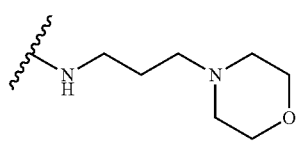 [SMILES: *NCCCN1CCOCC1] | 32 | 39 | 89 ± 10.10 |

TABLE 2-continued

Growth inhibition and anti-migration activity for compounds 7a-c and 11a-b on MCF-7 and MDA-MB-231 cell lines.

| Cmpd | R = | GI$_{50}$ (μM)[a] MCF-7 | MDA-MB-231 | Migration (%)[b,c] |
|---|---|---|---|---|
| 11b (aka HV-107) | —N(morpholine) | >50 | >50 | 66 ± 7.43 |

[a]GI$_{50}$ = compound concentration required to inhibit MDA-MB-231 proliferation by 50% after 24 h treatment. Values are expressed as the mean of triplicate experiments, and standard deviation (SD) are <10%.
[b]After 24 h, MDA-MB-231 cellular migration was determined by measuring the distance traveled from the edge of the scratch toward the center of the scratch, relative to control.
[c]Percent relative migration values at 10 μM are the average of three independent experiments.

The effect of reversing the amide linkage, as with 3d compared with compound 11a, showed no improvement in the growth inhibition potency against MDA-MB-231 cancer cells. Additionally, the effect of replacing the aliphatic amide group at the 3-position with an aromatic ring, was also explored by synthesizing compound 7b. This compound exhibited moderate antiproliferative effect similar to 11a. Within the reverse series, the high anti-migratory activity of compound 11b is comparable to that of 3b, and with the parent compound EHop-016. Addition of a three-carbon atom aliphatic chain linker between the pyridine ring (at the 2-position) and the morpholine group, as for 3d and 11a, results in some loss of anti-migratory activity. Moreover, the effect of 11b was tested on Rac activity, using an ELISA-based Rac activity assay and pulldowns assay. Results show that at 250 nM, 11b inhibits Rac activation by 55% in MDA-MB-231 and MDA-MB-435 cancer cells.

Example 6: Scheme 3 Compounds

By replacing the central pyrimidine core with ortho-diamide building block, as represented in the general synthetic scheme 3, the compounds are forced to adopt a U-shaped conformation, which was hypothesized to lead to enhanced binding to Rac1. Preliminary dockings demonstrated indeed lower binding energies for this class of compounds, and as this implied an increased potency, this was a good reason to synthesize and test a series of ortho-diamide compounds containing the carbazole group, that was strongly correlated with Rac1 inhibitory activity. Utilizing three different anhydride building blocks, the ortho-amidocarboxylic acids 14a-h were synthesized as represented in scheme 3 via a simple nucleophilic ring-opening reaction of the cyclic anhydrides 12 with 3-amino-9-ethyl-carbazole 2. After acidic work-up, extraction and removal of the solvent, the desired products 13 could be obtained essentially pure in yields of 48 to 78%. Each of the ortho-amide carboxylic acids 13 was reacted with a variety of amines in order to obtain the ortho-diamide products 14a-h in yields of 43 to 62%.

An in vitro analysis demonstrated that the ortho-diamide derivatives did not show growth inhibition in MCF-7 and MDA-MB-231 cell lines (see Table 3). Hence, these specific derivatives are not viable anti-cancer therapeutic agents. Furthermore, the ortho-diamide derivatives were studied for anti-migratory effects using the wound-healing assay in MDA-MB-231 cell line. After 24 h of treatment at 10 μM, no migration inhibition could be seen. In general, these SAR results further demonstrate that for anti-migratory potency in this series of compounds, a morpholine-like substituent is preferred at position-2 of the pyridine ring with the carbazole group linked with an amide at position-3.

TABLE 3

Growth inhibition and anti-migration activity for compounds 14a-h on MCF-7 and MDA-MB-231 cell lines.

| Cmpd | R = | X-ring | GI$_{50}$ (μM)[a] MCF-7 | MDA-MB-231 | Migration (%)[b,c] |
|---|---|---|---|---|---|
| 14a | —NH—CH$_2$CH$_2$—N(morpholine) | pyrazine | >50 | >50 | 91 ± 5.23 |
| 14b | —NH—CH$_2$CH$_2$CH$_2$—N(morpholine) | | >50 | >50 | 94 ± 5.87 |

TABLE 3-continued

Growth inhibition and anti-migration activity for compounds 14a-h on MCF-7 and MDA-MB-231 cell lines.

| Cmpd | R = | GI$_{50}$ (μM)$^a$ MCF-7 | GI$_{50}$ (μM)$^a$ MDA-MB-231 | Migration (%)$^{b,c}$ |
|---|---|---|---|---|
| 14c | —NH—CH$_2$CH$_2$CH$_2$—(imidazol-1-yl) | >50 | >50 | 99 ± 4.50 |
| 14d | —NH—CH$_2$CH$_2$—O—CH$_3$ | >50 | >50 | 100 ± 5.20 |
| 14e | —NH—CH$_2$CH$_2$—O—CH$_3$ (with benzo-fused ring) | >50 | >50 | 99 ± 2.57 |
| 14f | —NH—CH$_2$CH$_2$—OH | >50 | >50 | 98 ± 1.83 |
| 14g | —NH—CH$_2$CH$_2$—morpholinyl (with cyclohexyl-fused ring) | >50 | >50 | 99 ± 1.63 |
| 14h | —NH—CH$_2$CH$_2$CH$_2$—morpholinyl | >50 | >50 | 100 ± 0.56 |

$^a$GI50 = compound concentration required to inhibit MDA-MB-231 proliferation by 50% after 24 h treatment. Values are expressed as the mean of triplicate experiments, and standard deviation (SD) are <10%.
$^b$After 24 h, MDA-MB-231 cellular migration was determined by measuring the distance traveled from the edge of the scratch toward the center of the scratch, relative to control.
$^c$Percent relative migration values at 10 μM are the average of three independent experiments.

Example 7: Sulforhodamine B (SRB) Assay

Various compounds were tested to evaluate the dose response curve for effect on MCF-7 cancer cells and MDA-MB-231 cancer cells. MCF-7 and MDA-MB-231 cells were cultured in 10% Minimum Essential Medium Eagle (MEME) supplemented with Earle's Balanced Salt Solution (EBSS), Non-essential Amino acids (NEAA), Sodium pyruvate, Pen/Strep, L-glutamine and Fetal Bovine Serum (FBS) at 37° C. in 5% CO$_2$.

Sulforhodamine B (SRB) Assay: A stock solution of compounds was prepared at 50 mM in 100% DMSO. For cells preparation, a flask of 75 cm$^2$ or 25 cm$^2$ were used for 2.6×10$^5$ cells or 1.44×10$^5$ cells respectively with an 80-90% of confluence. Cells were washed with PBS and trypsinized. The concentration of cells was determined using a 1:2 dilutions with Trypan Blue and a hemocytometer. After cell count, the concentration was adjusted to have a 1.9×10$^4$ cells/well. Approximately 100 μM of cells suspension, compounds, control positive and control negative were added in triplicates to a 96 well plate. Positive controls used were ellipticine, doxorubicin, and/or vincristine, and the negative control was DMSO 0.1%. All compounds at 50, 25, 12.5, 6.3, and 1.6 μM were incubated with cells at 37° C. for 24 hrs. For fixation, cold TCA 50% was used and incubated at 4° C. for 1 hr. Wells were washed and dried prior to tincture with 100 μL of SRB 0.4%. To remove excess of SRB, acetic acid was used. For analysis, TRIS-BASE Solution (pH=10.5) was used and shacked prior to reading using an ELISA reader at 510 nm and the software SoftMax Pro 4.8.

Figure 4A:
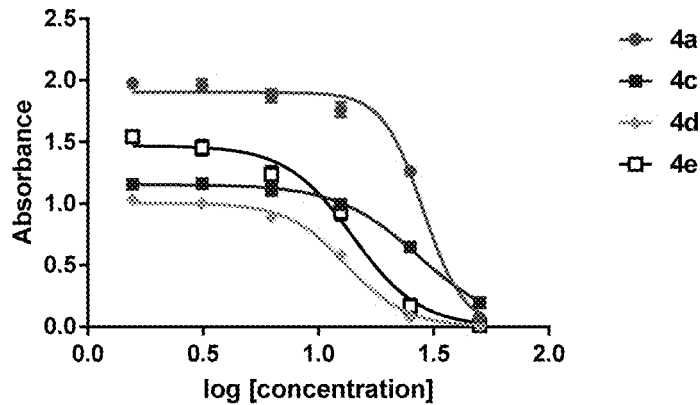
FIG. 4 (A-B). Log-dose response curve for compounds 4a, 4c, 4d, 4e (FIG. 4A), 7a, 7c, and 11a (FIG. 4B) in MCF-7 cancer cells. Each data point represents the mean of three (3) replicates, error bars represent 95% confidence intervals. Each GI$_{50}$ was calculated based on sigmoidal curve fitting to the respective data set.
Figure 4B:
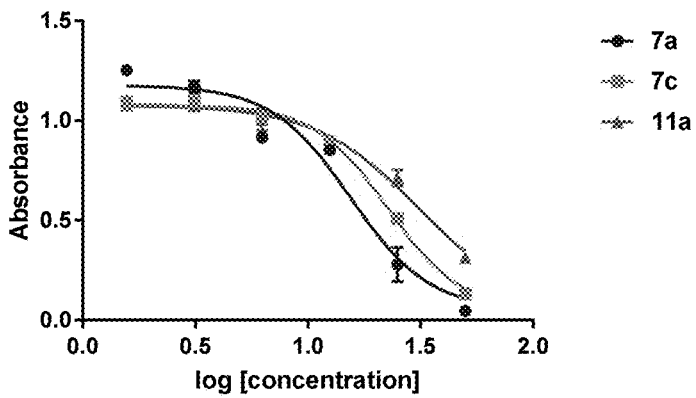
Figure 5A:
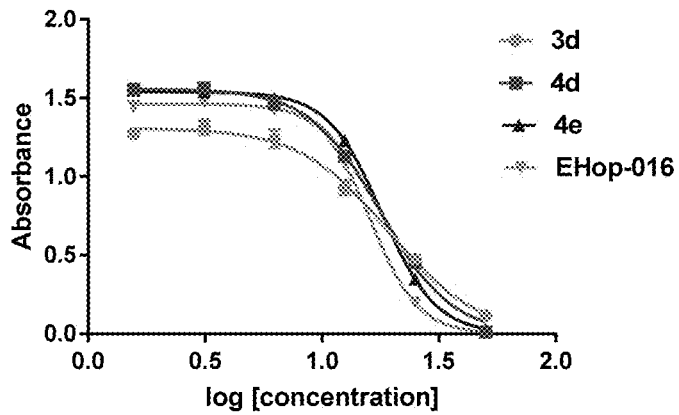
FIG. 5 (A-B). Log-dose response curve for compounds 3d, 4d, 4e (FIG. 5A), 7a, 7b, and 11a (FIG. 5B) in MDA-MB-231 cancer cells. Each data point represents the mean of three (3) replicates, error bars represent 95% confidence intervals. Each GI$_{50}$ was calculated based on sigmoidal curve fitting to the respective data set.
Figure 5B:
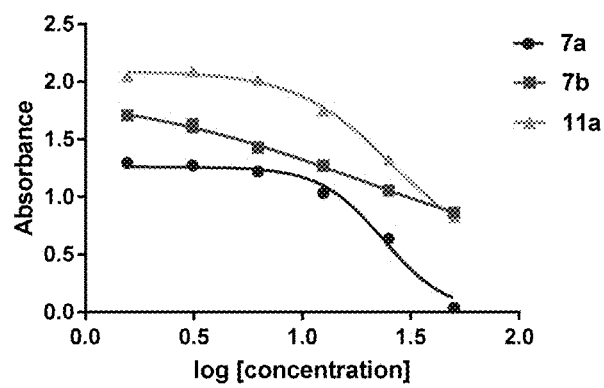

For each compound, 50% growth inhibition (GI$_{50}$) was calculated from Sigmoidal dose-response curves (variable-slope) that were generated with data obtained from experiments carried out in triplicates (GI$_{50}$ values were generated with GraphPad Prism V. 6.02, GraphPad Software, Inc.). The results are presented in FIGS. 4A-4B (MCF-7 cancer cells) and FIGS. 5A-5B (MDA-MB-231 cancer cells).

Example 8: Wound Healing Assay (Scratch Method)

Figure 6:
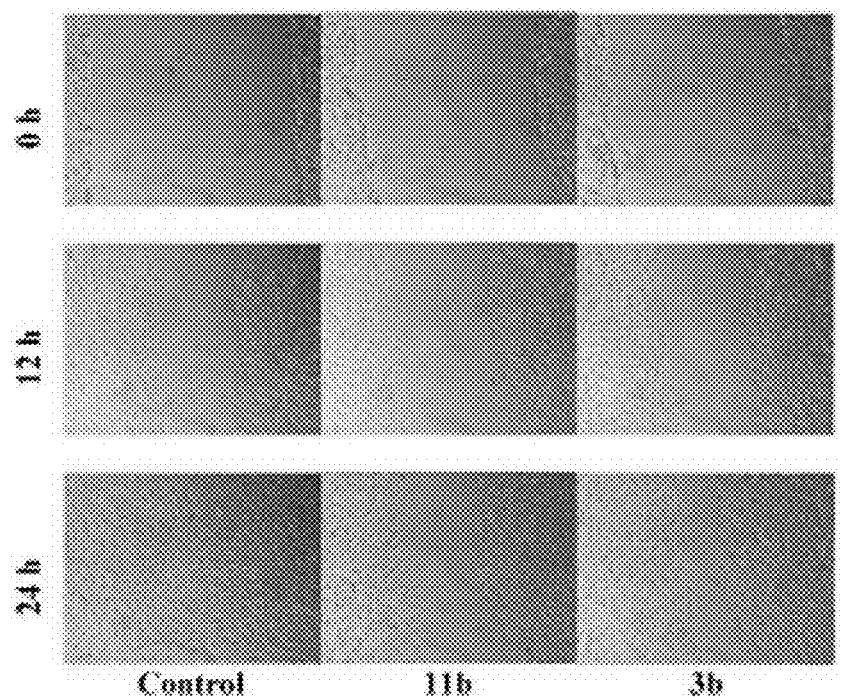
FIG. 6. Wound Healing Assay. Inhibitory effect of 11b and 3b on MDA-MB-231 cells migration detected by wound-healing assay. MDA-MB-231 cells were treated with vehicle or with 11b and 3b at 10 pM and photomicrograph obtained at 0, 12, and 24 h.

The experimental data of anti-migratory activities for compounds 3a-d and 4a-f were obtained using MDA-MB-231 breast cancer cells. Results are summarized in Table 1 above. For the migration assay, a wound-healing assay (scratch-wound assay) was utilized in the presence of vehicle (0.02% DMSO) or compounds at 10 pM. FIG. 6 shows the results of the migration assay.

Among the eleven compounds synthesized and examined, two compounds 3b and 3d exhibited 32% and 24% antimigratory activity, respectively. However, compounds 3a, 3c, and 4a-f inhibited migration in the range of 1-9%. Using the same experimental conditions to determine the anti-migratory potential, the parent compound EHop-016 exhibited anti-migratory activity of 33% at 10 pM and 17% at 5 pM. Despite the fact that compound 3b showed minor anti-proliferative activity against MDA-MB-231 at <50 pM, the compound exhibited comparable anti-migratory activity with the parent EHop-016. However, EHop-016 has been demonstrated that at concentrations >10 pM reduce cell viability in MCF10A mammary epithelial cell lines.

Prior to assays, cells were grown until 80-90% confluence was observed. A 75 cm2 flask was used for $2.6 \times 10^5$ cells/mL in 10 mL and for a 25 cm2 flask $1.44 \times 10^5$ cells/mL in 5 mL. The cells were washed with PBS to remove all traces of FBS. 2 mL was added for a 25 cm2 flasks or 4 mL for a 75 cm2 flasks trypsin, and incubated 5-10 min at 37° C. At the end of the incubation time, cells were re-suspended and counted with hemocytometer using 1:2 dilutions with Trypan blue. Subsequently, cell viability was calculated. In a 12 multiwell plate, the plastic pattern was used to draw a fine space with a fine marker on the bottom of the plate. Cells were seeded at $1.5$-$2.2 \times 10^5$ cells/mL in 1 mL and incubated for 24 h. Cells were then rinsed with PBS and incubated in starving media (0.5% FBS) overnight. All controls and drugs were tested in triplicate. The negative control for each drug was prepared according to the drug's DMSO concentration.

Drugs were diluted and the final concentration at each well was 10 pM. The wound was made using a sterile pipette tip of 200 pL. Cells were then rinsed very gently with media without FBS and media with negative controls was added. After a 24 h incubation, the gap distance was evaluated using the software Lumera Infinity Analyze 6.4.0. Pictures were taken at 0, 8, 12 and 24 h using a 10× objective. The percentage of migration was calculated using the following formula:

$100 - [(X_0/\bar{X}_0)] * 100$ for time 0 h measurements $100 - [(X_{24}/\bar{X}_0)] * 100$ for time 24 h measurements The experimental data of anti-migratory activities for compounds 3a-d and 4a-f were obtained using MDA-MB-231 breast cancer cells, and results are summarized in Table 1. For the migration assay, we used a wound-healing assay (scratch-wound assay)[22] in the presence of vehicle (0.02% DMSO) or compounds at 10 μM (FIG. 6). Among the ten compounds synthesized and examined, two compounds 3b and 3d exhibited 32% and 24% anti-migratory activity, respectively (Table 1). However, compounds 3a, 3c, and 4a-f inhibited migration in the range of 1-9%. Using the same experimental conditions to determine the anti-migratory potential, the parent compound EHop-016 exhibited anti-migratory activity of 33% at 10 μM and 17% at 5 μM. Despite the fact that compound 3b showed no anti-proliferative activity against MDA-MB-231 at ≤50 μM, the compound exhibited comparable anti-migratory activity with the parent EHop-016. However, EHop-016 has been demonstrated that at concentrations ≥10 μM reduce cell viability in MCF10A mammary epithelial cell lines.

Example 9: Molecular Docking Assay

All compounds were drawn using ChemDraw Ultra 7.0 and energy-minimized with MOPAC AM1 inChem3D Ultra 7.0. All fdes were saved as pdb file format. For molecular docking, Autodock 4.0 with Autodock Tools 1.5.4 as a graphical interface was used. The PDB files of the Rac1 protein were obtained from the Protein Data Bank (PDB). For instance, the Rac1-Tiam complex (code: foe pdb) X-ray structure was used for the study. The Tiam structure, water, metals, and any other molecule that is not part of the protein were removed. The network of amino acids inside or surrounding Trp56 of Rac1 were set to be rigid. The grid box coordinates were located at the center of Trp56. The AutoDock Tools program was used to prepare the GEF-interacting region of Rac1 and the compounds for docking using 40×40×40 Å with a grid spacing of 0.375 Å, and a flexible docking of 50 GA runs. The population size was set to 150 and the maximum number of energy evaluation was set to 2,500,000.

The EHop-016 is a flexible molecule that can adopt different conformations and interact with Rac1 in multiple conformations within the GEF-RacI site. Nevertheless, in docking studies the most favorable conformation that adopts EHop-016 in Rac1 is in a "U-bent" conformation. Docking of compound 11b with Rac1 shows the morpholine group and the pyridine ring in close contact with residues Val36 and Asp38. Moreover, the carbazole moiety points toward the hydrophobic pocket created by Val36 and Ala59. Docking of compound 3b positions the morpholine group deep into the pocket of Rac binding site and in close contact to Trp56. The pyridine ring forms hydrogen bonding with the peptide backbone of Asp38 and Asn39.

Example 10: Effect of HV-107 on Cell Viability

Figure 7:
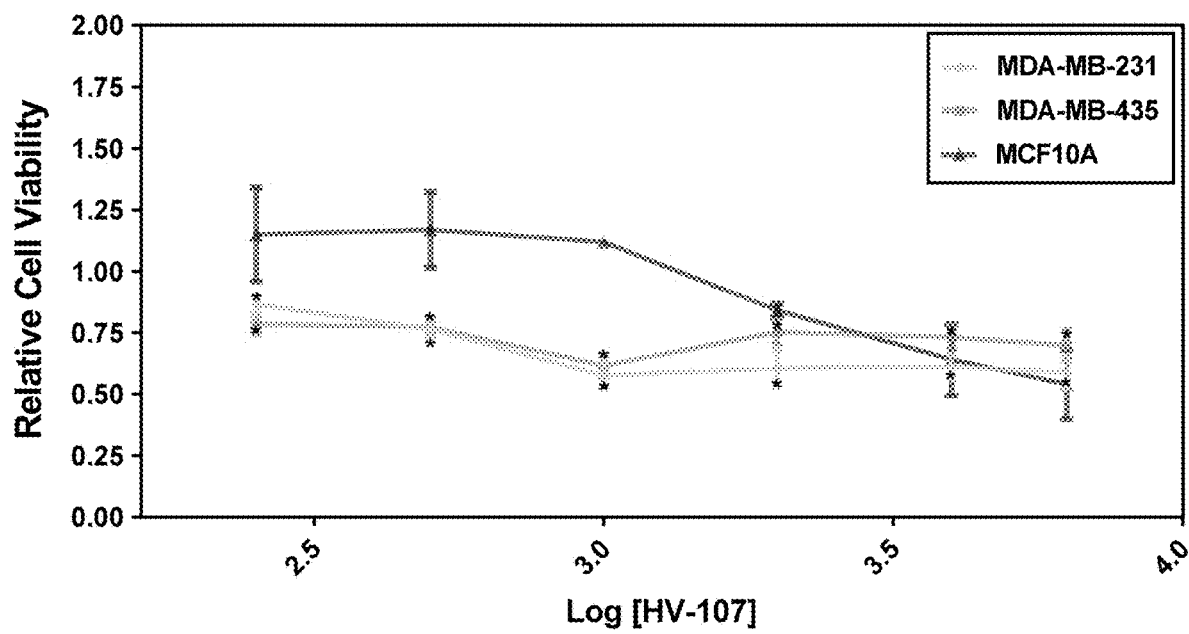
FIG. 7. Effect of HV-107 on cell viability. Cells were treated with vehicle control (0.5% DMSO) or varying concentrations of HV-107 (250-6000 nM) for 48 h. Cell viability was measured using the CellTiter 96® AQueous One Solution Cell Proliferation Assay from Promega, as per manufacturer's instruction. Relative cell viability is presented for non-cancerous mammary epithelial cells (MCF10A) or metastatic breast cancer cells MDA-MB-231 or MDA-MB-435. N=3-4, each with three technical replicates; Error bars represent ±SEM; * p≤0.05.

HV-107 significantly inhibited the viability of MDA-MB-231 and MDA-MB-435 cells at ≥500 nM, while showing minimal toxicity towards MCF10A cells. Cells were treated with ehicle control (0.5% DMSO) or varying concentrations of HV-107 (250-8000 nM) for 24 or 48 h. Cell viability was measured using the CellTiter 96® AQueous One Solution Cell Proliferation Assay from Promega, as per manufacturer's instruction. Relative cell viability is presented for non-cancerous mammary epithelial cells MCF10A (FIG. 7) or metastatic breast cancer cells MDA-MB-231 or MDA-MB-435. N=3, each with three technical replicates; Error bars represent ±SEM; * p≤0.05.

Example 11: Effect of HV-107 on Rac Activation

The effects of HV-107 on the inhibition of Rac activation were tested by pulldown assays.

Figure 8A:
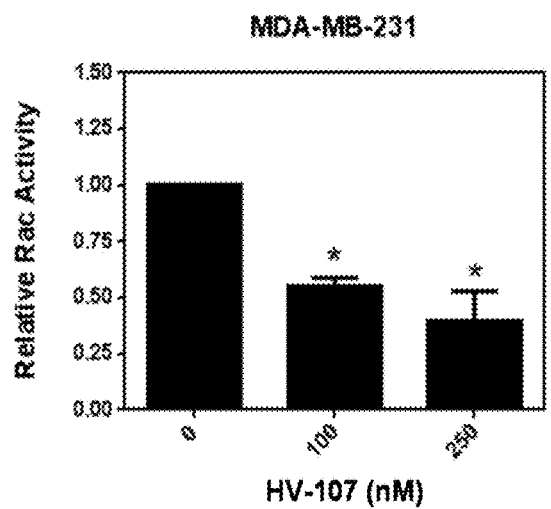
FIG. 8A. MDA-MB-231 and FIG. 8B. MDA-MB-435 human breast cancer cells were treated for 24 h with 0, 100, or 250 nM HV-107. After treatment, total protein was extracted and equal amounts of proteins subjected to pulldown assays using the p21-binding domain of PAK to isolate the GTP bound (active) Rac. Samples were then western blotted for total and active Rac and positive bands quantified using image J. N=2; error bars represent ±SEM; * p≤0.05.
Figure 8B:
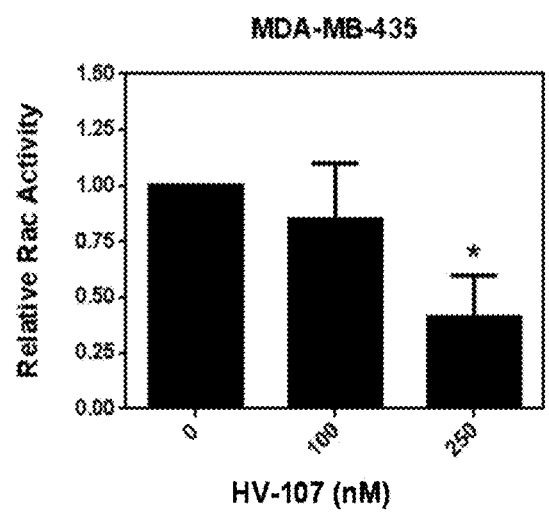
FIG. 8 (A-B). Effect of HV-107 on Rac activation.

In FIG. 8A and FIG. 8B, human breast cancer cells MDA-MB-231 and MDA-MB-435, respectively, were treated for 24 h with 0, 250, or 500 nM HV-107. After treatment, total protein was extracted and equal amounts of proteins subjected to pulldown assays using the p21-binding domain of PAK to isolate the GTP bound (active) Rac. Samples were then western blotted for total and active Rac and positive bands quantified using image J. N=2; error bars represent ±SEM; * p≤0.05.

Results show that at 250 nM, HV-107 inhibits Rac activation by 60%. Therefore, HV-107 significantly inhibits Rac activation in metastatic breast cancer cells with approximately 4× higher efficiency when compared to the lead compound Ehop-016.

Example 12: Effect of HV-118 on Cell Viability

Figure 9:
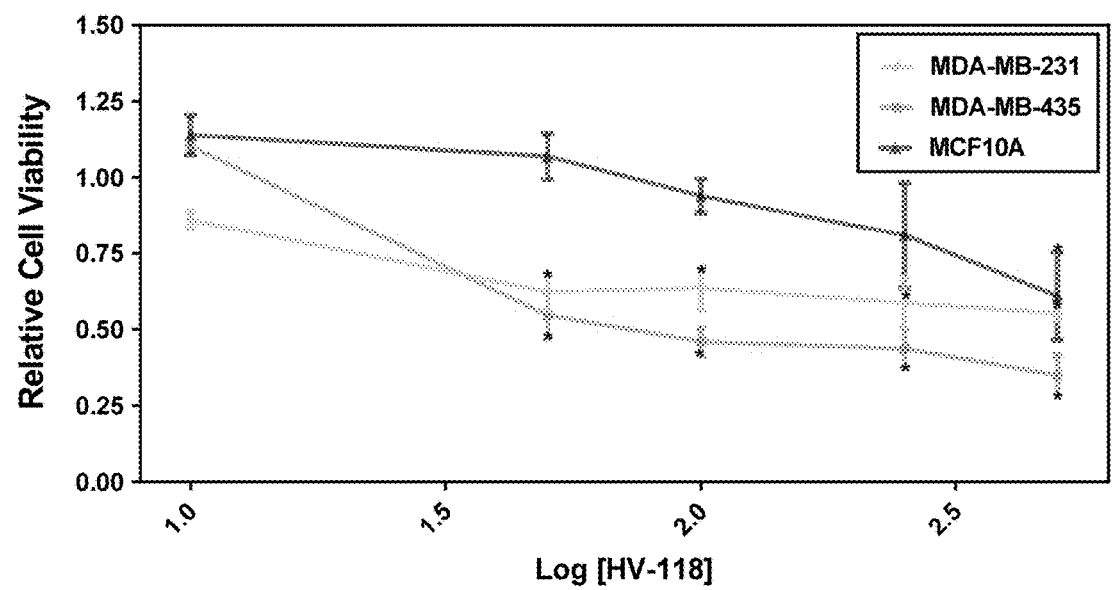
FIG. 9. Effect of HV-118 on cell viability. Cells were treated with vehicle control (0.5% DMSO) or varying concentrations of HV-118 (10-500 nM) for 48 h. Cell viability was measured using the CellTiter 96® AQueous One Solution Cell Proliferation Assay from Promega, as per manufacturer's instruction. Relative cell viability is presented for human non-cancerous mammary epithelial cells (MCF10A) or human metastatic breast cancer cells MDA-MB-231 or MDA-MB-435. N=3, each with three technical replicates; error bars represent ±SEM; * p≤0.05.

Similarly, HV-118 significantly inhibited the viability of MDA-MB-231 and MDA-MB-435 cells at ≥50 nM, and had minimal effects on MFC10A cell viability. Cells were treated with vehicle control (0.5% DMSO) or varying concentrations of HV-118 (10-500 nM) for 48 h. Cell viability was measured using the CellTiter 96® AQueous One Solution Cell Proliferation Assay from Promega, as per manufacturer's instruction. Relative cell viability is presented for human non-cancerous mammary epithelial cells MCF10A (FIG. 9) or human metastatic breast cancer cells MDA-MB-231 or MDA-MB-435. N=3, each with three technical replicates; error bars represent ±SEM; * p≤0.05.

Example 13: Effect of HV-118 on Rac Activation

The effects of HV-118 on the inhibition of Rac activation were tested by pulldown assays.

Figure 10A:
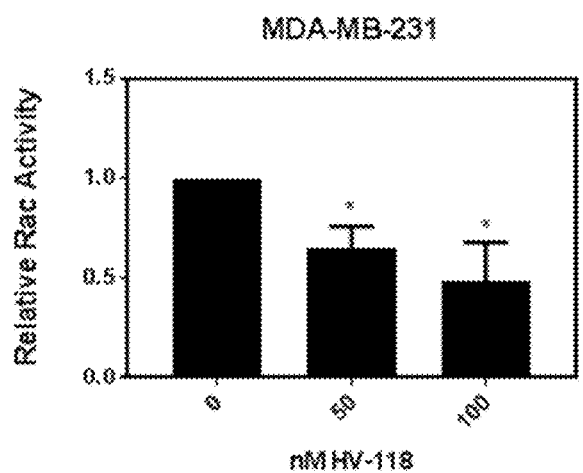
FIG. 10A. MDA-MB-231 and FIG. 10B. MDA-MB-435 human breast cancer cells were treated for 24 h with 0, 25, 50, or 100 nM HV-118. After treatment, total protein was extracted and equal amounts of proteins subjected to pulldown assays using the p21-binding domain of PAK to isolate the GTP bound (active) Rac. Samples were then western blotted for total and active Rac and positive bands quantified using image J. N=3-6; error bars represent ±SEM; * p≤0.05.
Figure 10B:
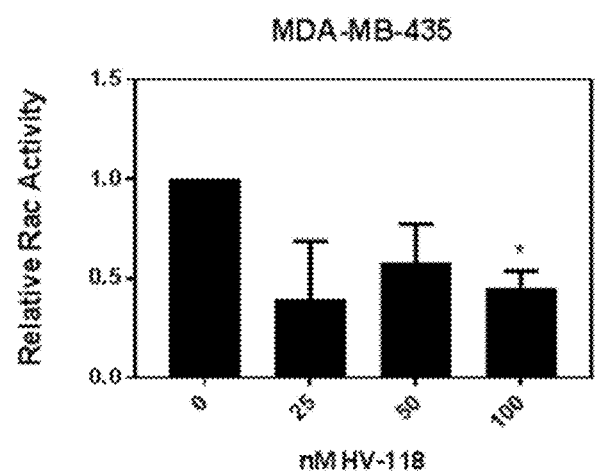
FIG. 10 (A-B). Effect of HV-118 on Rac activation.

In FIG. 10A and FIG. 10B, human breast cancer cells MDA-MB-231 and MDA-MB-435, respectively, were treated for 24 h with 0, 25, 50, or 100 nM HV-118. After treatment, total protein was extracted and equal amounts of proteins subjected to pulldown assays using the p21-binding domain of PAK to isolate the GTP bound (active) Rac. Samples were then western blotted for total and active Rac and positive bands quantified using image J. N=3-6; error bars represent ±SEM; * p≤0.05.

Results show that at HV-118 has a similar effect at 100 nM in MDA-MB-231 and MDA-MB-435 cells. Therefore, HV-118 significantly inhibits Rac activation in metastatic breast cancer cells with approximately 10× higher efficiency when compared to the lead compound Ehop-016.

Figure 11A:
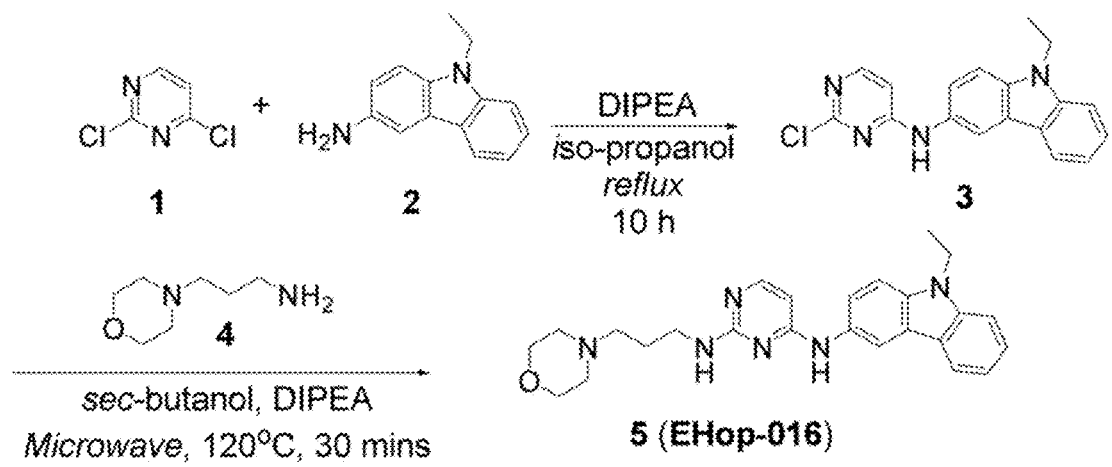
FIG. 11A shows Scheme 1B, a two-step synthetic procedure for the synthesis of EHop-016 and derivatives.

Example 14: Synthesis of EHop-016 Derivatives with Modifications in Building Block C For the synthesis of EHop-016 derivatives with modifications in building block C, an optimized procedure for the synthesis of EHop-016 was utilized (see U.S. Pat. No. 8,884,006, herein incorporated in its entirety). FIG. 11A describes Scheme 1B, a two-step synthetic procedure for the synthesis of EHop-016 and derivatives. The two-step synthetic scheme starts in "step a" with the synthesis of EHop-014 (3) from dichloropyrimidine (1) and 3-amino-9-ethyl-carbazole (2). In the optimized procedure, first dichloropyrimidine as obtained from the supplier, is purified by slurrying in ethyl acetate for one hour. Insoluble solids (hydrolyzed impurities) are filtered and the ethyl acetate is removed via rotary evaporation. Subsequently, purified 1 is reacted with carbazole 2 via reflux in tetrahydrofuran in the presence of 1.2 equivalents triethyl amine. Compared with the previous method, workup was simplified by addition of water and ethyl acetate, which led to the precipitation of 3. Filtration over a Buchner funnel provided compound 3 without column chromatography as essentially the single 4-substituted regioisomer in a yield of 52.1%. Reaction of product 3 with different amines representing building block C, in the presence of either cesium carbonate or triethylamine amine in dioxane or dimethyl sulfoxide under microwave heating at 120 to 160° C. (step b) provided the desired EHop-016 derivatives. A summary of the products synthesized, together with their yields is provided in Table 4.

TABLE 4

Derivatives of EHop-016 with modifications in building block C synthesized via Scheme 1B and Scheme 2B.

| Entry# | Building block C | Reaction conditions | Product | Yield (%) |
|---|---|---|---|---|
| 1 | H₂N~~~N(morpholine) | 1,4-Dioxane Cs₂CO₃ Reflux 120 to 160° C. | EHop-016 | 52.1 |
| 2 | H₂N-CH(CH₃)-CH₂CH₂-N(Et)₂ | DMSO Cs₂CO₃ MW 120° C. for 6 h | (carbazole-pyrimidine-NH-CH(CH₃)CH₂CH₂N(Et)₂) | 21.8 |

TABLE 4-continued

Derivatives of EHop-016 with modifications in building block C synthesized via Scheme 1B and Scheme 2B.

| Entry# | Building block C | Reaction conditions | Product | Yield (%) |
|---|---|---|---|---|
| 3 | 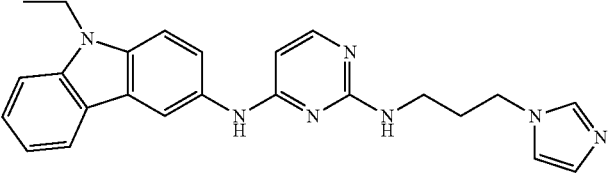 [SMILES: CCn1c2ccccc2c2cc(Nc3ccnc(NCCCn4ccnc4)n3)ccc21] | DMSO Cs₂CO₃ MW 160° C. for 3 h | 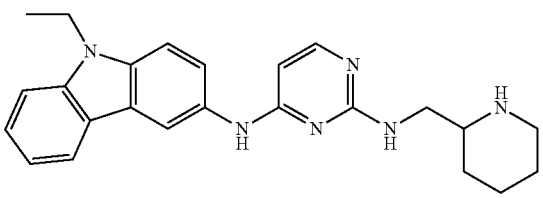 [SMILES: CCn1c2ccccc2c2cc(Nc3ccnc(NCC4CCCCN4)n3)ccc21] 33 | 41.7 |
| 4 | 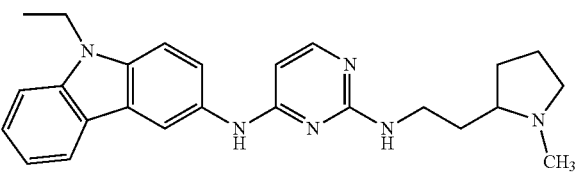 [SMILES: CCn1c2ccccc2c2cc(Nc3ccnc(NCCC4CCCN4C)n3)ccc21] | 1,4-Dioxane Cs₂CO₃ MW 160° C. for 3 h | 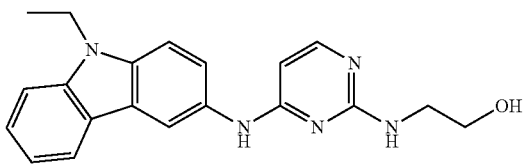 [SMILES: CCn1c2ccccc2c2cc(Nc3ccnc(NCCO)n3)ccc21] 34 | 16.1 |
| 5 | 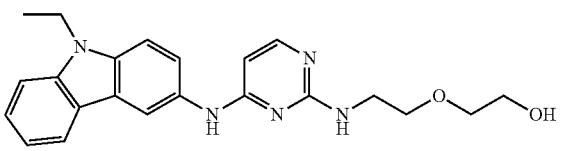 [SMILES: CCn1c2ccccc2c2cc(Nc3ccnc(NCCOCCO)n3)ccc21] | DMSO Cs₂CO₃ MW 120° C. for 6 h | 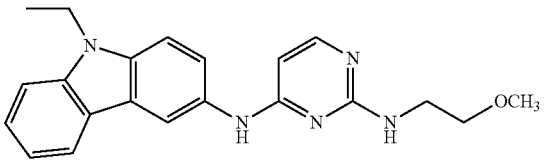 [SMILES: CCn1c2ccccc2c2cc(Nc3ccnc(NCCOC)n3)ccc21] 35 | 31.1 |
| 6 | H₂N⌒OH | 1,4-Dioxane DIPEA MW 160° C. 4-6 hrs | 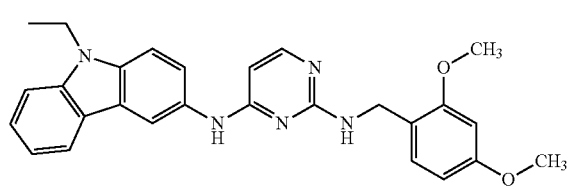 [SMILES: CCn1c2ccccc2c2cc(Nc3ccnc(NCc4ccc(OC)cc4OC)n3)ccc21] 36 | 23.1 |
| 7 | H₂N⌒O⌒OH | 1,4-Dioxane DIPEA MW 160° C. 4-6 hrs | 37 | 50.1 |
| 8 | H₂N⌒OCH₃ | 1,4-Dioxane DIPEA MW 160° C. 4-6 hrs | 38 | 58.9 |
| 9 | 2,4-dimethoxybenzylamine | 1,4-Dioxane DIPEA MW 160° C. 4-6 hrs | 39 | 25.2 |

TABLE 4-continued

Derivatives of EHop-016 with modifications in building block C synthesized via Scheme 1B and Scheme 2B.

| Entry# | Building block C | Reaction conditions | Product | Yield (%) |
|---|---|---|---|---|
| 10 | 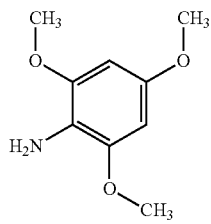 | 1,4-Dioxane DIPEA MW 160° C. 4-6 hrs | 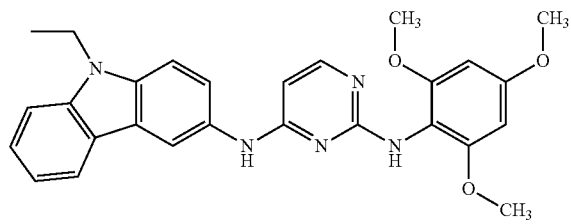 [SMILES: CCn1c2ccccc2c2cc(Nc3ccnc(Nc4c(OC)cc(OC)cc4OC)n3)ccc21]<br>40 | 60.9 |
| 11 | 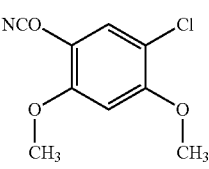 | Et₃N THF Stir, rt overnight | 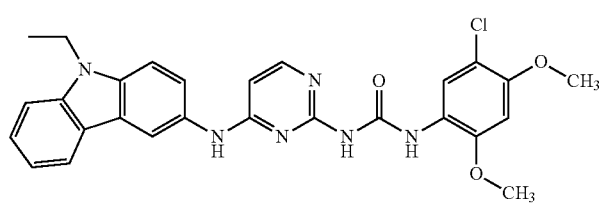 [SMILES: CCn1c2ccccc2c2cc(Nc3ccnc(NC(=O)Nc4cc(Cl)c(OC)cc4OC)n3)ccc21]<br>41 | 18.7 |

Figure 11B:
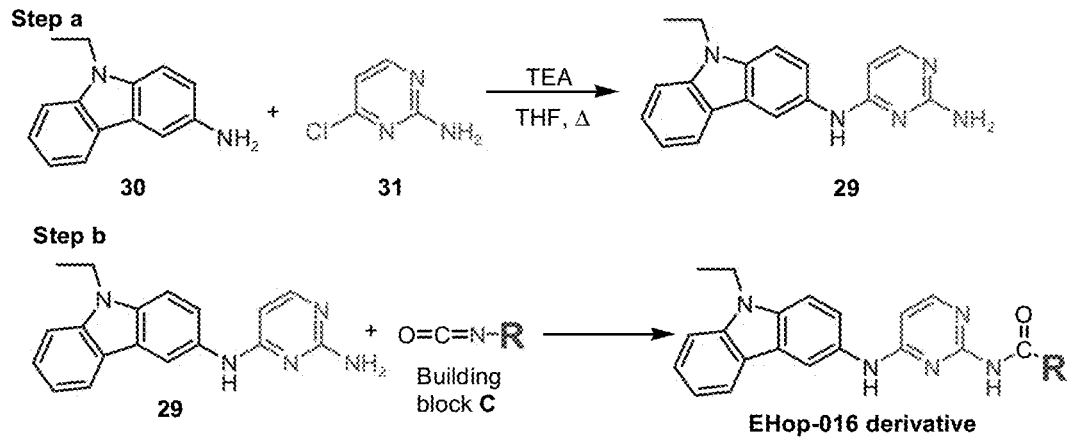
FIG. 11B shows Scheme 2B, a procedure for the synthesis of additional EHop-016 derivatives.

An additional example of a compounds with modification in building block C was synthesized via a different procedure as represented in Scheme 2B (see FIG. 11B). The compounds that were synthesized were tested for their biological activity by determination of their cytotoxicity in MDA-MB-231 breast cancer cell lines as shown in Table 5. The cytotoxicity's are expressed as $IC_{50}$, which indicates the concentration at which 50% of the cell growth is inhibited. Furthermore, the inhibition of cell migration was tested at a concentration of $0.2 \times IC_{50}$, or, when the $IC_{50}$ was >50 µM at a concentration of 10 µM. For comparison, Table 5 also includes the Lipinski and drug-likeness parameters as calculated via the MolSoft platform.

TABLE 5

Biological activity and physicochemical parameters of EHop-016 and compounds and 2-11.

| Entry # | Compound Structure | $IC_{50}$ (µM) | Migration (%) | MW (g/mol) | MolLogP | Number of HBA | Number of HBD | Drug likeness |
|---|---|---|---|---|---|---|---|---|
| 1 | 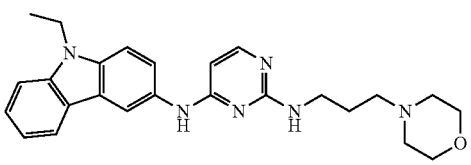 [SMILES: CCn1c2ccccc2c2cc(Nc3ccnc(NCCCN4CCOCC4)n3)ccc21]<br>EHop-016 | 15.74 | 63.36 (5 µM) 95.36 (1 µM) | 430.55 | 4.62 | 4 | 2 | 0.51 |
| 2 | 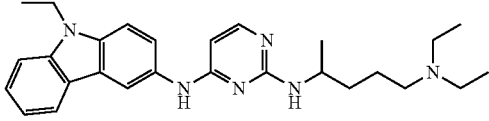 [SMILES: CCN(CC)CCCC(C)Nc1nccc(Nc2ccc3c(c2)c2ccccc2n3CC)n1]<br>32 | 9.00 | 99.87 (1.8 µM) | 444.30 | 6.60 | 3 | 2 | 0.60 |
| 3 | 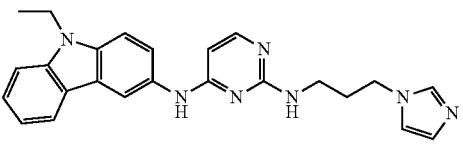 [SMILES: CCn1c2ccccc2c2cc(Nc3ccnc(NCCCn4ccnc4)n3)ccc21]<br>33 | 7.57 | 100.12 (1.51 µM) | 411.22 | 4.35 | 3 | 2 | −0.25 |

TABLE 5-continued

Biological activity and physicochemical parameters of EHop-016 and compounds and 2-11.

| Entry # | Compound Structure | IC$_{50}$ (μM) | Migration (%) | MW (g/mol) | MolLogP | Number of HBA | Number of HBD | Drug likeness |
|---|---|---|---|---|---|---|---|---|
| 4 | 34 | 1.97 | 100.45 (0.39 μM) | 400.24 | 4.74 | 3 | 3 | 0.47 |
| 5 | 35 | 19.13 | 89.13 (3.8 μM) | 414.25 | 5.36 | 3 | 2 | 0.37 |
| 6 | 36 | 14.61 | 94.85 (2.92 μM) | 347.41 | 3.74 | 3 | 3 | −0.39 |
| 7 | 37 | >50 | 100.39 (3.07 μM) | 391.47 | 3.56 | 4 | 3 | −0.23 |
| 8 | 38 | >50 | 96.74 (2.8 μM) | 453.51 | 6.13 | 4 | 2 | 0.02 |
| 9 | 39 | >50 | 102.95 (0.92 μM) | 361.44 | 4.32 | 3 | 2 | −0.25 |
| 10 | 40 | 7.7 | 80.15 (1.54 μM) | 469.53 | 6.10 | 5 | 2 | 0.06 |

TABLE 5-continued

Biological activity and physicochemical parameters of EHop-016 and compounds and 2-11.

| Entry # | Compound Structure | IC$_{50}$ (μM) | Migration (%) | MW (g/mol) | MolLogP | Number of HBA | Number of HBD | Drug likeness |
|---|---|---|---|---|---|---|---|---|
| 11 | 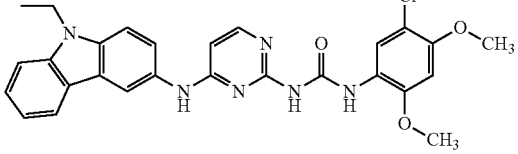 41 | 10.9 | 77.34 (1 μM) | 516.98 | 6.35 | 5 | 3 | 0.24 |

Example 15: Migration Assays for Compounds 5, 10, and 11 Compared to EHop-016

Figure 12A:
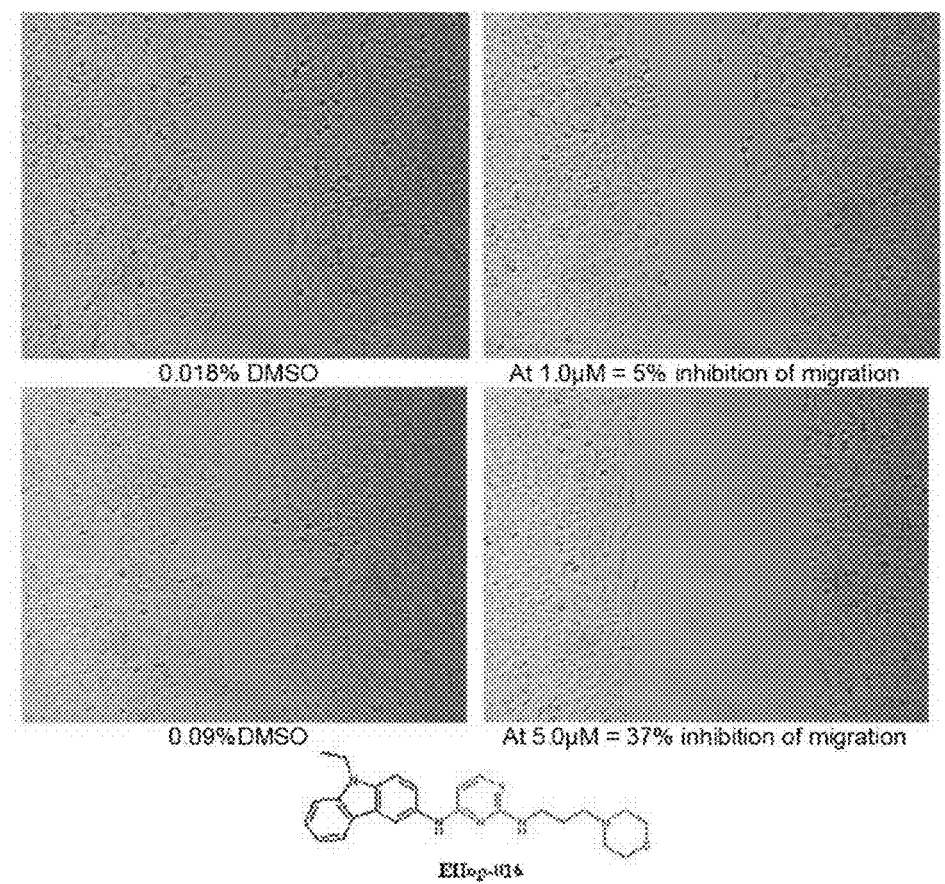
FIG. 12A shows photographs obtained with EHop-016 at concentrations of 1.0 and 5.0 μM.

Migration assays were performed via the Scratch Method as described previously. To illustrate a typical result, FIG. 12A shows photographs obtained with EHop-016 at concentrations of 1.0 and 5.0 μM, which demonstrates inhibition of migration of 5% and 37%, respectively.

Figure 12B:
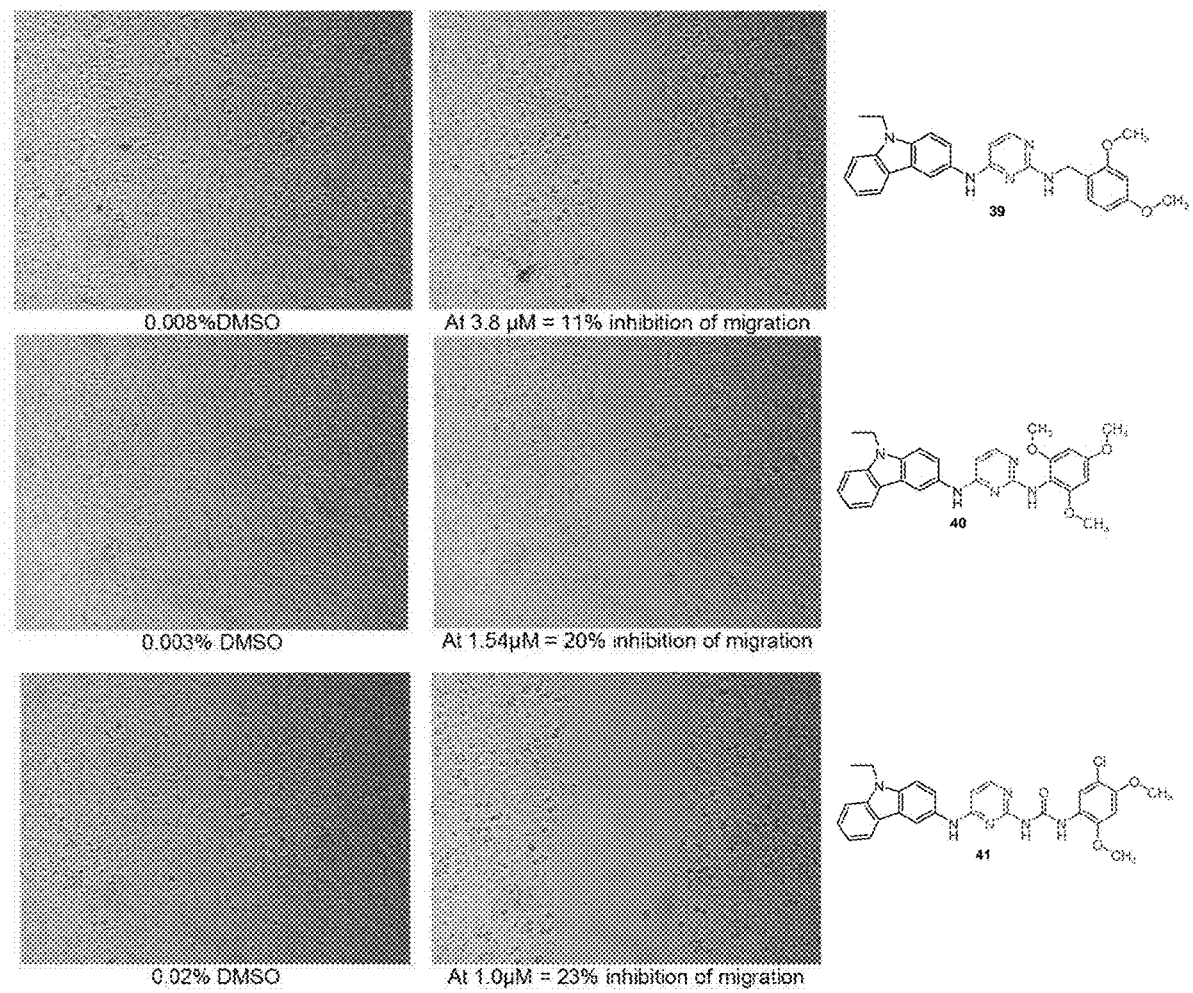
FIG. 12B shows a comparison of migration assays for Compounds 5, 10, and 11.

Compounds with modifications in Building Block C demonstrating inhibition of migration at a concentration of 0.2×IC$_{50}$ included compounds 5, 10 and 11, as shown in FIG. 12B.

Example 16: Synthesis of HV-118 and EHop-016 Derivative 8

Figure 13:
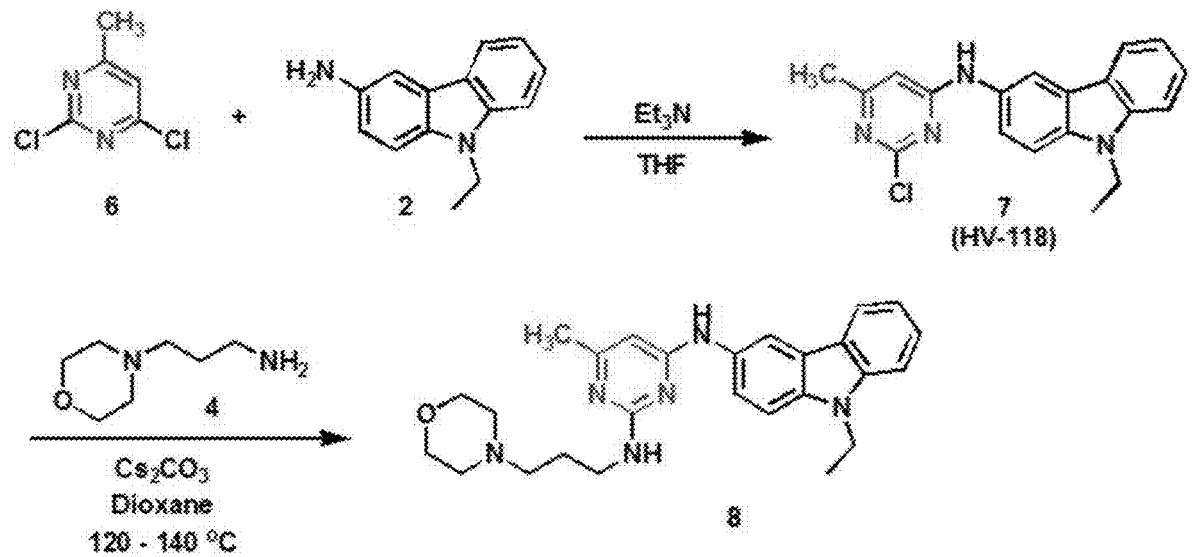
FIG. 13. Scheme 3B. Synthesis of HV-118 and EHop-016 derivative 8.

To explore new EHop-016 derivatives with minor modifications at the pyrimidine core building block A, compound HV-118 was synthesized (see Scheme 3B; FIG. 13). This compound was synthesized following essentially the same procedure as depicted in scheme 1 for the synthesis of EHop-016. However, instead of using precursor 2,4-dichloropyrimidine 1, a commercially available 2,4-dichloro-6-methylpyrimidine 6 was used.

The pyrimidine 6 is reacted with carbazole 2 via reflux in tetrahydrofuran in the presence of 1.2 equivalents triethylamine. Compared with previous purification procedures, to obtain 7 (HV-118) the crude was purified using silica gel chromatography (5:1 to 1:1, hexane-ethyl acetate), and the pure compound was collected in 17% yield. Reaction of product 7 with amine 4, representing building block C, in the presence of cesium carbonate in dioxane under microwave heating at 120 to 160° C. provided the desired EHop-016 derivative 8. By introducing a methyl group in position-6 of the pyrimidine, hydrophobic interactions with aromatic residues at the binding site of Rac may be improved. Consequently, such derivatives are hypothesized to be more potent Rac inhibitors and better anti-migratory compounds.

Example 17: Biological Effect of Compound 8

Figure 14A:
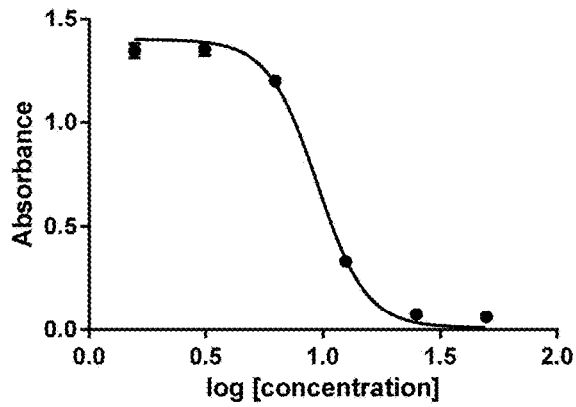
FIG. 14 (A-B). Log dose-response curve for compound 8 in MCF-7 (FIG. 14A) and SH-SY5Y neuroblastoma (FIG. 14B) cells.
Figure 14B:
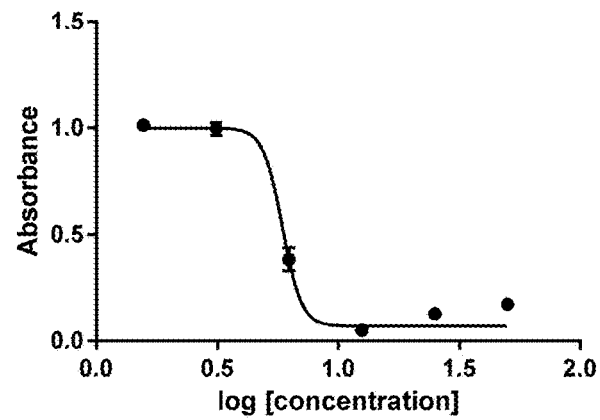
Figure 15A:
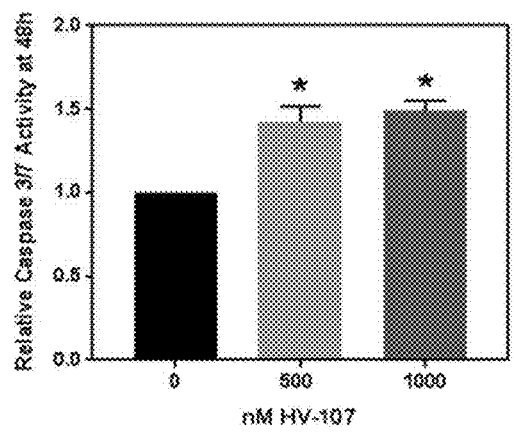
FIG. 15 (A-D). Effect of HV-107 and HV-118 on Caspase 3/7 activity.
Figure 15B:
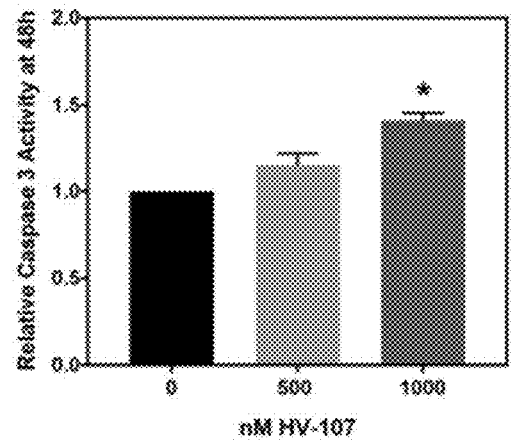
Figure 15C:
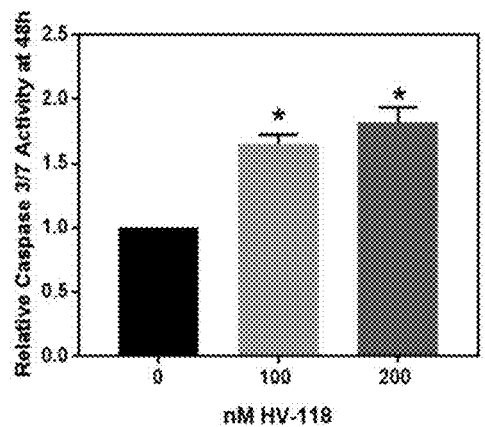
Figure 15D:
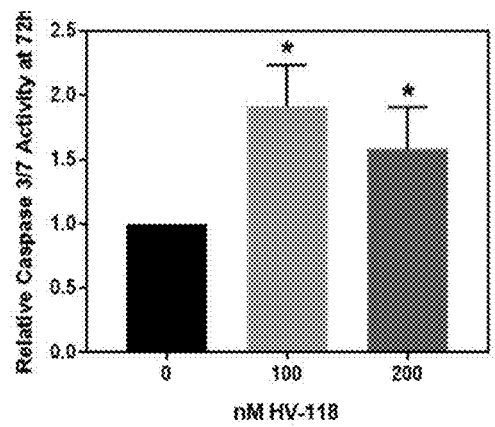
Figure 16A:
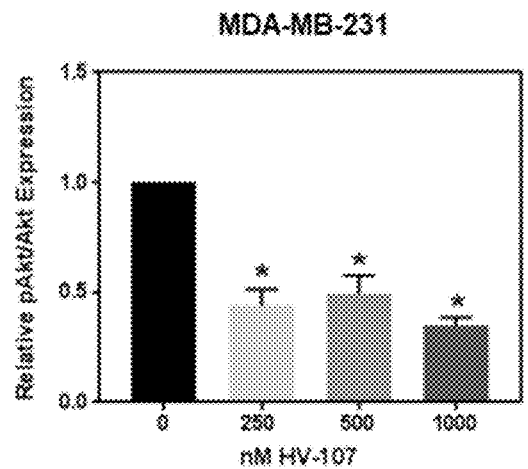
FIG. 16 (A-D). Inhibition of pAKT by HV-107 and HV-118.
Figure 16B:
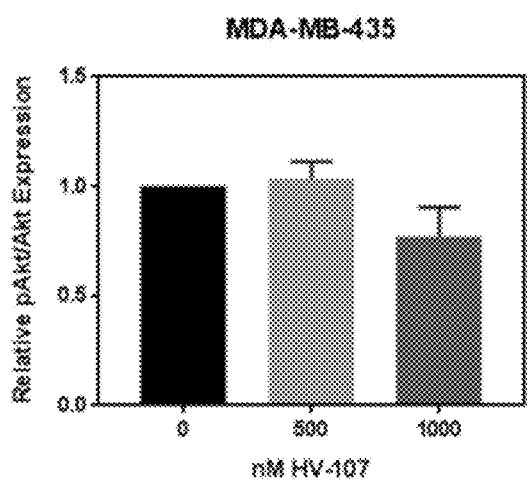
Figure 16C:
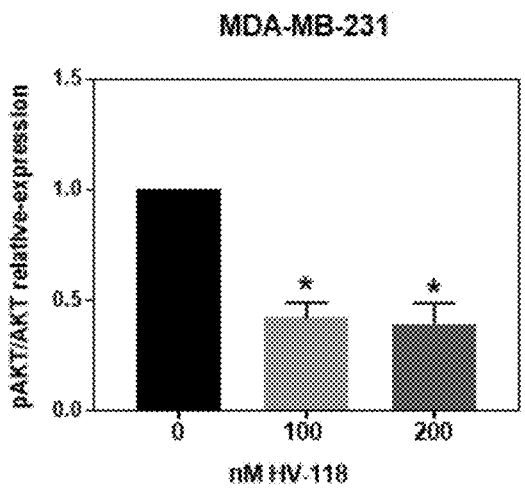
Figure 16D:
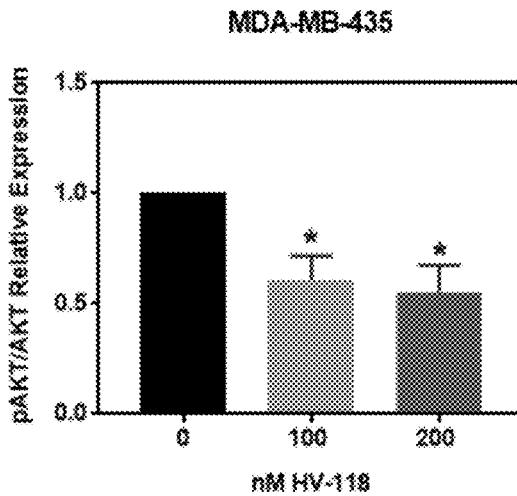

Compound 8 exhibited comparable growth inhibition potency to EHop-016, with GI$_{50}$=9.5 μM in MCF-7 cancer cell line and GI$_{50}$=6 μM in SH-SY5Y neuroblastoma cells (see FIG. 14A and FIG. 14B, respectively).

Example 18: Characteristics of EHOP-016 Derivatives

A panel of novel Ehop-016 derivatives was tested for their efficacy to inhibit Rac activation and selectively inhibit metastatic breast cancer cell viability, while presenting minor toxicity to non-cancerous mammary epithelial cells (MCF10A). Two Ehop-016 derivatives, HV-107 and HV-118, that are toxic to MDA-MB-231 and MDA-MB-435 metastatic breast cancer cells, show minimal or no inhibition of non-cancerous mammary epithelial cell viability at the concentrations tested. The effects of HV-107 and HV-118 on the inhibition of Rac activation were tested by pulldown assays. Results show that at 250 nM, HV-107 inhibits Rac activation by 60%; whereas HV-118 has a similar effect at 100 nM in MDA-MB-231 and MDA-MB-435 cells.

Subsequently, the effects of HV-107 and HV-118 were evaluated in cell survival and cell migration, known Rac-regulated cell functions relevant for cancer progression. The effects of HV-107 and HV-118 on cancer cell survival were determined by measuring the levels of active caspase 3 in MDA-MB-231 and MDA-MB-435 metastatic breast cancer cells after treatment with HV-107 at 500 and 1000 nM, or HV-118 at 100 and 200 nM for 48-72 h. After 48 h, HV-107 caused a significant 1.4-1.5 fold increase in caspase 3 activity in MDA-MB-231 (at 500 and 1000 nM) and MDA-MB-435 (at 1000 nM) cells. Similar results were observed in cells treated with HV-118. A 1.6-1.8 fold increase was demonstrated in caspase 3 activity in MDA-MB-231 cells after 48 h treatment with 100 and 200 nM HV-118; whereas, the same level of caspase 3 activity induction was observed in MDA-MB-435 cells at 72 h (FIG. 15 (A-D)). This data suggests that both HV-107 and HV-118 inhibit cell survival by promoting apoptosis, the major mechanism of programmed cell death. The effects of both compounds were also examined in the activity of Akt, an important kinase that promotes survival signaling, is frequently hyperactivated in malignant cancers, and can be regulated by Rac. Because Akt is activated by phosphorylation events, the effects of HV-107 and HV-118 were analyzed in Akt phosphorylation by western blot (FIG. 16 (A-D)). Results show HV-107 at 250-1000 nM (for 24 h) significantly inhibits Akt phosphorylation by 50-60% in MDA-MB-231 cells; and causes a moderate 25% inhibition of Akt phosphorylation in MDA-MB-435 cells at 1000 nM. On the other hand, HV-118 significantly inhibits Akt phosphorylation by 40-60% in both MDA-MB-231 and MDA-MB-435 metastatic breast cancer cells treated with 100 and 200 nM for 24 h.

Finally, wound healing assays were performed to assess the effects of HV-107 and HV-118 on metastatic breast cancer cell migration. Results show cell migration was significantly inhibited by 30-50% at 2000 nM HV-107 and by approximately 60% and 80% at 100 and 200 nM HV-118, respectively in the metastatic breast cancer cell lines MDA-MB-231 and MDA-MB435 (FIG. 17 (A-B)). Taken together, these results confirm that HV-107 and HV-118 significantly inhibit Rac regulated cell functions and Akt-mediated survival signaling in metastatic breast cancer cells.

Figure 19B:
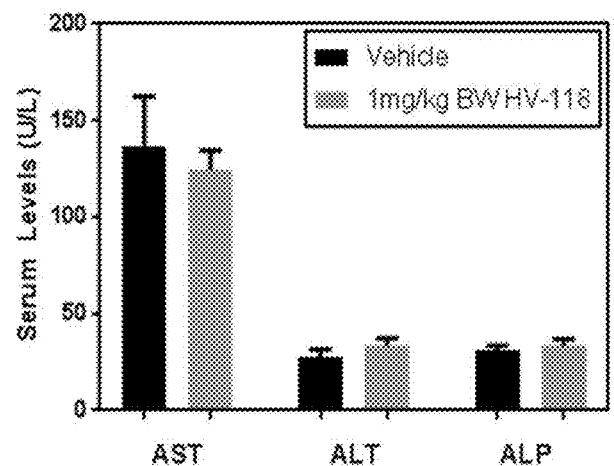
FIG. 19 (A-C). HV-118 toxicity assessment. Blood collected at necropsy was used for FIG. 19A. complete blood count (CBC) analysis and FIG. 19B. determination of serum levels of liver enzymes Alanine Aminotranferase (ALT), Aspartate Aminotransferse (AST), and Alkaline phosphatase (ALP). N=4-5 mice/group; error bars represent ±SEM.
FIG. 19C. Average mouse weight as a function of days following HV-118 administration. N=13-15 mice/group.
Figure 19C:
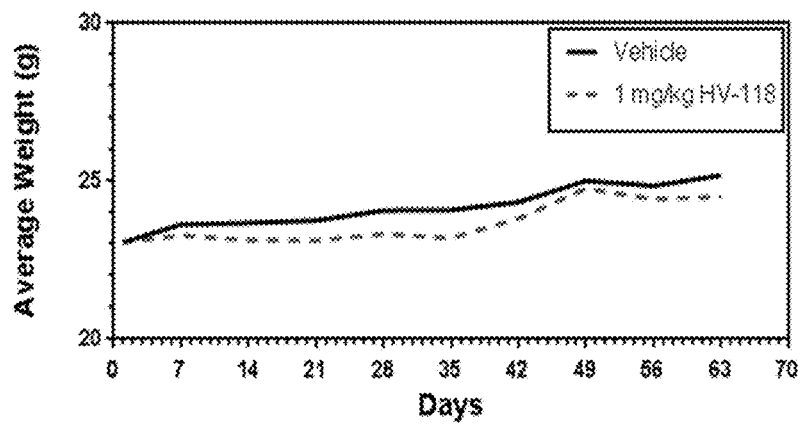

An in vivo study was performed to assess HV-118 toxicity and test its effects in mammary tumor growth and metastasis. Immunocompromised mice were inoculated with green fluorescent protein (GFP)-tagged MDA-MB-231 cells. After tumors reached an average size of 80 mm$^3$, mice (n=15/group) were administered with control or HV-118 at 1 mg/kg body weight (BW) by intraperitoneal (i.p.) injection every day from Monday to Friday for approximately 2 months. The effects of HV-118 on tumor growth were monitored weekly by in situ fluorescence image analysis (starting from day 1 of treatment). Mammary tumor growth was quantified using Image J software, as the pixel intensity (integrated density) determined from digital tracing of the fluorescent tumor area at each imaging session and calculated as a function of the fluorescence intensity on day one of treatment. At necropsy, blood was collected, and organs were dissected and stored in liquid nitrogen. Metastatic foci were quantified for fluorescence intensity and area of fluorescence (lesion size) for each organ by Image J analysis of digital images from a fluorescence stero microscope. Results show a 30% reduction in tumor growth by 1 mg/kg BW HV-118 and a significant reduction of >90% in metastasis to lung and liver (FIG. 18 (A-D)). Toxicity was assessed by: 1) performing a hematologic profile (complete blood count (CBC) analysis), 2) measuring serum levels of liver enzymes Alanine Aminotranferase (ALT), Aspartate Aminotransferse (AST), and Alkaline phosphatase (ALP), and 3) monitoring animal weight throughout the study. Results showed no changes in any of the parameters measured by the hematologic profile, serum levels of ALT, AST, or ALP, or mice weights; thus, suggesting no toxicity by HV-118 at the tested dose (FIG. 19 (A-C)).

PUBLICATIONS

The following publications are incorporated by reference to the extent they relate materials and methods disclosed herein.
1. Hunter, K. W.; Crawford, N. P.; Alsarraj, *J. Breast Cancer Research: BCR.* 2008, 10(Suppl 1): S2. Doi:10.1186/bcr1988.
2. Hall, A. *Biochem. Soc. Trans.* 2005, 33, 891.
3. Vega, F. M.; Ridley, A. *J. FEBS Lett.* 2008, 582, 2093.
4. Głuszyńska, A. *Eur. J. Med. Chem.* 2015, 94, 405.
5. Guillonneau, C.; Pierre, A.; Charton, Y.; Guilbard, N.; Berthier, L. K.; Leonce, S.; Michael, A.; Bisagni, E.; Atassi, G. *J. Med. Chem.* 1999, 42, 2191.
6. Caruso, A.; Chiret, A. S. V.; Lancelot, J. C.; Sinicropi, M. S.; Garofalo, A.; Rault, S. *Molecules* 2008, 13, 1312.
7. Chakrabarty, M.; Ghosh, N.; Harigaya, Y. *Tetrahedron Lett.* 2004, 45, 4955.
8. Issa, S.; Walchshofer, N.; Kassab, I.; Termoss, H.; Chamat, S.; Geahchan, A.; Bouaziz, Z. *Eur. J. Med. Chem.* 2010, 45, 2567.
9. Danish, A. I.; Prasad, K. J. R. *Indian J. Heterocycl. Chem.* 2006, 14, 19.
10. Indumati, T.; Fronczek, F. R.; Prasad, K. J. R. *J. Mol. Struct.* 2012, 1016, 134.
11. Kantevari, S.; Yempala, T.; Surineni, G.; Sridhar, B.; Sriram, D. *Eur. J. Med. Chem.* 2011, 46, 4827.
12. Bashir, M.; Bano, A.; Subhan-Ijaz, A.; Ahmad-Chaudary, B. *Molecules* 2015, 20, 13496.
13. Wang, Y. M.; Hu, L. X.; Liu, Z. M.; You, X. F.; Zhang, S. H.; Qu, J. R.; Li, Z. R.; Li, Y.; Kong, W. J.; He, H. W.; Shao, R. G.; Zhang, L. R.; Peng, Z. G.; Boykin, D. W.; Jiang, J. D. *Clin. Cancer Res.* 2008, 14, 6218.
14. Liu, C. H.; Lin, C.; Tsai, K. J.; Chuang, Y. C.; Huang, Y. L.; Lee, T. H.; Huang, L. J.; Chan, H. C. *Oncol. Rep.,* 2013, 29, 1501.
15. Yoon, S.; Kim, J. H.; Lee, Y. J.; Ahn, M. Y.; Choi, G.; Kim, W. K.; Yang, Z.; Lee, H. J.; Moon, H. R.; Kim, H. S. *Eur. J. Pharmacol.* 2012, 697, 24.
16. Montalvo-Ortiz, B. L.; Castillo-Pichardo, L.; Hernández, E.; Humphries-Bickley, T.; De La Mota-Peynado, A.; Cubano, L. A.; Vlaar, C. P.; Dharmawardhane, S. *J. Biol. Chem.* 2012, 287, 13228.
17. Castillo-Pichardo, L.; Humphries-Bickley, T.; de la Parra, C.; Forestier-Roman, I.; Martínez-Ferrer, M.; Hernandez, E., et al. *Transl. Oncol.* 2014, 7, 546. Liang, C-C.; Park, A. Y.; Guan, J-L. *Nature Protoc.* 2007, 2, 329.
18. Maldonado M D M, Dharmawardhane S. Targeting Rac and Cdc42 GTPases in cancer. *Cancer Res.* 2018 Jun. 15; 78(12):3101-3111
19. Cornelis P. Vlaar, Linette Castillo-Pichardo, Julia I. Medina, Cathyria M. Marrero-Serra, Ericka Vélez, Zulma Ramos, Eliud Hernández, Design, synthesis and biological evaluation of new carbazole derivatives as anti-cancer and anti-migratory agents. *Bioorg Med Chem* (2018) January 8; 26, 884-890.

The invention claimed is:
1. A compound of formula,

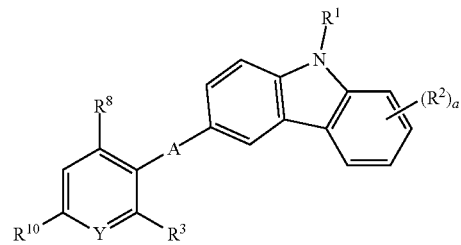

wherein
$R^1$ is H, $C_1$-$C_6$ alkyl, $C_2$-$C_6$ alkenyl, or $C_2$-$C_6$ alkynyl;
each $R^2$ is independently deuterium, halogen, —OH, —CN, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —OR$^5$, —C(O)OR$^5$, —C(O)NR$^5$R$^6$, —NH$_2$, —NH($C_1$-$C_6$ alkyl), —N($C_1$-$C_6$ alkyl)$_2$, —NHC(O)$C_1$-$C_6$ alkyl, —CO$_2$H, —C(O)OC$_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl); wherein each hydrogen atom in $C_1$-$C_6$ alkyl, $C_2$-$C_6$ alkenyl, $C_2$-$C_6$ alkynyl, $C_3$-$C_6$ cycloalkyl, and $C_6$-$C_{10}$ aryl is independently optionally substituted;
A is —O—, —S—, —N(R$^7$)—, —N(R$^7$)C(O)—, or —C(O)N(R$^7$)—;
Y is —N—;
$R^3$ is —NHR$^{11}$, —NR$^{11}$R$^{12}$, —C(O)$C_1$-$C_6$ alkyl, —C(O)R$^{11}$, or 3-to 7-membered heterocycloalkyl; wherein each hydrogen atom in —C(O)$C_1$-$C_6$ alkyl or 3-to 7-membered heterocycloalkyl is optionally substituted by deuterium, halogen, —OH, oxo, —CN, —O$C_1$-$C_6$ alkyl, —NH$_2$, —NH($C_1$-$C_6$ alkyl), —NH($C_6$-$C_{10}$ aryl), —NH($C_6$-$C_{10}$ aryl)-N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)$C_1$-$C_6$ alkyl, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_1$-$C_6$ alkyl, $C_2$-$C_6$ alkenyl, $C_2$-$C_6$ alkynyl, $C_3$-$C_6$ cycloalkyl, 3-to 7-membered heterocycloalkyl, $C_6$-$C_{10}$ aryl, $C_1$-$C_6$ alkyl-(3-to 7-membered heterocycloalkyl), —CF$_3$, —CHF$_2$, or —CH$_2$F;

wherein each of $R^{11}$ and $R^{12}$ is independently H, deuterium, $C_1$-$C_6$ alkyl, $C_2$-$C_6$ alkenyl, $C_2$-$C_6$ alkynyl, $C_3$-$C_6$ cycloalkyl, $C_1$-$C_6$ heteroalkyl, 3- to 7-membered heterocycloalkyl, $C_6$-$C_{10}$ aryl, $C_1$-$C_6$alkyl-(3- to 7-membered heterocycloalkyl), heteroaryl, —NH$C_1$-$C_6$alkyl, —N($C_1$-$C_6$ alkyl)$_2$, —S(O)$_2$$C_1$-$C_6$ alkyl, —CF$_3$, —CHF$_2$, or —CH$_2$F, wherein each hydrogen in $C_1$-$C_6$alkyl, $C_1$-$C_6$heteroalkyl, and $C_6$-$C_{10}$ aryl is optionally substituted by —O—$C_1$-$C_6$alkyl, $C_3$-$C_6$ cycloalkyl, 3- to 7-membered heterocycloalkyl, 3- to 7-membered substituted heterocycloalkyl, —CH$_2$CN, —N($C_1$-$C_6$ alkyl)$_2$, optionally substituted aryl, —C(O)NH-optionally substituted aryl, hydroxy, or mono- or bicyclic heteroaryl;

or $R^3$ is —OR$^{11}$, wherein $R^{11}$ is $C_1$-$C_6$ alkyl, $C_2$-$C_6$ alkenyl, $C_2$-$C_6$ alkynyl, $C_3$-$C_6$ cycloalkyl, $C_1$-$C_6$ heteroalkyl, 3- to 7-membered heterocycloalkyl, $C_6$-$C_{10}$ aryl, $C_1$-$C_6$alkyl-(3-to 7-membered heterocycloalkyl), heteroaryl, —NH$C_1$-$C_6$ alkyl, —N($C_1$-$C_6$ alkyl)$_2$, —S(O)$_2$$C_1$-$C_6$ alkyl, —CF$_3$, —CHF$_2$, or —CH$_2$F, wherein each hydrogen in $C_1$-$C_6$ alkyl, $C_1$-$C_6$ heteroalkyl, and $C_6$-$C_{10}$ aryl is optionally substituted by $C_3$-$C_6$ cycloalkyl, 3- to 7-membered heterocycloalkyl, 3- to 7-membered substituted heterocycloalkyl, —CH$_2$CN, —N($C_1$-$C_6$ alkyl)$_2$, optionally substituted aryl, —C(O)NH-optionally substituted aryl, hydroxy, or mono- or bicyclic heteroaryl $R^8$ is H, deuterium, halo $C_1$-$C_6$ alkyl, $C_2$-$C_6$ alkenyl, $C_2$-$C_6$ alkynyl, $C_3$-$C_6$ cycloalkyl, $C_1$-$C_6$ heteroalkyl, 3- to 7-membered heterocycloalkyl, $C_6$-$C_{10}$ aryl, $C_1$-$C_6$alkyl-(3-to 7-membered heterocycloalkyl), mono- or bicyclic heteroaryl, —O$C_1$-$C_6$ alkyl, —NH$C_1$-$C_6$ alkyl, —N($C_1$-$C_6$ alkyl)$_2$, —S(O)$_2$$C_1$-$C_6$ alkyl, —CF$_3$, —CHF$_2$, or —CH$_2$F, wherein each hydrogen in $C_1$-$C_6$alkyl, $C_1$-$C_6$ heteroalkyl, 3- to 7-membered heterocycloalkyl, mono- or bicyclic heteroaryl, and $C_6$-$C_{10}$ aryl is optionally substituted by —O—$C_1$-$C_6$alkyl, $C_3$-$C_6$ cycloalkyl, 3- to 7-membered heterocycloalkyl, 3- to 7-membered substituted heterocycloalkyl, —CH$_2$CN, —N($C_1$-$C_6$ alkyl)$_2$, —O$C_1$-$C_6$ alkyl, optionally substituted aryl, —C(O)NH-optionally substituted aryl, hydroxy, or mono- or bicyclic heteroaryl;

$R^{10}$ is H, deuterium, halo, $C_1$-$C_6$ alkyl, $C_2$-$C_6$ alkenyl, $C_2$-$C_6$ alkynyl, $C_3$-$C_6$ cycloalkyl, 3-to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted;

each $R^5$, $R^6$, and $R^7$ is independently H, deuterium, $C_1$-$C_6$ alkyl, $C_2$-$C_6$ alkenyl, $C_2$-$C_6$ alkynyl, $C_3$-$C_6$ cycloalkyl, $C_1$-$C_6$ heteroalkyl, 3- to 7-membered heterocycloalkyl, $C_6$-$C_{10}$ aryl, $C_1$-$C_6$ alkyl-(3- to 7-membered heterocycloalkyl), heteroaryl, —O$C_1$-$C_6$ alkyl, —NH$C_1$-$C_6$ alkyl, —N($C_1$-$C_6$ alkyl)$_2$, —S(O)$_2$$C_1$-$C_6$ alkyl, —CF$_3$, —CHF$_2$, or —CH$_2$F, wherein each hydrogen in $C_1$-$C_6$alkyl, $C_1$-$C_6$ heteroalkyl, and $C_6$-$C_{10}$ aryl is optionally substituted by —O—$C_1$-$C_6$alkyl, $C_3$-$C_6$ cycloalkyl, 3- to 7-membered heterocycloalkyl, 3- to 7-membered substituted heterocycloalkyl, —CH$_2$CN, —N($C_1$-$C_6$ alkyl)$_2$, —O$C_1$-$C_6$ alkyl, optionally substituted aryl, —C(O)NH-optionally substituted aryl, hydroxy, or mono- or bicyclic heteroaryl; and a is 0, 1, 2, or 3;

or a salt thereof.

2. A method of treating breast cancer in a patient in need thereof the method comprising administering to the patient an effective amount of a compound according to claim 1.

3. The method of claim 2, wherein the compound reduces the expression of a Bcl-2 protein.

4. The method of claim 2, wherein the breast cancer is mediated by a GTPase.

5. The method of claim 4, wherein the GTPase is Rac 1 or Cdc42.

6. The method of claim 2, wherein the compound inhibits PAK1/2 activity.

7. The method of claim 2, wherein the compound inhibits STAT3 activity.

8. The method of claim 2, wherein the effective amount of the compound is in a range of about 0.01 mg/kg to about 100 mg/kg of body weight of the patient.

* * * * *